United States Patent
Alexandre et al.

(10) Patent No.: US 11,040,975 B2
(45) Date of Patent: Jun. 22, 2021

(54) CARBOCYCLIC NUCLEOSIDE REVERSE TRANSCRIPTASE INHIBITORS

(71) Applicants: Merck Sharp & Dohme Corp., Rahway, NJ (US); Idenix Pharmaceuticals LLC, Cambridge, MA (US)

(72) Inventors: Francois-Rene Alexandre, Montpellier (FR); Rachid Rahali, Saint Laurent des Arbres (FR); Izzat Raheem, Doylestown, PA (US); Christophe Parsy, Jacou (FR)

(73) Assignees: Merck Sharp & Dohme Corp., Rahway, NJ (US); Idenix Pharmaceuticals LLC, Cambridge, MA (US)

( * ) Notice: Subject to any disclaimer, the term of this patent is extended or adjusted under 35 U.S.C. 154(b) by 0 days.

(21) Appl. No.: 16/212,121

(22) Filed: Dec. 6, 2018

(65) Prior Publication Data

US 2019/0177326 A1 Jun. 13, 2019

Related U.S. Application Data

(60) Provisional application No. 62/596,378, filed on Dec. 8, 2017.

(51) Int. Cl.

| | | |
|---|---|---|
| *C07D 473/40* | (2006.01) | |
| *C07D 473/32* | (2006.01) | |
| *C07D 239/47* | (2006.01) | |
| *C07D 239/54* | (2006.01) | |
| *A61K 31/675* | (2006.01) | |
| *A61K 31/7072* | (2006.01) | |
| *A61K 31/522* | (2006.01) | |
| *A61K 31/513* | (2006.01) | |
| *C07F 9/6561* | (2006.01) | |
| *A61K 31/52* | (2006.01) | |
| *C07F 9/6512* | (2006.01) | |

(52) U.S. Cl.
CPC .......... *C07D 473/40* (2013.01); *A61K 31/513* (2013.01); *A61K 31/52* (2013.01); *A61K 31/522* (2013.01); *A61K 31/675* (2013.01); *A61K 31/7072* (2013.01); *C07D 239/47* (2013.01); *C07D 239/54* (2013.01); *C07D 473/32* (2013.01); *C07F 9/6512* (2013.01); *C07F 9/6561* (2013.01); *C07F 9/65616* (2013.01)

(58) Field of Classification Search
None
See application file for complete search history.

(56) References Cited

U.S. PATENT DOCUMENTS

| | | | |
|---|---|---|---|
| 5,567,703 A * | 10/1996 | Vince | ............... C07D 487/04 |
| | | | 514/263.37 |
| 6,333,315 B1 | 12/2001 | Ohrui et al. | |
| 6,403,568 B1 | 6/2002 | Ohrui et al. | |
| 7,339,053 B2 | 3/2008 | Kohgo et al. | |
| 7,625,877 B2 | 12/2009 | Kohgo et al. | |
| 7,879,815 B2 | 2/2011 | MacCoss et al. | |
| 8,039,614 B2 | 10/2011 | Kohgo et al. | |
| 8,765,710 B2 | 7/2014 | Sofia | |
| 8,835,615 B2 | 9/2014 | Chang | |
| 2004/0229839 A1 | 11/2004 | Babu et al. | |
| 2010/0234584 A1 | 9/2010 | Chang | |
| 2011/0171192 A1 | 7/2011 | Tomiyama et al. | |

FOREIGN PATENT DOCUMENTS

| | | |
|---|---|---|
| CN | 101003550 | 7/2007 |
| CN | 101003550 A | 7/2007 |
| EP | 2177527 A1 | 4/2010 |
| JP | 2011503234 A | 1/2011 |
| PE | 000605-2016 A1 | 7/2016 |
| WO | 1991010671 A1 | 7/1991 |
| WO | 1995021184 A1 | 8/1995 |
| WO | 1998016184 A2 | 4/1998 |
| WO | 2002100354 A1 | 12/2002 |
| WO | 2003061576 A2 | 7/2003 |
| WO | 2003099840 A1 | 12/2003 |
| WO | 2004106356 A1 | 12/2004 |
| WO | 2008048981 A2 | 4/2008 |
| WO | 2008082602 A2 | 7/2008 |

(Continued)

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
Beaumont, K., et al,, "Design of Ester Prodrugs to Enhance Oral Absorption of Poorly Permeable Compounds: Challenges to the Discovery Scientist", Current Drug Metabolism, 2003, pp. 461-485, vol. 4.
Bobeck, et al.,, "Advances in Nucleoside Monophosphate Prodrugs As Anti-HCV Agents", Antiviral Therapy, 2010, pp. 935-950, vol. 15.

(Continued)

*Primary Examiner* — Traviss C McIntosh, III
(74) *Attorney, Agent, or Firm* — Carol S. Quagliato; John C. Todaro

(57) ABSTRACT

The present invention is directed carbocyclic nucleoside reverse transcriptase inhibitors compounds of Formula I

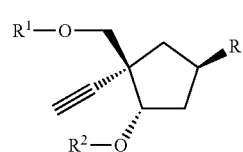

and their use in the inhibition of HIV reverse transcriptase, the prophylaxis of infection by HIV, the treatment of infection by HIV, and the prophylaxis, treatment, and delay in the onset or progression of AIDS and/or ARC.

8 Claims, No Drawings

(56) References Cited

FOREIGN PATENT DOCUMENTS

| WO | 2008089105 | A2 | 7/2008 |
|---|---|---|---|
| WO | 2009009951 | A1 | 1/2009 |
| WO | 2009067409 | A1 | 5/2009 |
| WO | 2009132123 | A1 | 10/2009 |
| WO | 2009132135 | A1 | 10/2009 |
| WO | 2010002877 | A2 | 1/2010 |
| WO | 20100002877 | A2 | 1/2010 |
| WO | 2010026153 | A1 | 3/2010 |
| WO | 2010027005 | A1 | 3/2010 |
| WO | 2010036407 | A2 | 4/2010 |
| WO | 2010075549 | A2 | 7/2010 |
| WO | 2010084115 | A2 | 7/2010 |
| WO | 2010108140 | A1 | 9/2010 |
| WO | 2011005860 | A2 | 1/2011 |
| WO | 2011075517 | A1 | 6/2011 |
| WO | 2012012776 | A1 | 1/2012 |
| WO | 2012037038 | A1 | 3/2012 |
| WO | 2013138236 | A1 | 9/2013 |
| WO | 2015069939 | A1 | 5/2015 |

OTHER PUBLICATIONS

Cristalli, G., et al, "Adenosine Deaminase Inhibitors. Synthesis and Biological Activity of Deaza Analogues of Erythro-9-(2-Hydroxy-3-Nonyl)Adenine", J. Med. Chem., 1988, pp. 390-393, vol. 31.

Desai, M., et al "Antiretroviral Drugs: Critical Issues and Recent Advances", Indian J. Pharmacol., 2012, pp. 288-298, vol. 44, No. 3.

Erion, M., "Liver-Targeted Drug Delivery Using HepDirect Prodrugs", Metabsis Therapeutics, Inc., 2008, pp. 7-12, 17th Internatinal Symposium on Microsomes and drug Oxidations, Saratoga Springs (NY, USA), US.

Furman, et al.,, "Nucleoside Analog Inhibitors of Hepatitis C Viral Replication: Recent Advances, Challenges and Trends", Future Medicinal Chemistry, 2009, pp. 1429-1452, vol. 1.

Gupta, M. et al, "Adenosine Deaminase in Nucleoside Synthesis. A Review", Collect. Czech. Chem. Commun., 2006, pp. 769-787, vol. 71, No. 6.

Hale, et al, "Phosphorylated Morpholine Acetal Human Neurokinin-1 Receptor Antagonists as Water-Soluble Prodrugs", J. Med. Chem, 2000, pp. 1234-1241, vol. 43.

Higuchi, T., et al., "Pro-drugs as NovelDelivery Systems", A.C.S. Symposium Series, 1987, 14, pp. 1-6.

International Search Report and Written Opinion of the International Searching Authority, PCT/CN2014/074294—International Filing Date Mar. 28, 2014.

International Search Report and Written Opinion of the International Searching Authority, PCT/US2015/022621—International Filing Date Mar. 3, 2015.

Kazuhiro Haraguchi, et al, "Synthesis of 4'-Ethynyl-2'-Deoxy-4'-Thioribonucleosides and Discovery of a Highly Potent and Less Toxic NRTI", ACS Medicinal Chemistry Letters, 2011, pp. 692-697, vol. 2, No. 9, WO.

Kesisoglou, F., et al, "Nanosizing—Oral Formulation Development and Biopharmaceutical Evaluation", Advance Drug Delivery Reviews, 2007, pp. 631-644, vol. 59, US.

Kirby, K., et al, "Effects of Substitutions at the 4' and 2 Positions on the Bioactivity of 4'-Ethynyl-2-Fluoro-2'-Deoxyadenosine", Antimicrobial Agents and Chemotherapy, 2013, pp. 6254-6264, vol. 57, No. 12.

Kodama, et al, "4'-Ethynyl Nucleoside Analogs: Potent Inhibitors of Multidrug-Resistant Human Immunodeficiency Virus Variants in Vitro", Antimicrobial Agents and Chemotherapy, American Society for Microbiology, 2001, pp. 1539-1546, vol. 45, No. 5, WO.

Kohgo, S., et al.,, "Design, Efficient Synthesis, and Anti-HIV Activity of 4'-C-Cyano-and 4'-C-Ethynyl-2'-Deoxy Purine Nucleosides", Nucleosides, Nucleotides & Nucleic Acids, 2004, pp. 671-690, vol. 23, No. 4.

Kohgo, S., et al.,, "Synthesis of 4'-C-Ethynyl and 4'-C-Cyano Purine Nucleosides from Natural Nucleosides and Their Anti-HIV Activity", Nucleosides, Nucleotides & Nucleic Acids, 2003, pp. 887-889, vol. 22, Nos. 5-8.

Krogsgaard-Larsen, P., et al, "Design and Applcation of Prodrugs", Drug Design and Discovery, 2002, pp. 461-485, 4d Edition, vol. 4, US.

Larsen, C.S., et al,, "Design and Application of Prodrugs", Textbook of Drug Design and Discovery, 3rd ED, 2002, pp. 410-458, Chapter 14, US.

Marongiu, M., et al, "Enhancement of the Anti-HIV-1 Activity of ddAdo by Coformycin, EHNA and Deaza-EHNA Derivatives", Microbiologica, 1995, pp. 359-370, vol. 18, No. 4.

Mehellou, Y., "Phosphoramidate Prodrugs Deliver with Potency Against Hepatitis C Virus", Chem. Med. Chem., 2010, pp. 1841-1842, vol. 5.

Obara, T., et al, "New Neplanocin Analogues. 7. Synthesis and Antiviral Activity of 2-Halo Derivatives of Neplanocin A1", Journal of Medicial Chemistry, 1996, pp. 3847-3852, vol. 39, No. 19.

Ohrui, H., "4'-C-Ethynyl-2'-Deoxynucleosides", Modified Nucleosides: In Biochemistry, Biotechnology and Medicine, 2008, pp. 425-431.

Serajuddin, A., et al.,, "Solid Dispersion of Poorly Water-Soluble Drugs: Early Promises, Subsequent Problems, and Recent Breakthroughs", J. Pharm Sci., 1999, pp. 1058-1066, vol. 88, No. 10.

Shuto, S., et al, "New Neplanocin Analogues. IV. 2-Fluoroneplanocin A: An Adenosine Deaminase-Resistant Equivalent of Neplanocin A1", Chem.Pharm. Bull., 1994, pp. 1688-1690, vol. 42, No. 8.

\* cited by examiner

CARBOCYCLIC NUCLEOSIDE REVERSE TRANSCRIPTASE INHIBITORS

RELATED APPLICATIONS

This application claims priority to U.S. Provisional Application No. 62/596,378, filed Dec. 8, 2017. The aforementioned application to which this application claims priority is herein incorporated by reference in its entirety.

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are nucleoside RT inhibitors (NRTI) such as 3'-azido-3'-deoxythymidine (AZT), 2',3'-dideoxyinosine (ddI), 2',3'-dideoxycytidine (ddC), d4T, 3TC, abacavir, emtricitabine, and tenofovir disoproxil fumarate, as well as non-nucleoside RT inhibitors (nNRTI) such as nevirapine, delavirdine, and efavirenz.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of anti-retrovirals to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a continuing need for new RT inhibitors that are effective against mutant HIV strains.

SUMMARY OF THE INVENTION

The present invention is directed to carbocyclic nucleoside derivatives and their use in the inhibition of HIV reverse transcriptase, the prophylaxis of infection by HIV, the treatment of infection by HIV, and the prophylaxis, treatment, and delay in the onset or progression of AIDS and/or ARC.

DETAILED DESCRIPTION OF THE INVENTION

The present invention is directed to compounds having structural Formula I:

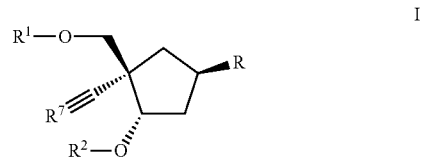

or a pharmaceutically acceptable salt thereof, wherein:
R is

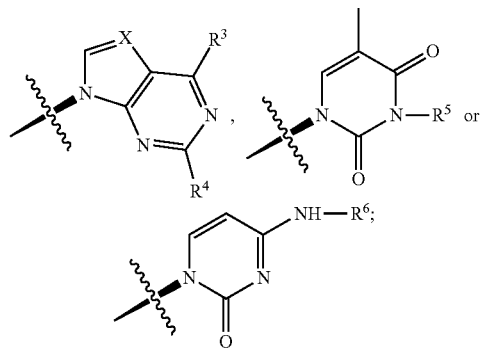

X is —O— or —C(H)—;
$R^7$ is —CH, —N, —$C_{1-6}$ alkyl or —C-aryl;
$R^1$ is

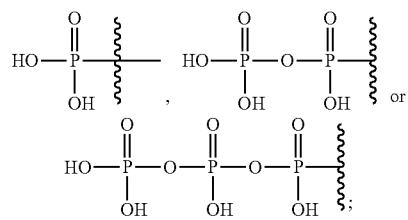

or a pro-drug modification of the mono-, di- or triphosphate;
$R^2$ is H or —$CH_2$—O—$C_{1-6}$alkyl;
$R^3$ is halo, —$NH_2$, oxo (=O), —O—$C_{1-6}$alkyl or —O—C(O)—N(phenyl)$_2$;
$R^4$ is halo or —$NR^aR^b$;
$R^a$ and $R^b$ are each independently selected from —H, —$C_{1-6}$alkyl or —C(O)—$C_{1-6}$alkyl;
$R^5$ is —H or —C(O)-phenyl; and
$R^6$ is —H or —C(O)-phenyl.

In Embodiment A of this invention are compounds of Formula I or the pharmaceutically acceptable salts thereof wherein:

$R^1$ is H,

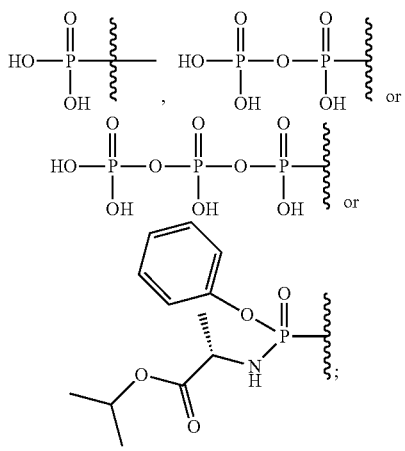

$R^2$ is H or —$CH_2$—O—$C_{1-3}$alkyl;
$R^3$ is halo, —$NH_2$, oxo, —O—$C_{1-3}$alkyl or —O—C(O)—N(phenyl)$_2$;
$R^4$ is halo, —$NH_2$ or —NH—C(O)—$C_{1-3}$alkyl;
and the remaining variables are as defined in Formula I.

The present invention includes each of the Examples described herein, and pharmaceutically acceptable salts thereof. The invention also encompasses pharmaceutical compositions comprising an effective amount of a compound of the invention or a pharmaceutically acceptable salt thereof, and a pharmaceutically acceptable carrier.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-3}$ alkyl" refers to n- and iso-propyl, ethyl and methyl.

The term "aryl" (or "$C_6$-$C_{10}$ aryl") refers to (i) phenyl, or (ii) 9- or 10-membered bicyclic, fused carbocylic ring systems in which at least one ring is aromatic. Suitable aryls include, for example, phenyl, naphthyl, tetrahydronaphthyl (tetralinyl), or indenyl. In a particular class of compounds of Formula I and embodiments thereof, aryl is phenyl or naphthyl, and more particularly aryl is phenyl.

The term "halo" refers to referred to as fluoro, chloro, bromo, and iodo. A particular class of interest for compounds of Formula I and embodiments thereof is each of fluoro and chloro.

The term "C(O)" refers to carbonyl.

Combinations of substituents and/or variables are permissible only if such combinations result in stable compounds.

As would be recognized by one of ordinary skill in the art, certain of the compounds of the present invention can exist as tautomers. All tautomeric forms of these compounds, whether isolated individually or in mixtures, are within the scope of the present invention. For example, in instances where an —OH or oxo substituent is permitted on a heteroaromatic ring and keto-enol tautomerism is possible, it is understood that the substituent might in fact be present, in whole or in part, in the alternative oxo (=O) or hydroxy (—OH) form.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I and its embodiments.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which is not biologically or otherwise undesirable (e.g., is neither toxic nor otherwise deleterious to the recipient thereof).

When the compounds of Formula I contain one or more acidic or basic groups the invention also includes the corresponding pharmaceutically acceptable salts. Thus, the compounds of Formula I which contain acidic groups (e.g., —COOH or a phenolic group) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Another embodiment of the present invention is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

The compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof which include any combination of stereoisomer, tautomer, solvate, hydrate, salt and/or physical forms of said pro-drugs, where such forms are possible unless specified otherwise.

Prodrug modification of the compounds of the invention are contemplated herein. Prodrugs of compounds of Formula I, or pharmaceutically acceptable salts thereof, can exhibit enhanced solubility, absorption, and/or lipophilicity compared to the compounds per se, thereby resulting in increased bioavailability and efficacy. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" as it relates to the compound of Formula I herein means a compound (e.g., a drug precursor), which may be in the form of a pharmaceutically acceptable salt, that is transformed intracellularly/in vivo to provide a compound of Formula I wherein $R^1$ is

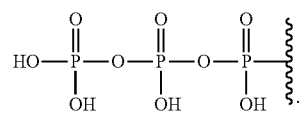 [SMILES: *P(=O)(O)OP(=O)(O)OP(=O)(O)O]

The in vivo transformation may occur by various mechanisms, e.g., an enzyme-catalyzed chemical reaction, a metabolic chemical reaction, and/or a spontaneous chemical reaction (e.g., solvolysis), such as, for example, through hydrolysis in blood. This invention encompasses any prodrugs which convert, due to intracellular/in vivo conversion, to a 4'-substituted Nucleoside Derivative of a compound of Formula I which is an inhibitor of HIV reverse transcriptase.

It is understood that a compound of Formula I or a salt thereof, wherein, for example, $R^1$ is (1) —H, (2) a pro-drug modification of the tri-phosphate; or

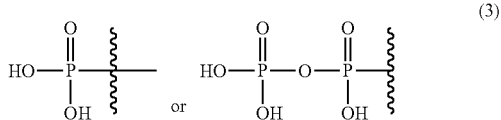 [SMILES: *P(=O)(O)O ; *P(=O)(O)OP(=O)(O)O]

or a prodrug modification of the mono- or di-phosphate; may be converted intracellularly/in vivo by one or more mechanisms (e.g., enzyme-catalyzed chemical reactions) to the corresponding 5' triphosphate

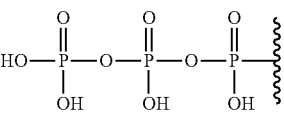 [SMILES: *P(=O)(O)OP(=O)(O)OP(=O)(O)O]

(i.e., wherein R$^1$ is —P(O)(OH)—O—P(O)(OH)—O—P(O)(OH)$_2$). While not wishing to be bound by any particular theory, the 5'triphosphate is generally understood to be responsible for inhibiting the HIV RT enzyme and for the resulting antiviral activity after administration of the compound of Formula I to a subject.

The term "pro-drug modification of the mono-, di- or triphosphate" as used herein includes, but is not limited to, 5'-alcohol-derived prodrugs such as —P(O)(—O—C$_1$-C$_6$alkyl)$_2$;
—P(O)(—NH-(α-aminoacyl group))(—O-aryl), known as "McGuigan" type prodrugs, for example but not limited to, a compound of Formula I wherein R$^1$ is

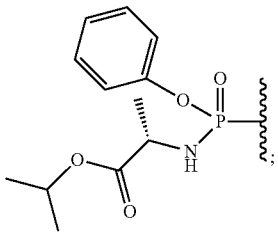 [SMILES: *P(=O)(N[C@@H](C)C(=O)OC(C)C)Oc1ccccc1]

—P(O)(—O—(C$_1$-C$_6$ alkylene)-S-acyl)(—NH-arylalkyl); S-acyl-2-thioethyl (SATE) prodrugs; a cyclic phosphate ester that forms a bridge between two hydroxyl groups, such as:

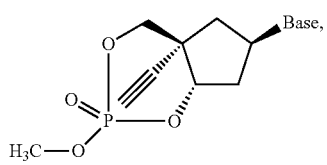

wherein the cyclic phosphate ester forms a bridge between the 3'-OH group and 5'-OH groups; and those described in U.S. Pat. No. 7,879,815; International Publication Nos. WO2005/003047, WO2008/082602, WO2010/0081628, WO2010/075517 and WO2010/075549; Mehellou, *Chem. Med. Chem.*, 5:1841-1842 (2005); Bobeck et al., Antiviral Therapy 15:935-950 (2010); Furman et al., Future Medicinal Chemistry, 1:1429-1452 (2009); and Erion, *Microsomes and Drug Oxidations, Proceedings of the International Symposium*, 17th, Saratoga Springs, N.Y., United States, Jul. 6-10, 2008, 7-12 (2008).

Prodrug modification of the compounds of Formula I at positions other than the 5'-alcohol-derived prodrugs are also contemplated herein. When the compound contains, for example, a hydroxy group, the prodrug can be a derivative of the hydroxy group such as an ester (—OC(O)R), a carbonate ester (—OC(O)OR), a phosphate ester (—O—P(=O)(OH)$_2$), an ether (—OR), or a mono-phosphate prodrug such as a phosphoramidate (can be converted in vivo to the corresponding nucleoside monophosphate). Additionally, if a compound of Formula I contains an alcohol functional group, a prodrug can be formed by the replacement of one or more of the hydrogen atoms of the alcohol groups with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$)alkoxycarbonylaminomethyl, succinoyl, (C$_1$-C$_6$)alkanoyl, α-amino(C$_1$-C$_4$)alkyl, α-amino(C$_1$-C$_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If the compound fo Formula I incorporates an amine functional group, a prodrug can be formed by the replacement of a hydrogen atom in the amine group with a group such as, for example, R-carbonyl-, RO-carbonyl-, NRR'-carbonyl- wherein R and R' are each independently (C$_1$-C$_{10}$) alkyl, (C$_3$-C$_7$) cycloalkyl, benzyl, a natural α-aminoacyl, —C(OH)C(O)OY$^1$ wherein Y$^1$ is H, (C$_1$-C$_6$)alkyl or benzyl, —C(OY$^2$)Y$^3$ wherein Y$^2$ is (C$_1$-C$_4$) alkyl and Y$^3$ is (C$_1$-C$_6$) alkyl; carboxy (C$_1$-C$_6$)alkyl; amino(C$_1$-C$_4$)alkyl or mono-N— or di-N,N—(C$_1$-C$_6$)alkylaminoalkyl; —C(Y$^4$)Y$^5$ wherein Y$^4$ is H or methyl and Y$^5$ is mono-N— or di-N, N—(C$_1$-C$_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aryl (e.g., benzyl), aryloxyalkyl (for example, phenoxymethyl), aryl (e.g., phenyl optionally substituted with, for example, halogen, C$_{1-4}$alkyl, —O—(C$_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a C$_{1-20}$ alcohol or reactive derivative thereof, or by a 2,3-di-(C$_{6-24}$)acyl glycerol.

Other examples include the following: when the compound of Formula I contains a carboxylic acid group, the prodrug can be an ester or an amide, and when the compound of Formula I contains a primary amino group or another suitable nitrogen that can be derivatized, the prodrug can be an amide, carbamate, urea, imine, or a Mannich base. Conventional procedures for the selection and preparation of suitable prodrug derivatives are described, for example, in *Design of Prodrugs*, edited by H. Bundgaard, Elsevier, 1985; J. J. Hale et al., *J. Med. Chem.* 2000, vol. 43, pp. 1234-1241; C. S. Larsen and J. Ostergaard, "Design and application of prodrugs" in: *Textbook of Drug Design and Discovery*, 3$^{rd}$ edition, edited by C. S. Larsen, 2002, pp. 410-458; and Beaumont et al., *Current Drug Metabolism*

2003, vol. 4, pp. 461-458; the disclosures of each of which are incorporated herein by reference in their entireties.

The invention also encompasses methods for the treatment or prophylaxis of infection by HIV, for the inhibition of HIV reverse transcriptase, for the treatment, prophylaxis, or delay in the onset of AIDS in a subject in need thereof, which comprises administering to the subject an effective amount of a compound of the invention or a pharmaceutically acceptable salt thereof.

The invention also encompasses a compound of the invention, or a pharmaceutically acceptable salt thereof, for use in the preparation of a medicament for the treatment or prophylaxis of infection by HIV, for the inhibition of HIV reverse transcriptase, or for the treatment, prophylaxis, or delay in the onset of AIDS in a subject in need thereof.

The invention also encompasses a pharmaceutical composition comprising an effective amount of a compound of the invention, or a pharmaceutically acceptable salt thereof, and a pharmaceutically acceptable carrier and further comprising an effective amount of an additional anti-HIV agent selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

Compounds of Embodiment A are a subset of the compounds included in Formula I. Any description above or which follows that refers to a compound of Formula I also applies to a compound of Embodiment A.

Other embodiments of the present invention include the following:

(a) A pharmaceutical composition comprising an effective amount of a compound of Formula I as defined above, or a prodrug or pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a prodrug or pharmaceutically acceptable salt thereof, and a pharmaceutically acceptable carrier.

(c) The pharmaceutical composition of (a) or (b), further comprising an effective amount of one or more an anti-HIV agents selected from the group consisting of HIV antiviral agents, immunomodulators, and anti-infective agents.

(d) The pharmaceutical composition of (c), wherein the anti-HIV agent is selected from one or more of an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

(e) A combination which is (i) a compound of Formula I as defined above, or a prodrug or pharmaceutically acceptable salt thereof, and (ii) an anti-HIV agent selected from the group consisting of HIV antiviral agents, immunomodulators, and anti-infective agents; wherein the compound and the anti-HIV agent are each employed in an amount that renders the combination effective for inhibition of HIV reverse transcriptase, for treatment or prophylaxis of infection by HIV, or for treatment, prophylaxis of, or delay in the onset or progression of AIDS.

(f) The combination of (e), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

(g) A method for the inhibition of HIV reverse transcriptase in a subject in need thereof which comprises administering to the subject an effective amount of a compound of Formula I or a prodrug or pharmaceutically acceptable salt thereof.

(h) A method for the prophylaxis or treatment of infection by HIV (e.g., HIV-1) in a subject in need thereof which comprises administering to the subject an effective amount of a compound of Formula I or a prodrug or pharmaceutically acceptable salt thereof.

(i) The method of (h), wherein the compound of Formula I is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(j) A method for the prophylaxis, treatment or delay in the onset or progression of AIDS in a subject in need thereof which comprises administering to the subject an effective amount of a compound of Formula I or a prodrug or pharmaceutically acceptable salt thereof.

(k) The method of (j), wherein the compound is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I or pharmaceutically acceptable salt thereof, (i) for use in, (ii) for use as a medicament for, or (iii) for use in the preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments, aspects, classes, sub-classes, or features described above. In all of these embodiments etc., the compound may optionally be used in the form of a prodrug or pharmaceutically acceptable salt or pharmaceutically acceptable salt of a prodrug.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its prodrug or salt and a pharmaceutically acceptable carrier and optionally one or more excipients, it is understood that the term "substantially pure" is in reference to a compound of Formula I or its prodrug and/or salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 fusion inhibitors and HIV-1 entry inhibitors. The compounds of Formula I may also be useful agents against HIV-2.

The term "administration" and variants thereof (e.g., "administering" a compound) in reference to a compound of Formula I means providing the compound to the individual in need of treatment or prophylaxis and includes both self-administration and administration to the patient by another person. When a compound or a prodrug thereof is provided in combination with one or more other active agents (e.g., antiviral agents useful for treating or prophylaxis of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof. By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who is the object of treatment, observation or experiment.

The term "effective amount" as used herein means an amount sufficient to inhibit HIV reverse transcriptase, inhibit HIV replication, exert a prophylactic effect, and/or a exert a therapeutic effect after administration. One embodiment of "effective amount" is a "therapeutically effective amount" which is an amount of a compound that is effective for inhibiting HIV reverse transcriptase, inhibiting HIV replication (either of the foregoing which may also be referred to herein as an "inhibition effective amount"), treating HIV infection, treating AIDS, delaying the onset of AIDS, and/or slowing progression of AIDS in a patient. Another embodiment of "effective amount" is a "prophylactically effective amount" which is an amount of the compound that is effective for prophylaxis of HIV infection or prophylaxis of AIDS in a patient. It is understood that an effective amount can simultaneously be both a therapeutically effective amount, e.g., for treatment of HIV infection, and a prophylactically effective amount, e.g., for prevention or reduction of risk for developing AIDS. When the compound of Formula I is administered as a salt, reference to an amount of the compound is to the free form (i.e., the non-salt form) of the compound.

In the method of the present invention (i.e., inhibiting HIV reverse transcriptase, treating or prophylaxis of HIV infection, inhibiting HIV replication, treating or prophylaxis of AIDS, delaying the onset of AIDS, or delaying or slowing progression of AIDS), the compounds of this invention, optionally in the form of a salt, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles, any of which administration methods can be provided as a single dose, once-daily, or less frequently such as once weekly or once monthly in, for example but not limited to, the dosage ranges and amounts described below. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, $18^{th}$ edition, edited by A. R. Gennaro, Mack Publishing Co., 1990 and in *Remington—The Science and Practice of Pharmacy*, 22nd Edition, published by Pharmaceutical Press and Philadelphia College of Pharmacy at University of the Sciences, 2012, ISBN 978 0 85711-062-6 and prior editions.

Formulations of compounds described by Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are well known in the art. For example, solid dispersions can be prepared using excipients and processes as described in reviews (e.g., A. T. M. Serajuddin, J Pharm Sci, 88:10, pp. 1058-1066 (1999)). Nanoparticulate systems based on both attrition and direct synthesis have also been described in reviews such as Wu et al (F. Kesisoglou, S. Panmai, Y. Wu, Advanced Drug Delivery Reviews, 59:7 pp. 631-644 (2007)).

The compounds of Formula I, and pharmaceutically acceptable salts thereof, are HIV reverse transcriptase inhibitors. The compounds are useful for inhibiting HIV reverse transcriptase and for inhibiting HIV replication in vitro and in vivo. More particularly, the compounds of Formula I inhibit the polymerase function of HIV-1 reverse transcriptase. The testing of compounds of the Examples of the invention in the assay set forth in the RT Polymerase Assay below, illustrates the ability of compounds of the invention to inhibit the RNA-dependent DNA polymerase activity of HIV-1 reverse transcriptase. The compounds of Formula I may also be useful agents against HIV-2.

The compounds of Formula I can be administered in a dosage range of 0.001 to 1000 mg/kg of mammal (e.g., human) body weight per day, or at other time intervals as appropriate, in a single dose or in divided doses. One example of a dosage range is 0.01 to 500 mg/kg body weight per day, or at other time intervals as appropriate, administered orally or via other routes of administration in a single dose or in divided doses. Another example of a dosage range is 0.1 to 100 mg/kg body weight per day, or at other time intervals as appropriate, administered orally or via other routes of administration in single or divided doses. For oral (e.g., tablets or capsules) or other routes of administration, the compositions can be provided containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given dose. Compounds of the invention can be administered as a single dose, once-daily, or less frequently such as once weekly or once monthly in, for example but not limited to, the dosage ranges and amounts noted above. Furthermore, the compound may be formulated for immediate or modified release such as extended or controlled release.

As noted above, the present invention is also directed to use of a compound of Formula I with one or more anti-HIV agents. An "anti-HIV agent" is any agent which is directly or indirectly effective in the inhibition of HIV, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, abacavir sulfate, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| doravirine, MK-1439 | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| Elvitegravir | InI |
| emtricitabine, FTC, Emtriva ® | nRTI |
| emtricitabine + tenofovir DF, Truvada ® | nRTI |
| emivirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| Rilpivirine | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| Tenofovir alafenamide fumarate | nRTI |
| tipranavir, Aptivus ® | PI |
| vicriviroc | EI | or a pharmaceutically acceptable salt thereof.
EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the Physicians' Desk Reference, Thomson PDR, Thomson PDR, 57th edition (2003), the 58th edition (2004), or the 59th edition (2005) and the current Physicians' Desk Reference (68th ed.). (2014), Montvale, N.J.: PDR Network. The dosage ranges for a compound of the invention in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV reverse transcriptase, e.g., by competitive inhibition.

The invention is illustrated by the following examples. For all of the examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

The following abbreviations and acronyms are used herein:

| | |
|---|---|
| Ac | acetyl |
| Ac₂O | acetic anhydride |
| ACN | acetonitrile |
| AcOH | acetic acid |
| HOAc | |
| APCI | atmospheric-pressure chemical ionization |
| aq | aqueous |
| Bn | benzyl |
| Bz | benzoyl |
| Boc, BOC | tert-butoxycarbonyl |
| Cbz | benzyloxycarbonyl |
| calc'd | calculated |
| Celite | diatomaceous earth |
| DBU | 1,8-diazabicyclo(5.4.0)undec-7-ene |
| DCM | dichloromethane |
| DIEA, DIPEA | N,N-diisopropylethylamine |
| DMAP | 4-dimethylaminopyridine |
| DMF | N,N-dimethylformamide |
| DMSO | dimethyl sulfoxide |
| dMTrCl | 4,4'-dimethoxytrityl chloride |
| EDCI | 1-ethyl-3-(3-dimethylaminopropyl)carbodiimide |
| EDTA | ethylenediamine tetraacetic acid |
| ESI | electrospray ionization |
| Et | ethyl |
| Et₂O | diethyl ether |
| EtOH | ethanol |
| EtOAc | ethyl acetate |
| Et₃N | triethylamine |
| h | hour |
| HPLC | high-performance liquid chromatography |
| IPA | isopropanol |
| iPr | isopropyl |
| LC | liquid chromatography |
| LCMS | liquid chromatography mass spectrometry |
| Me | Methyl |
| MeCN | acetonitrile |
| MeOH | methanol |
| mg | milligrams |
| min | minutes |
| μL | microliters |
| mL | milliliters |
| mmol | millimoles |
| MS | mass spectrometry |
| MTBE | methyl tert-butyl ether |
| PDA | photodiode array |
| NMR | nuclear magnetic resonance spectroscopy |
| PE | petroleum ether |

-continued

| | |
|---|---|
| Ph | phenyl |
| Rac | racemic mixture |
| RT or rt | room temperature |
| Rt | retention time |
| Sat | saturated |
| SFC | supercritical fluid chromatography |
| TBAF | tert-butyl ammonium fluoride |
| TBSTBDMS | tert-butyldimethylsilyl |
| TBSCl | tert-butyldimethylsilyl chloride |
| t-Bu | tert-butyl |
| TEA | triethylamine |
| TBDPS | tert-butyldiphenylsilyl |
| TBDPSCl | tert-butyldiphenylsilyl chloride |
| TFA | trifluoroacetic acid |
| THF | tetrahydrofuran |
| TLC | thin layer chromatography |
| TMS | Trimethylsilyl |
| Pr | Propyl |
| PS | Polystyrene |
| MTS | (3-(4,5-dimethylthiazol-2-yl)-5-(3-carboxymethoxyphenyl)-2-(4-sulfophenyl)-2H-tetrazolium) |
| Tris | tris(hydroxymethyl)amino-methane |
| UPLC | ultra-performance liquid chromatography |

General Procedures

Reactions sensitive to moisture or air were performed under nitrogen or argon atmosphere using anhydrous solvents and reagents. The progress of reactions was determined using either analytical thin layer chromatography (TLC) usually performed with E. Merck pre-coated TLC plates, silica gel 60F-254, layer thickness 0.25 mm or liquid chromatography-mass spectrometry (LC-MS).

The analytical UPLC-MS system used consisted of a Waters SQD2 platform with electrospray ionization in positive and negative detection mode with an Acquity UPLC I-class solvent manager, column manager, sample manager and PDA detector. The column used for standard methods was a CORTECS UPLC C18 1.6 μm, 2.1×30 mm, and the column used for polars method was an ACQUITY UPLC HSST3 1.8 μm, 2.1×30 mm, the column temperature was 40° C., the flow rate was 0.7 mL/min, and injection volume was 1 μL. UV detection was in the range 210-400 nm. The mobile phase consisted of solvent A (water plus 0.05% formic acid) and solvent B (acetonitrile plus 0.05% formic acid) with different gradients for 4 different methods: 1/Starting with 99% solvent A for 0.2 minutes changing to 98% solvent B over 1 minutes, maintained for 0.4 minutes, then reverting to 99% solvent A over 0.1 min; 2/Starting with 99% solvent A for 0.5 minutes changing to 98% solvent B over 3.7 minutes, maintained for 0.4 minutes, then reverting to 99% solvent A over 0.1 min; 3/Starting with 100% solvent A for 0.4 minutes changing to 98% solvent B over 0.9 minutes, maintained for 0.3 minutes, then reverting to 100% solvent A over 0.1 min; 4/Starting with 100% solvent A for 0.8 minutes changing to 98% solvent B over 3.4 minutes, maintained for 0.4 minutes, then reverting to 100% solvent A over 0.1 minutes.

The analytical LC-MS system used consisted of a Agilent 6140 quadrupole LC/MS platform with electrospray ionization in positive and negative detection mode with an Agilent 1200 Series solvent manager, column manager, sample manager and PDA detector. The column for standard method was Purospher® STAR RP-18 endcapped 2 μm, Hibar® HR 50-2.1, the column temperature was 60° C., the flow rate was 0.8 mL/min, and injection volume was 0.5-5 L. UV detection was in the range 210-400 nm. The mobile phase consisted of solvent A (water plus 0.05% formic acid) and solvent B (acetonitrile plus 0.05% formic acid) with different gradients for 2 different methods: 1) Starting with 98% solvent A changing to 100% solvent B over 1.8 minutes, maintained for 0.8 min; 2) Starting with 98% solvent A changing to 100% solvent B over 5.8 minutes, maintained for 0.3 minutes.

Preparative HPLC purifications were usually performed using a mass spectrometry directed system. Usually they were performed on a Waters Chromatography Workstation (MassLynx V4.1) configured with LC-MS System Consisting of: Waters ZQ™ 2000 (quad MS system with Electrospray Ionization), Waters 2545 Gradient Pump, Waters 2767 Injecto/Collector, Waters 2998 PDA Detector, the MS Conditions of: 100-1400 amu, Positive Electrospray, Collection Triggered by MS, and a Waters SUNFIRE® C-18 5 micron, 19 mm (id)×150 mm column. The mobile phases consisted of mixtures of acetonitrile (5-95%) in water containing 0.02% formic acid. Flow rates were maintained at 20 mL/min, the injection volume was 500 to 3000 µL, and the UV detection range was 210-400 nm. Mobile phase gradients were optimized for the individual compounds. The analytical system consisted of the same system with a Waters SUNFIRE® C-18 5 µm, 4.6×150 mm column, or a XSelect® CSH™ C-18 5 µm, 4.6×150 mm column. The mobile phases consisted of mixtures of acetonitrile (5-95%) in water containing 0.02% formic acid. Flow rates were maintained at 1.2 mL/min, the injection volume was 5 to 20 µL. Preparative HPLC were also performed on a Gilson system 233XL WITH 735 (Unipoint). The column was a Waters XBridge Prep C18 5 µm OBD, dimension 30×250 mm. The mobile phase consisted of mixture of acetonitrile/ ammonium carbonate 0.02N (3-15% in 70 min or 3-30% in 50 min). Flow rates were maintained at 50 mL/min, the injection volume was 1000 µL, and the UV detection range was 260 nm.

Reactions performed using microwave irradiation were normally carried out using an Emrys Optimizer manufactured by Personal Chemistry, or an Initiator manufactured by Biotage. Concentration of solutions was carried out on a rotary evaporator in vacuo. Flash chromatography was usually performed using a Biotage® Flash Chromatography apparatus (Isolera) on silica gel (15-45µ, 40-63µ, or spheric silica) in pre-packed cartridges of the size noted. $^1$H NMR spectra were acquired at 400 MHz or 500 MHz spectrometers in $CDCl_3$ solutions unless otherwise noted. Chemical shifts were reported in parts per million (ppm). Tetramethylsilane (TMS) was used as internal reference in $CDCl_3$ solutions, and residual $CH_3OH$ peak or TMS was used as internal reference in $CD_3OD$ solutions. Coupling constants (J) were reported in hertz (Hz). Chiral analytical chromatography was performed on one of CHIRALPAK® AS, CHIRALPAK® AD, CHIRALCEL® OD, CHIRALCEL® IA, or CHIRALCEL® OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of of CHIRALPAK AS, of CHIRALPAK AD, CHIRALCEL OD, CHIRALCEL® IA, CHIRALCEL® OJ columns (20×250 mm) (Daicel Chemical Industries, Ltd.) with desired isocratic solvent systems identified on chiral analytical chromatography or by supercritical fluid (SFC) conditions.

Preparation of Compounds

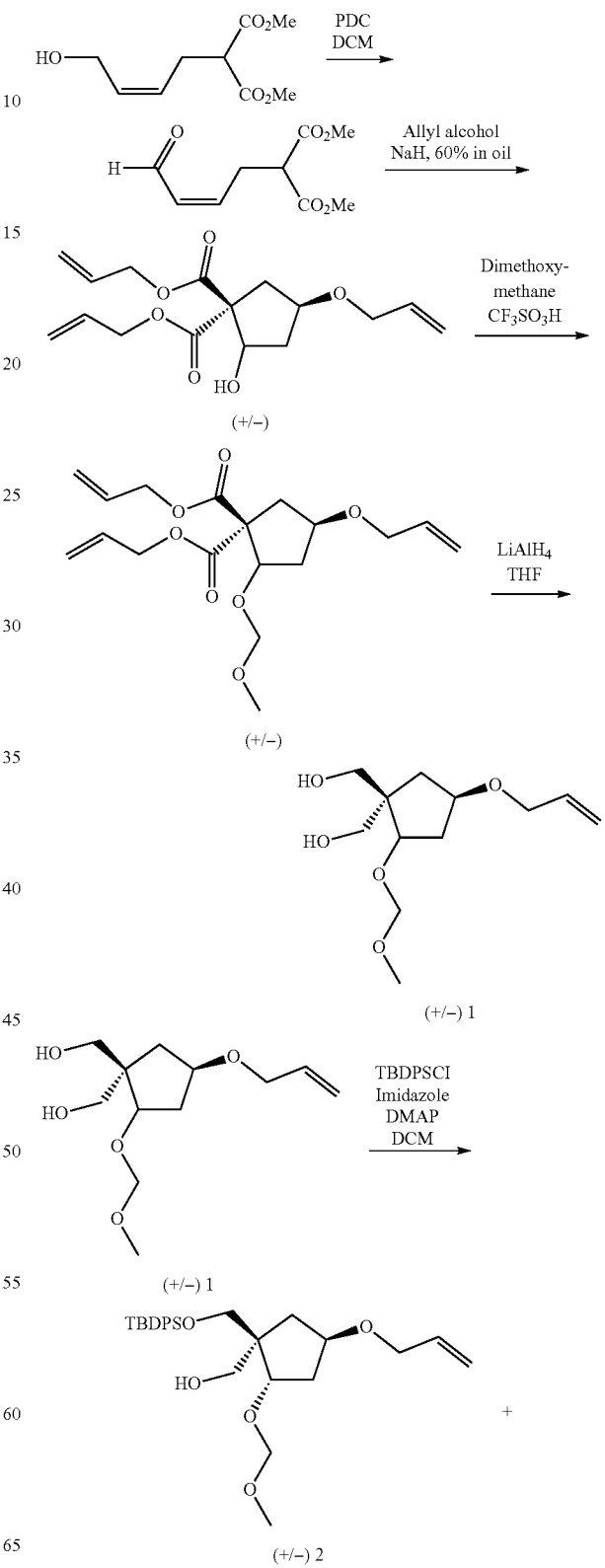

Scheme 1. Synthesis of Intermediate (+/-)7

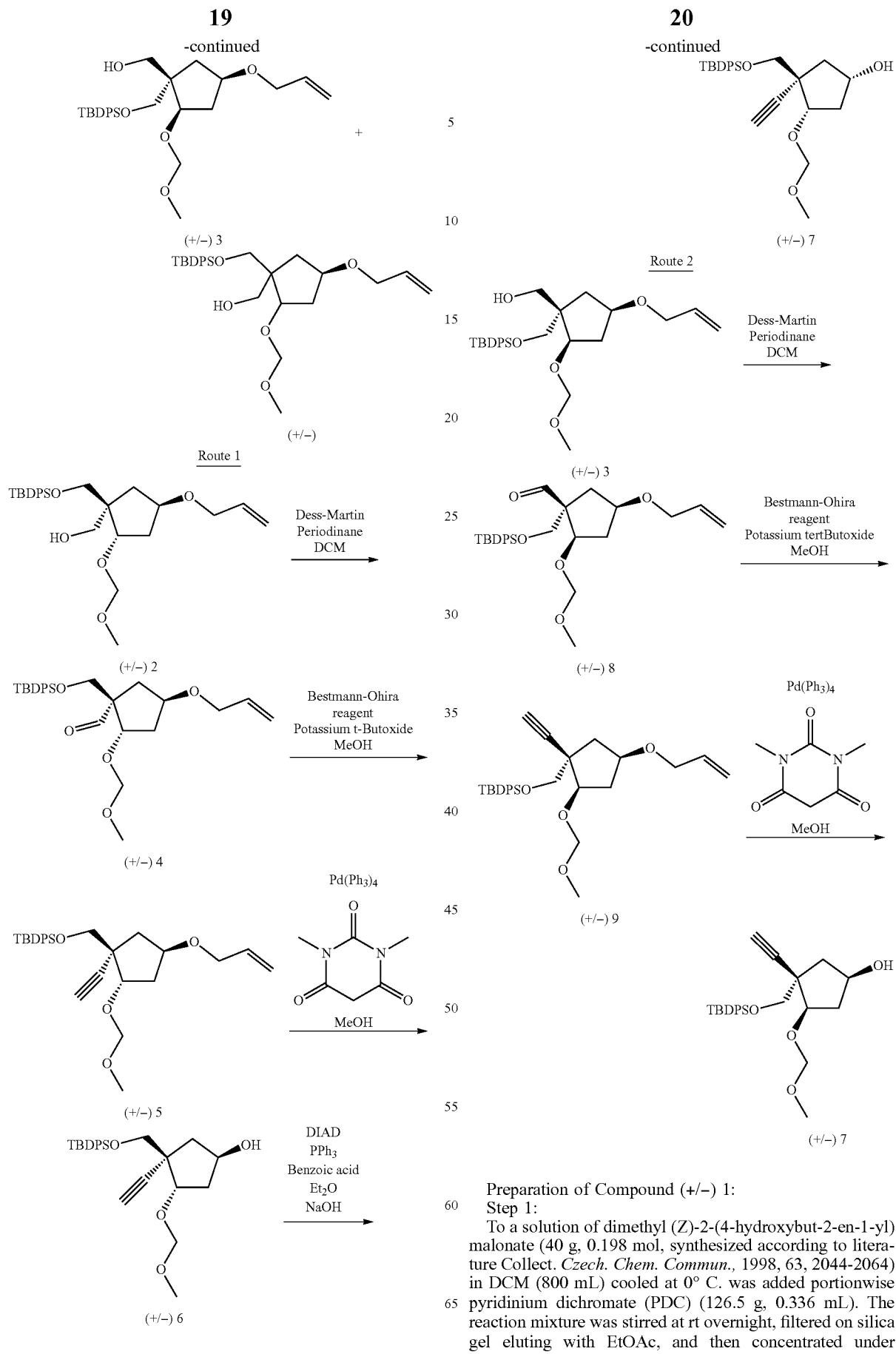
Preparation of Compound (+/−) 1:
Step 1:
To a solution of dimethyl (Z)-2-(4-hydroxybut-2-en-1-yl) malonate (40 g, 0.198 mol, synthesized according to literature Collect. *Czech. Chem. Commun.*, 1998, 63, 2044-2064) in DCM (800 mL) cooled at 0° C. was added portionwise pyridinium dichromate (PDC) (126.5 g, 0.336 mL). The reaction mixture was stirred at rt overnight, filtered on silica gel eluting with EtOAc, and then concentrated under reduced pressure. The crude residue was used in the next step without further purification.

Step 2:

To allyl alcohol (700 mL) was slowly added sodium hydride (60% in oil, 5 g, 0.124 mol) at 0° C. The reaction mixture was stirred at rt for 1 hour. To this reaction mixture was added dropwise a solution of intermediate of step 1 (35.4 g, 0.177 mol) in allyl alcohol (190 mL). The reaction mixture was stirred at rt overnight. The reaction was quenched with addition of AcOH until pH=7, and then the reaction mixture was concentrated under reduced pressure. The crude residue was dissolved in EtOAc and water, the organic layer was separated and the aqueous layer was extracted with EtOAc. The combined organic layers were washed with a saturated NaHCO$_3$ solution and brine, dried over Na$_2$SO$_4$, and concentrated under reduced pressure. The crude residue was purified by flash chromatography on silica gel (PE/EtOAc: 0 to 70%) to afford the expected intermediate.

Step 3:

To a solution of previous intermediate (13.7 g, 44 mmol) in dimethoxymethane (560 mL) was added dropwise triflic acid (3.1 mL, 35 mmol). The reaction mixture was stirred at rt for 1 hour, and then, poured into a saturated NaHCO$_3$ solution and extracted twice with DCM. The organic layer was dried over Na$_2$SO$_4$, and concentrated under reduced pressure. The crude residue was purified by flash chromatography on silica gel (PE/EtOAc: 0 to 100%) to afford the expected intermediate.

Step 4:

To a solution of previous intermediate (8.94 g, 25 mmol) in THF (70 mL), cooled at 0° C., was added dropwise LiAlH$_4$ at 0° C. The reaction mixture was stirred at reflux for 1h30, and then, cooled to 0° C., quenched with dropwise addition of water, and diluted with EtOAc. The resulting reaction mixture was filtered on Celite and washed with water and EtOAc. The organic layer was dried, filtered and concentrated under reduced pressure. The crude residue was purified by flash chromatography on silica gel (DCM/MeOH: 0 to 10%) to afford the expected compound as a mixture of isomers. $^1$H NMR (DMSO-d$_6$, 400 MHz) δ (ppm) 5.91-5.81 (m, 1H), 5.24-5.19 (m, 1H), 5.12-5.08 (m, 1H), 4.58-4.51 (m, 3H), 4.17-4.12 (m, 1H), 3.99-3.93 (m, 1.5H), 3.88-3.79 (m, 2.5H), 3.45-3.35 (m, 2H), 3.33-3.24 (m, 2H), 3.23 (s, 3H), 2.30-2.23 (m, 0.2H), 1.95-1.84 (m, 2.4H), 1.79-1.74 (m, 0.2H), 1.65-1.53 (m, 0.4H), 1.40-1.35 (m, 0.8H).

Preparation of Compound (+/−) 7: (1S,3S,4S)-3-(((tert-butyldiphenylsilyl)oxy)methyl)-3-ethynyl-4-(methoxymethoxy)cyclopentan-1-ol and (1R,3R,4R)-3-(((tert-butyldiphenylsilyl)oxy)methyl)-3-ethynyl-4-(methoxymethoxy)cyclopentan-1-ol Step 1:

To a cold (0° C.) solution of Compound (+/−) 1 (5.75 g, 23.35 mmol) in DCM (280 mL) were added imidazole (1.91 g, 28.0 mmol), DMAP (0.28 g, 2.33 mmol) and tertbutyldiphenylchlorosilane (7.28 mL, 28.0 mmol). The reaction mixture was stirred from 0° C. to rt for 3h and at rt overnight. The reaction mixture was then diluted with ethyl acetate (500 mL), and washed with a 1M HCl solution (500 mL), water (500 mL) and brine (500 mL). The organic layer was dried over sodium sulfate, filtered and concentrated under reduced pressure. The crude residue was purified by column chromatography on silica gel (PE/Et$_2$O: 0 to 70%) to afford the expected compounds (+/−) 2, (+/−) 3 and a mixture of other isomers.

Compound (+/−) 2: $^1$H NMR (DMSO-d$_6$, 400 MHz) δ (ppm) 7.66-7.61 (m, 4H), 7.48-7.40 (m, 6H), 5.87-5.77 (m, 1H), 5.20-5.15 (m, 1H), 5.09-5.05 (m, 1H), 4.55 (d, J=6.62 Hz, 1H), 4.53 (d, J=6.62 Hz, 1H), 4.29 (t, J=4.97 Hz, 1H), 4.14 (t, J=6.55 Hz, 1H), 3.99-3.93 (m, 1H), 3.84-3.82 (m, 2H), 3.62-3.52 (m, 2H), 3.53-3.43 (m, 2H), 3.21 (s, 3H), 1.99-1.85 (m, 3H), 1.53-1.49 (m, 1H), 1.01 (s, 9H); MS (ESI) m/z=507.8 (MNa+). Compound (+/−) 3: $^1$H NMR (DMSO-d$_6$, 400 MHz) δ (ppm) 7.68-7.60 (m, 4H), 7.49-7.41 (m, 6H), 5.91-5.82 (m, 1H), 5.25-5.20 (m, 1H), 5.13-5.09 (m, 1H), 4.55 (d, J=6.62 Hz, 1H), 4.50 (d, J=6.62 Hz, 1H), 4.26 (t, J=4.95 Hz, 1H), 4.04-3.99 (m, 1H), 3.88-3.78 (m, 3H), 3.49-3.48 (m, 4H), 3.21 (s, 3H), 2.31-2.24 (m, 1H), 1.95-1.86 (m, 1H), 1.68-1.60 (m, 2H), 1.01 (s, 9H); MS (ESI) m/z=507.6 (MNa+).

Route 1: beginning with (+/−) 2

Step 2a:

To a solution of Compound (+/−) 2 (2.68 g, 5.53 mmol) in DCM (40 mL) under nitrogen was added Dess-Martin Periodinane (4.69 g, 11.06 mmol) dissolved in DCM (40 mL). The reaction mixture was stirred at rt overnight. The resulting reaction mixture was partially concentrated under reduced pressure (⅔), and the compound was purified by column chromatography on silica gel (PE/Et$_2$O: 0 to 70%) to afford the expected compound (+/−) 4. $^1$H NMR (DMSO-d$_6$, 400 MHz) δ (ppm) 9.66 (s, 1H), 7.61-7.59 (m, 4H), 7.50-7.41 (m, 6H), 5.86-5.76 (m, 1H), 5.20-5.15 (m, 1H), 5.11-5.07 (m, 1H), 4.53 (d, J=6.79 Hz, 1H), 4.50 (d, J=6.79 Hz, 1H), 4.22 (t, J=6.79 Hz, 1H), 4.12 (d, J=9.78 Hz, 1H), 4.06-4.01 (m, 1H), 3.85-3.84 (m, 2H), 3.72 (d, J=9.78 Hz, 1H), 3.17 (s, 3H), 2.44-2.39 (m, 1H), 2.02-1.96 (m, 1H), 1.85-1.78 (m, 1H), 1.70-1.66 (m, 1H), 0.98 (s, 9H); MS (ESI) m/z=505.5 (MNa$^+$).

Step 3a:

To a solution of Compound (+/−) 4 (650 mg, 1.35 mmol) in MeOH (38.5 mL) under nitrogen was added potassium carbonate (558 mg, 4.04 mmol). The reaction mixture was stirred at 0° C. and then, dimethyl (1-diazo-2-oxopropyl) phosphonate (0.40 mL, 2.69 mmol) was added dropwise under nitrogen. The reaction mixture was stirred at RT overnight, and then, concentrated under reduced pressure. The crude residue was purified by flash chromatography on silica gel (PE/Et$_2$O: 0 to 70%) to afford the expected compound (+/−) 5. $^1$H NMR (DMSO-d$_6$, 400 MHz) δ (ppm) 7.66-7.61 (m, 4H), 7.50-7.42 (m, 6H), 5.88-5.79 (m, 1H), 5.22-5.17 (m, 1H), 5.11-5.08 (m, 1H), 4.59 (s, 2H), 4.16 (t, J=7.49 Hz, 1H), 4.08-4.03 (m, 1H), 3.86-3.84 (m, 2H), 3.66 (d, J=9.76 Hz, 1H), 3.60 (d, J=9.76 Hz, 1H), 3.22 (s, 3H), 3.02 (s, 1H), 2.15-2.10 (m, 1H), 1.99-1.96 (m, 2H), 1.93-1.89 (m, 1H), 1.02 (s, 9H); MS (ESI) m/z=501.5 (MNa+).

Step 4a:

To a solution of Compound (+/−) 5 (323 mg, 0.675 mmol) in MeOH (1.5 mL) were added 1,3-dimethylbarbituric acid (211 mg, 1.35 mmol) and tetrakis(triphenylphosphine)palladium (0) (39.0 mg, 0.034 mmol) at rt. The reaction mixture was stirred at rt overnight, and then, concentrated under reduced pressure and directly purified by flash chromatography on silica gel (PE/Et$_2$O: 0 to 100%) to afford the expected compound (+/−) 6. $^1$H NMR (DMSO-d$_6$, 400 MHz) δ (ppm) 7.67-7.62 (m, 4H), 7.50-7.42 (m, 6H), 4.75-4.74 (m, 1H), 4.60 (d, J=6.69 Hz, 1H), 4.57 (d, J=6.69 Hz, 1H), 4.27-4.25 (m, 1H), 4.19 (t, J=7.40 Hz, 1H), 3.66-3.60 (m, 2H), 3.22 (s, 3H), 2.97 (s, 1H), 2.13-2.08 (m, 1H), 2.01-1.93 (m, 1H), 1.87-1.81 (m, 1H), 1.79-1.75 (m, 1H), 1.02 (s, 9H); MS (ESI) m/z=461.4 (MNa⁺).

Step 5a:

To a suspension of triphenylphosphine (316 mg, 1.20 mmol) in Et20 (8.4 mL) under nitrogen at 0° C. was added diisopropyl azodicarboxylate (DIAD) (0.24 mL, 1.20 mmol). This reaction mixture was stirred at 0° C. for 30 min. To a solution of Compound (+/−) 6 (264 mg, 0.60 mmol) and benzoic acid (147 mg, 1.20 mmol) in Et20 (8.4 mL) at 0° C. was added the previous solution. The reaction mixture was stirred at RT overnight, and then, concentrated under reduced pressure. A solution of 1% NaOH in MeOH (3 mL) was added and the reaction mixture was stirred for 2 h. EtOAc (50 mL) was added followed by a 1M HCl solution (50 mL). The aqueous layer was extracted twice with EtOAc, and the combined organic layer were dried over Na₂SO₄, filtered and concentrated under reduced pressure to afford the title compound (+/−) 7. ¹H NMR (DMSO-d₆, 400 MHz) δ (ppm) 7.64-7.60 (m, 4H), 7.51-7.42 (m, 6H), 4.80-4.74 (m, 1H), 4.60-4.56 (m, 2H), 4.05-3.98 (m, 1H), 3.95-3.92 (m, 1H), 3.57 (d, J=9.92 Hz, 1H), 3.46 (d, J=9.92 Hz, 1H), 3.22 (s, 3H), 2.99 (s, 1H), 2.29-2.18 (m, 2H), 1.77-1.65 (m, 2H), 1.01 (s, 9H); MS (ESI) m/z=461.4 (MNa⁺).

Route 2: beginning with (+/−) 3

Step 2b:

Compound (+/−) 8 was synthesized according to a similar procedure than described for compound (+/−) 4 starting from compound (+/−) 3. ¹H NMR (DMSO-d₆, 400 MHz) δ (ppm) 9.70 (s, 1H), 7.60-7.58 (m, 4H), 7.51-7.44 (m, 6H), 5.92-5.83 (m, 1H), 5.26-5.21 (m, 1H), 5.14-5.11 (m, 1H), 4.54 (d, J=6.72 Hz, 1H), 4.47 (d, J=6.72 Hz, 1H), 4.15 (t, J=6.84 Hz, 1H), 3.91-3.86 (m, 4H), 3.64 (d, J=10.22 Hz, 1H), 3.16 (s, 3H), 2.35-2.28 (m, 1H), 2.10-1.97 (m, 2H), 1.72-1.65 (m, 1H), 0.99 (s, 9H); MS (ESI) m/z=505.8 (MNa⁺).

Step 3b:

Compound (+/−) 9 was synthesized according to a similar procedure described for compound (+/−) 5 starting from compound (+/−) 8. ¹H NMR (DMSO-d₆, 400 MHz) δ (ppm) 7.70-7.60 (m, 4H), 7.50-7.43 (m, 6H), 5.91-5.82 (m, 1H), 5.27-5.21 (m, 1H), 5.13-5.09 (m, 1H), 4.60 (d, J=6.74 Hz, 1H), 4.57 (d, J=6.74 Hz, 1H), 3.97-3.93 (m, 1H), 3.88-3.84 (m, 3H), 3.59 (d, J=9.80 Hz, 1H), 3.49 (d, J=9.80 Hz, 1H), 3.22 (s, 3H), 2.99 (s, 1H), 2.39-2.29 (m, 1H), 2.27-2.21 (m, 1H), 1.85-1.72 (m, 2H), 1.02 (s, 9H); MS (ESI) m/z=501.9 (MNa⁺).

Step 4b:

Compound (+/−) 7 was synthesized according to a similar procedure described for compound (+/−) 6 starting from compound (+/−) 9.

Example 13

Scheme 2. Synthesis of (+/−) 13 and (+/−) 14 from (+/−) 7.

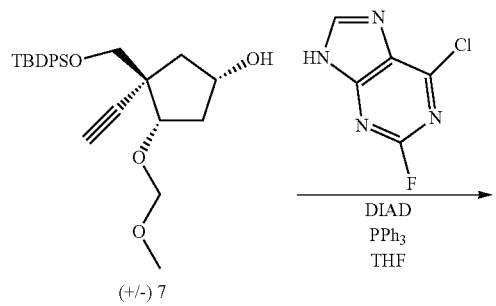

Step 1:

To a suspension of triphenylphosphine (474 mg, 1.81 mmol) in THF (10 mL) under nitrogen at 0° C. was added diisopropyl azodicarboxylate (0.33 mL, 1.69 mmol). This reaction mixture was stirred at 0° C. for 30 min. To a solution of Compound (+/−) 7 (264 mg, 0.60 mmol) and 6-chloro-2-fluoropurine (156 mg, 0.90 mmol) in THF (10 mL) at −41° C. was added the previous solution. The reaction mixture was stirred at −41° C. for 2 h and at rt overnight, and then, concentrated under reduced pressure. The crude residue was purified by column chromatography on silica gel (DCM/MeOH: 0 to 10%) to afford the expected compound (+/−) 10. ¹H NMR (DMSO-d₆, 400 MHz) δ (ppm) 8.78 (s, 1H), 7.66-7.59 (m, 4H), 7.48-7.38 (m, 6H), 5.34-5.25 (m, 1H), 4.66 (d, J=6.70 Hz, 1H), 4.63 (d, J=6.70 Hz, 1H), 4.59 (t, J=7.42 Hz, 1H), 3.77 (d, J=10.05 Hz, 1H), 3.72 (d, J=10.05 Hz, 1H), 3.24 (s, 3H), 3.22 (s, 1H), 2.60-2.52 (m, 2H), 2.40-2.31 (m, 2H), 1.02 (s, 9H); MS (ESI) m/z=593.6 (MH+).

Step 2:

To a solution of compound (+/−) 10 (330 mg, 0.56 mmol) in anhydrous THF (9.28 mL) was added acetic acid (0.16 mL, 2.78 mmol) followed by TBAF (1.11 mL, 1.11 mmol).

The reaction mixture was stirred at rt overnight, and then, concentrated under reduced pressure. The crude residue was purified by column chromatography on silica gel (DCM/MeOH: 0 to 10%) to afford the expected compound (+/−) 11. H NMR (DMSO-d6, 400 MHz) δ (ppm) 8.82 (s, 1H), 5.27-5.19 (m, 2H), 4.69 (d, J=6.68 Hz, 1H), 4.64 (d, J=6.68 Hz, 1H), 4.35 (t, J=7.06 Hz, 1H), 3.60-3.52 (m, 2H), 3.29 (s, 3H), 3.14 (s, 1H), 2.48-2.45 (m, 1H), 2.38-2.26 (m, 3H); $^{19}$F NMR (DMSO-d$_6$, 376 MHz) δ (ppm) −51.82 (s, 1F); MS (ESI) m/z=355.4 (MH$^+$).

Step 3:

To a solution of compound (+/−) 11 (15 mg, 0.042 mmol) in DCM (1.5 mL) was added TFA (0.3 mL, 3.89 mmol). The reaction mixture was stirred at rt for 2 h, and then, concentrated under reduced pressure under $N_2$ flow. The crude residue was purified by column chromatography on silica gel (DCM/MeOH: 0 to 10%) to afford the title compound (+/−) 12. $^1$H NMR (DMSO-d$_6$, 400 MHz) δ (ppm) 8.80 (s, 1H), 5.24-5.16 (m, 1H), 5.08 (brs, 2H), 4.36 (t, J=7.36 Hz, 1H), 3.57-3.52 (m, 2H), 3.07 (s, 1H), 2.40-2.21 (m, 4H); $^{19}$F NMR (DMSO-d$_6$, 376 MHz) δ (ppm) −51.92 (s, 1F); MS (ESI) m/z=311.4 (MH$^+$).

Preparation of Compound (+/−) 13: (1S,2S,4R)-4-(6-amino-2-fluoro-9H-purin-9-yl)-2-ethynyl-2-(hydroxymethyl)cyclopentan-1-ol and (1R,2R,4S)-4-(6-amino-2-fluoro-9H-purin-9-yl)-2-ethynyl-2-(hydroxymethyl)cyclopentan-1-ol, and Compound (+/−) 14: (1S,2S,4R)-4-(2-amino-6-chloro-9H-purin-9-yl)-2-ethynyl-2-(hydroxymethyl)cyclopentan-1-ol and (1R,2R,4S)-4-(2-amino-6-chloro-9H-purin-9-yl)-2-ethynyl-2-(hydroxymethyl)cyclopentan-1-ol A solution of compound (+/−) 12 (138 mg, 0.44 mmol) in 0.5M Ammonia in Dioxane (6 mL, 3 mmol) was cooled at 0° C., and then, ammonia gas was bubbled for 5 min at 0° C. The system was sealed and the reaction mixture was stirred at rt overnight. The reaction mixture was then concentrated under reduced pressure and the crude residue was purified by preparative HPLC to afford the 2 title compounds:

Compound (+/−) 13: $^1$H NMR (DMSO-d$_6$, 400 MHz) δ (ppm) 8.21 (s, 1H), 7.77 (brs, 2H), 5.09-5.01 (m, 3H), 4.33 (t, J=7.61 Hz, 1H), 3.56-3.50 (m, 2H), 3.05 (s, 1H), 2.30-2.14 (m, 4H); $^{19}$F NMR (DMSO-d$_6$, 376 MHz) δ (ppm) −52.10 (s, 1F); MS (ESI) m/z=292.4 (MH$^+$).

Compound (+/−) 14: $^1$H NMR (DMSO-d$_6$, 400 MHz) δ (ppm) 8.27 (s, 1H), 6.93 (brs, 2H), 5.10-5.02 (m, 3H), 4.30 (t, J=7.55 Hz, 1H), 3.56-3.51 (m, 2H), 3.06 (s, 1H), 2.27-2.10 (m, 4H); MS (ESI) m/z=308.3 (MH$^+$).

Example 18

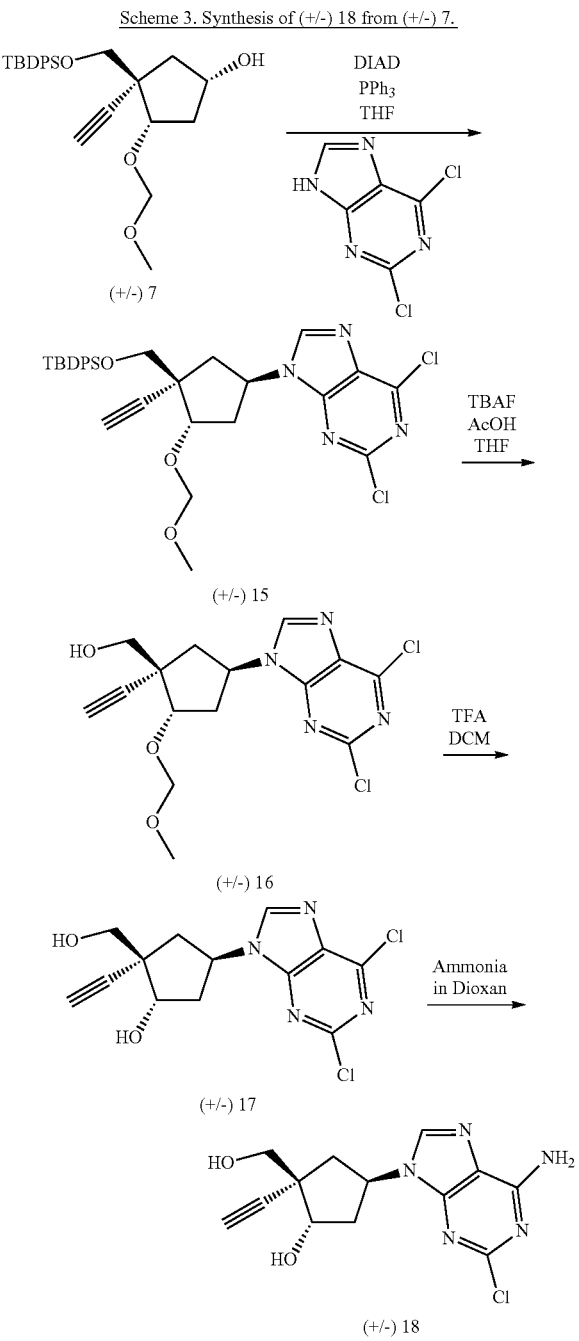

Scheme 3. Synthesis of (+/−) 18 from (+/−) 7.

Preparation of Compound (+/−) 17: (1S,2S,4R)-4-(2,6-dichloro-9H-purin-9-yl)-2-ethynyl-2-(hydroxymethyl)cyclopentan-1-ol and (1R,2R,4S)-4-(2,6-dichloro-9H-purin-9-yl)-2-ethynyl-2-(hydroxymethyl)cyclopentan-1-ol Compound (+/−) 17 was synthesized according to a similar procedure to that described for the synthesis of compound (+/−) 12, starting for step 1 from compound (+/−) 7 and 2,6-dichloro-9H-purine.

Step 1:

Compound (+/−) 15: ¹H NMR (DMSO-d₆, 400 MHz) δ (ppm) 8.83 (s, 1H), 7.66-7.60 (m, 4H), 7.50-7.38 (m, 6H), 5.34-5.26 (m, 1H), 4.68-4.64 (m, 2H), 4.56 (t, J=7.32 Hz, 1H), 3.77 (d, J=9.95 Hz, 1H), 3.73 (d, J=9.95 Hz, 1H), 3.25 (s, 3H), 3.23 (s, 1H), 2.61-2.53 (m, 2H), 2.47-2.32 (m, 2H), 1.02 (s, 9H); MS (ESI) m/z=609.5 (MH⁺).

Step 2:

Compound (+/−) 16: ¹H NMR (DMSO-d₆, 400 MHz) δ (ppm) 8.86 (s, 1H), 5.29-5.20 (m, 2H), 4.69 (d, J=6.67 Hz, 1H), 4.65 (d, J=6.67 Hz, 1H), 4.36 (t, J=7.09 Hz, 1H), 3.60-3.53 (m, 2H), 3.30 (s, 3H), 3.14 (s, 1H), 2.48-2.44 (m, 1H), 2.39-2.32 (m, 3H); MS (ESI) m/z=371.2 (MH⁺).

Step 3:

Compound (+/−) 17: The reaction mixture was stirred at rt for 5 h. ¹H NMR (DMSO-d6, 400 MHz) δ (ppm) 8.85 (s, 1H), 5.26-5.18 (m, 1H), 5.09 (brs, 2H), 4.35 (t, J=7.59 Hz, 1H), 3.55 (brs, 2H), 3.08 (s, 1H), 2.39-2.22 (m, 4H); MS (ESI) m/z=327.1 (MH⁺).

Preparation of Compound (+/−) 18: (1S,2S,4R)-4-(6-amino-2-chloro-9H-purin-9-yl)-2-ethynyl-2-(hydroxymethyl)cyclopentan-1-ol and (1R,2R,4S)-4-(6-amino-2-chloro-9H-purin-9-yl)-2-ethynyl-2-(hydroxymethyl)cyclopentan-1-ol Compound (+/−) 18 was synthesized according to a similar procedure to that described for the synthesis of compound (+/−) 13, starting from compound (+/−) 17.

Compound (+/−) 18: ¹H NMR (DMSO-d₆, 400 MHz) δ (ppm) 8.26 (s, 1H), 7.76 (brs, 2H), 5.12-5.04 (m, 3H), 4.35-4.29 (m, 1H), 3.57-3.53 (m, 2H), 3.05 (s, 1H), 2.29-2.13 (m, 4H); MS (ESI) m/z=308.3 (MH⁺).

The two enantiomers of Compound (+/−) 18 were separated by preparative chiral SFC with the following condition: Column: IA, 2*15 cm, 5 pim; Mobile Phase A: C₀₂; Mobile Phase B: MeOH; Gradient: 45% B in 7 min; Flow rate: 55 mL/min; Detector: UV 220 nm; to afford: Isomer 18A (Faster eluting: Rt=1.43 min; MS (ESI) m/z=308.2 (MH⁺)) and Isomer 18B (Slower eluting: Rt=3.15 min; MS (ESI) m/z=308.2 (MH⁺)).

Example 22

Scheme 4. Synthesis of (+/-) 22 from (+/-) 7.

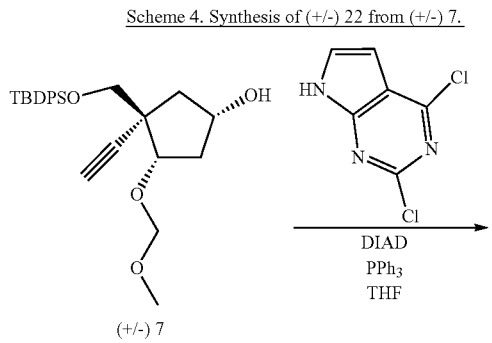

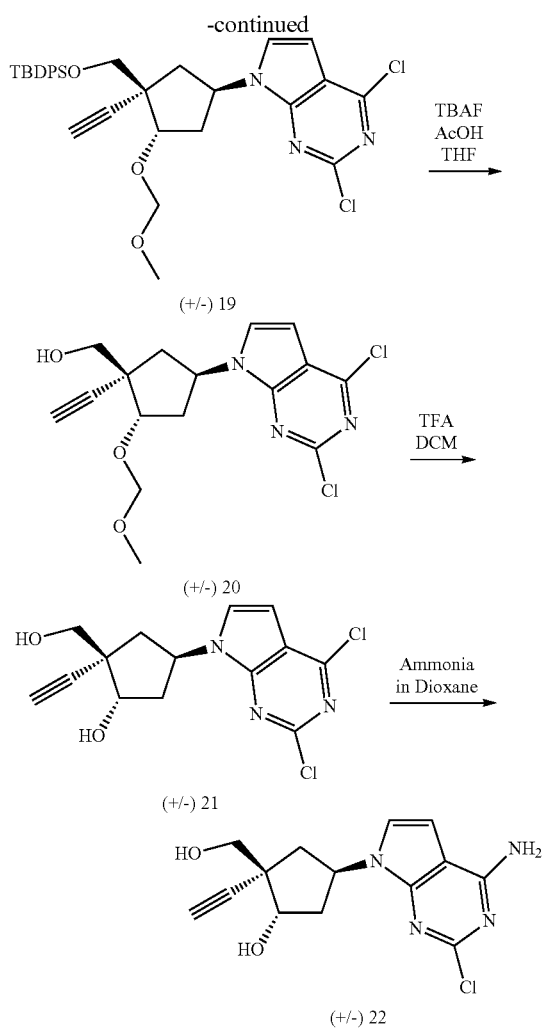

Preparation of Compound (+/−) 21: (1S,2S,4R)-4-(2,4-dichloro-7H-pyrrolo[2,3-d]pyrimidin-7-yl)-2-ethynyl-2-(hydroxymethyl)cyclopentan-1-ol and (1R,2R,4S)-4-(2,4-dichloro-7H-pyrrolo[2,3-d]pyrimidin-7-yl)-2-ethynyl-2-(hydroxmethyl)cyclopentan-1-ol Compound (+/−) 21 was synthesized according to a similar procedure to that described for the synthesis of compound (+/−) 12, beginning with compound (+/−) 7 and 2,4-dichloro-7H-pyrrolo[2,3-d]pyrimidine.

Step 1:

Compound (+/−) 19: ¹H NMR (DMSO-d₆, 400 MHz) δ (ppm) 7.91 (d, J=3.70 Hz, 1H), 7.66-7.61 (m, 4H), 7.50-7.39 (m, 6H), 6.76 (d, J=3.70 Hz, 1H), 5.42-5.34 (m, 1H), 4.69-4.64 (m, 2H), 4.51 (t, J=7.23 Hz, 1H), 3.78 (d, J=9.94 Hz, 1H), 3.74 (d, J=9.94 Hz, 1H), 3.24 (s, 3H), 3.22 (s, 1H), 2.48-2.23 (m, 4H), 1.02 (s, 9H); MS (ESI) m/z=630.5 (MNa⁺).

Step 2:

Compound (+/−) 20: ¹H NMR (DMSO-d₆, 400 MHz) δ (ppm) 7.94 (d, J=3.75 Hz, 1H), 6.76 (d, J=3.75 Hz, 1H), 5.44-5.35 (m, 1H), 5.24 (brs, 1H), 4.69 (d, J=6.61 Hz, 1H), 4.65 (d, J=6.61 Hz, 1H), 4.33 (t, J=7.12 Hz, 1H), 3.59 (d, J=10.84 Hz, 1H), 3.55 (d, J=10.84 Hz, 1H), 3.30 (s, 3H), 3.13 (s, 1H), 2.34-2.16 (m, 4H); MS (ESI) m/z=370.2 (MH⁺).

Step 3:

Compound (+/−) 21: The reaction mixture was stirred at rt for 5 h. $^1$H NMR (DMSO-d6, 400 MHz) δ (ppm) 7.92 (d, J=3.72 Hz, 1H), 6.75 (d, J=3.72 Hz, 1H), 5.41-5.33 (m, 1H), 5.02 (brs, 2H), 4.32 (t, J=7.55 Hz, 1H), 3.57 (d, J=10.78 Hz, 1H), 3.53 (d, J=10.78 Hz, 1H), 3.08 (s, 1H), 2.28-2.09 (m, 4H); MS (ESI) m/z=326.2 (MH$^+$).

Preparation of Compound (+/−) 22: (1S,2S,4R)-4-(4-amino-2-chloro-7H-pyrrolo[2,3-d]pyrimidin-7-yl)-2-ethynyl-2-(hydroxymethyl)cyclopentan-1-ol and (1R,2R,4S)-4-(4-amino-2-chloro-7H-pyrrolo[2,3-d]pyrimidin-7-yl)-2-ethynyl-2-(hydroxymethyl)cyclopentan-1-ol Compound (+/−) 22 was synthesized according to a similar procedure to that described for the synthesis of compound (+/−) 13, starting from compound (+/−) 21. The reaction mixture was stirred for 9 days.

Compound (+/−) 22: $^1$H NMR (DMSO-d$_6$, 400 MHz) δ (ppm) 7.47 (brs, 2H), 7.24 (d, J=3.55 Hz, 1H), 6.57 (d, J=3.55 Hz, 1H), 5.26-5.18 (m, 1H), 5.05-5.02 (m, 2H), 4.26 (t, J=7.51 Hz, 1H), 3.55 (d, J=10.73 Hz, 1H), 3.50 (d, J=10.73 Hz, 1H), 3.04 (s, 1H), 2.21-2.14 (m, 2H), 2.10-2.00 (m, 2H); MS (ESI) m/z=307.3 (MH$^+$).

Example 26

Scheme 5. Synthesis of (+/−) 26 from (+/−) 7.

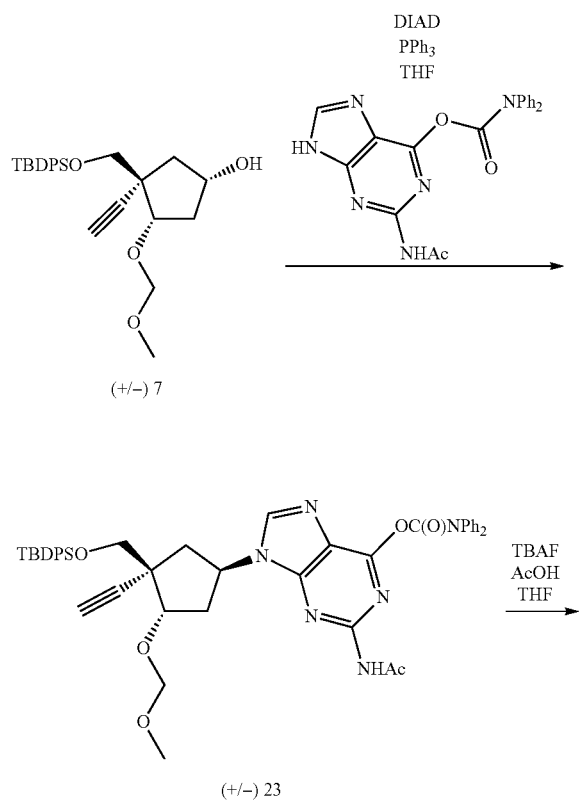

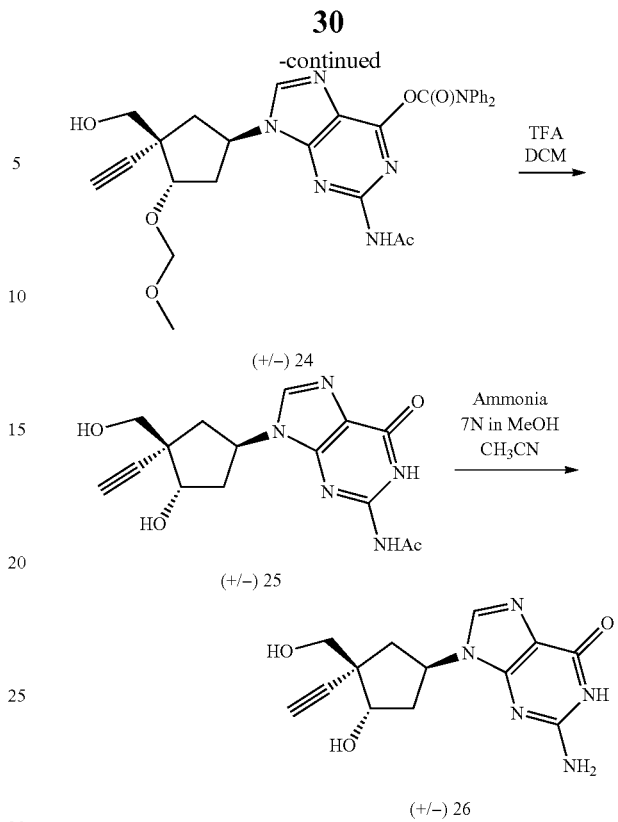

Preparation of Compound (+/−) 26: 2-amino-9-((1R,3S,4S)-3-ethynyl-4-hydroxy-3-(hydroxymethyl)cyclopentyl)-1,9-dihydro-6H-purin-6-one and 2-amino-9-((1S,3R,4R)-3-ethynyl-4-hydroxy-3-(hydroxymethyl)cyclopentyl)-1,9-dihydro-6H-purin-6-one Compound (+/−) 26 was synthesized according to a similar procedure to that described for the synthesis of compound (+/−) 12 for the 3 first steps, beginning with compound (+/−) 7 and 2-acetamido-9H-purin-6-yl diphenylcarbamate.

Step 1:

Compound (+/−) 23: $^1$H NMR (DMSO-d$_6$, 400 MHz) δ (ppm) 10.68 (s, 1H), 8.50 (s, 1H), 7.64-7.30 (m, 20H), 5.27-5.18 (m, 1H), 4.71-4.66 (m, 3H), 3.83 (d, J=9.72 Hz, 1H), 3.77 (d, J=9.72 Hz, 1H), 3.22 (s, 3H), 3.19 (s, 1H), 2.58-2.54 (m, 2H), 2.42-2.32 (m, 2H), 2.13 (s, 3H), 0.98 (s, 9H); MS (ESI) m/z=807.5 (MH$^-$).

Step 2:

Compound (+/−) 24: $^1$H NMR (DMSO-d$_6$, 400 MHz) δ (ppm) 10.70 (s, 1H), 8.54 (s, 1H), 7.50-7.31 (m, 10H), 5.25-5.12 (m, 2H), 4.69 (d, J=6.63 Hz, 1H), 4.64 (d, J=6.63 Hz, 1H), 4.45 (t, J=7.22 Hz, 1H), 3.61-3.54 (m, 2H), 3.28 (s, 3H), 3.11 (s, 1H), 2.46-2.41 (m, 1H), 2.36-2.29 (m, 3H), 2.22 (s, 3H); MS (ESI) m/z=571.7 (MH$^+$).

Step 3:

Compound (+/−) 25: The reaction mixture was stirred at rt overnight. $^1$H NMR (DMSO-d$_6$, 400 MHz) δ (ppm) 12.01 (s, 1H), 11.68 (s, 1H), 8.15 (s, 1H), 5.10-5.03 (m, 3H), 4.31-4.27 (m, 1H), 3.54 (brs, 2H), 3.08 (s, 1H), 2.29-2.21 (m, 2H), 2.11-2.06 (m, 2H), 2.22 (s, 3H); MS (ESI) m/z=332.3 (MH$^+$).

Step 4:

Compound (+/−) 26: To a solution of compound (+/−) 25 (137 mg, 0.41 mmol) in CH$_3$CN (2 mL) was added a 7N Ammonia solution in MeOH (2.9 mL, 21 mmol). The reaction mixture was stirred at rt overnight. After a further addition of 7N Ammonia solution in MeOH (2.9 mL, 21 mmol), the reaction mixture was stirred at 50° C. overnight. The reaction mixture was then concentrated under reduced pressure and the crude residue was triturated in a mixture water/CH$_3$CN (1:1), filtered and washed with water/CH$_3$CN (1:1), CH$_3$CN and pentane to afford the title compound. $^1$H NMR (DMSO-d$_6$, 400 MHz) δ (ppm) 10.55 (s, 1H), 7.81 (s, 1H), 6.44 (brs, 2H), 5.01 (t, J=5.82 Hz, 1H), 4.98-4.91 (m, 2H), 4.29-4.24 (m, 1H), 3.56-3.48 (m, 2H), 3.04 (s, 1H), 2.22-2.11 (m, 3H), 2.08-2.02 (m, 1H); MS (ESI) m/z=290.4 (MH$^+$).

The two enantiomers of Compound (+/−) 26 were separated by preparative chiral SFC with the following condition: Column: OD-H, 2*25 cm, 5 m; Mobile Phase A: CO$_2$; Mobile Phase B: MeOH; Gradient: 30% B in 6 min; Flow rate: 60 mL/min; Detector: UV 254 nm; to afford: Isomer 26A (Faster eluting: Rt=1.76 min; MS (ESI) m/z=290.2 (MH$^+$)) and Isomer 26B (Slower eluting: Rt=2.22 min; MS (ESI) m/z=290.2 (MH$^+$)).

Example 30

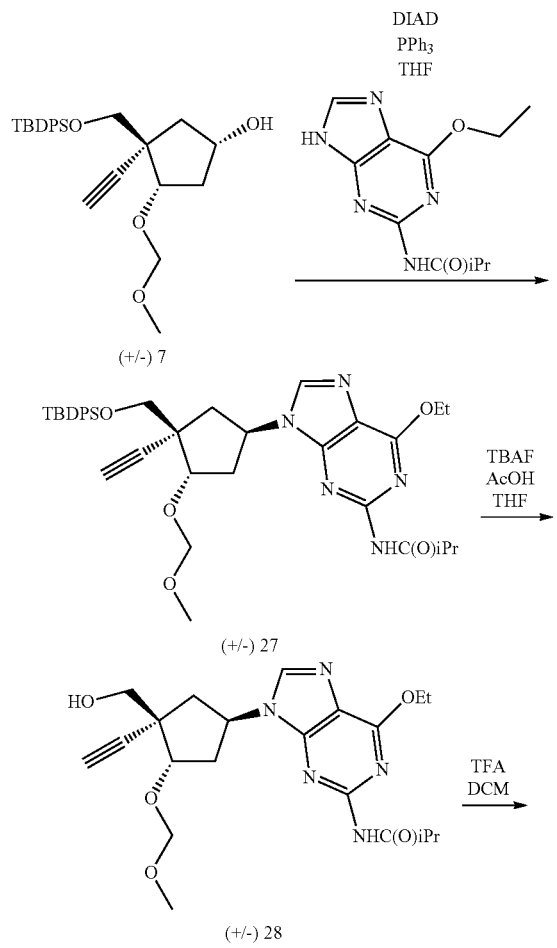

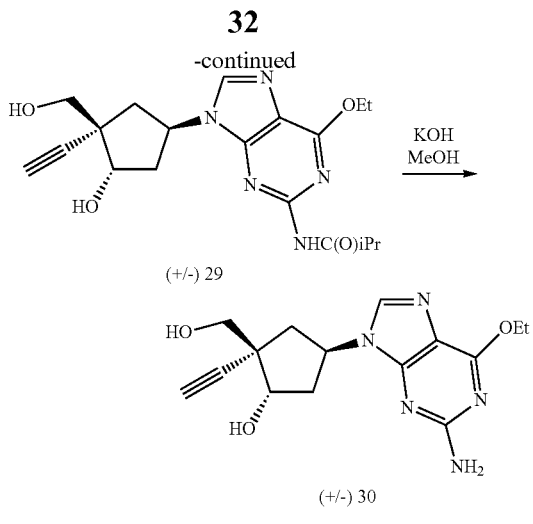

Preparation of Compound (+/−) 30: (1S,2S,4R)-4-(2-amino-6-ethoxy-9H-purin-9-yl)-2-ethynyl-2-(hydroxymethyl)cyclopentan-1-ol and (1R,2R,4S)-4-(2-amino-6-ethoxy-9H-purin-9-yl)-2-ethynyl-2-(hydroxymethyl)cyclopentan-1-ol Compound (+/−) 30 was synthesized according to a similar procedure to that described for the synthesis of compound (+/−) 12 for the 3 first steps, beginning with compound (+/−) 7 and N-(6-ethoxy-9H-purin-2-yl)isobutyramide.

Step 1:

Compound (+/−) 27: MS (ESI) m/z=670.4 (MH$^+$).

Step 2:

Compound (+/−) 28: $^1$H NMR (DMSO-d$_6$, 400 MHz) δ (ppm) 10.31 (s, 1H), 8.32 (s, 1H), 5.21-5.13 (m, 1H), 5.10 (t, J=5.96 Hz, 1H), 4.69 (d, J=6.62 Hz, 1H), 4.65 (d, J=6.62 Hz, 1H), 4.57 (q, J=7.06 Hz, 2H), 4.45 (t, J=7.06 Hz, 1H), 3.62-3.54 (m, 2H), 3.28 (s, 3H), 3.10 (s, 1H), 2.98-2.91 (m, 1H), 2.41-2.22 (m, 4H), 1.40 (t, J=7.06 Hz, 3H), 1.09 (d, J=6.83 Hz, 6H); MS (ESI) m/z=432.8 (MH$^+$).

Step 3:

Compound (+/−) 29: The reaction mixture was stirred at rt overnight. $^1$H NMR (DMSO-d$_6$, 400 MHz) δ (ppm) 10.31 (s, 1H), 8.32 (s, 1H), 5.19-5.11 (m, 1H), 5.01 (brs, 1H), 4.56 (q, J=7.12 Hz, 2H), 4.38 (t, J=7.55 Hz, 1H), 3.56 (brs, 3H), 3.06 (s, 1H), 2.97-2.90 (m, 1H), 2.31-2.17 (m, 4H), 1.40 (t, J=7.06 Hz, 3H), 1.09 (d, J=6.81 Hz, 6H); MS (ESI) m/z=388.7 (MH$^+$).

Step 4:

Compound (+/−) 30: A solution of potassium hydroxide (102 mg, 1.82 mmol) in MeOH (2 mL) was added to the previous compound (+/−) 29 (64 mg, 0.165 mmol). The reaction mixture was stirred at rt for 6 h and at 0° C. overnight, and then quenched with acetic acid (0.11 mL, 1.98 mmol). The resulting reaction mixture was concentrated under reduced pressure. The crude residue was purified by column chromatography on silica gel (DCM/MeOH: 0 to 10%) to afford the title compound. $^1$H NMR (DMSO-d$_6$, 400 MHz) δ (ppm) 7.98 (s, 1H), 6.39 (brs, 2H), 5.08-4.98 (m, 3H), 4.44 (q, J=7.02 Hz, 2H), 4.31-4.26 (m, 1H), 3.54-3.52 (m, 2H), 3.05 (s, 1H), 2.24-2.07 (m, 4H), 1.35 (t, J=7.02 Hz, 3H); MS (ESI) m/z=318.3 (MH$^+$).

Example 34

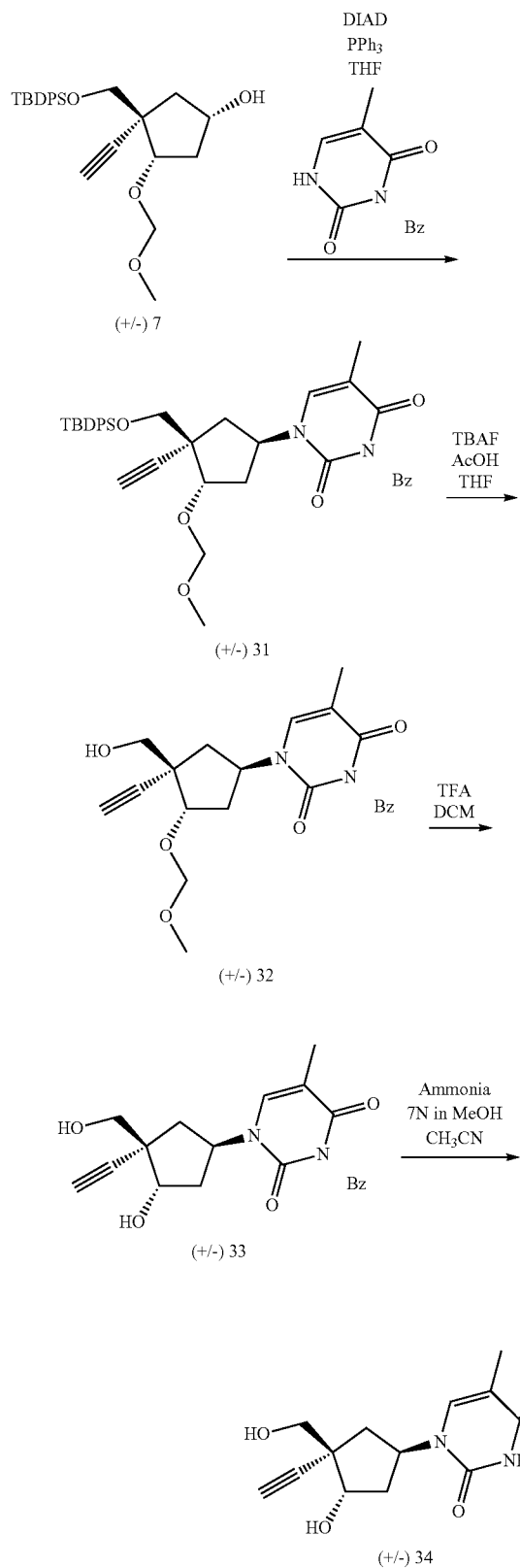

Scheme 7. Synthesis of (+/−) 34 from (+/−) 7.

Preparation of Compound (+/−) 34: 1-((1R,3S,4S)-3-ethynyl-4-hydroxy-3-(hydroxymethyl)cyclopentyl)-5-methylpyrimidine-2,4(1H,3H)-dione and 1-((1S,3R,4R)-3-ethynyl-4-hydroxy-3-(hydroxymethyl)cyclopentyl)-5-methylpyrimidine-2,4(1H,3H)-dione Compound (+/−) 34 was synthesized according to a similar procedure to that described for the synthesis of compound (+/−) 12 for the 3 first steps, beginning with compound (+/−) 7 and 3-benzoyl-5-methylpyrimidine-2,4(1H,3H)-dione.

Step 1:
Compound (+/−) 31: MS (ESI) m/z=673.7 (MNa$^+$).

Step 2:
Compound (+/−) 32: $^1$H NMR (DMSO-d$_6$, 400 MHz) δ (ppm) 7.97-7.95 (m, 2H), 7.84-7.83 (m, 1H), 7.80-7.77 (m, 1H), 7.65-7.58 (m, 2H), 5.17-5.14 (m, 1H), 5.05-4.96 (m, 1H), 4.63 (d, J=6.70 Hz, 1H), 4.60 (d, J=6.70 Hz, 1H), 4.22 (t, J=7.57 Hz, 1H), 3.51-3.50 (m, 2H), 3.26 (s, 3H), 3.06 (s, 1H), 2.27-2.03 (m, 4H), 1.87 (s, 3H); MS (ESI) m/z=413.4 (MH$^+$).

Step 3:
Compound (+/−) 33: The reaction mixture was stirred at rt overnight. The crude compound was used without further purification. MS (ESI) m/z=369.4 (MH$^+$).

Step 4:
Compound (+/−) 34: To a solution of compound (+/−) 33 (152 mg, 0.41 mmol) in CH$_3$CN (10.3 mL) was added a 7N Ammonia solution in MeOH (10 mL, 70 mmol). The reaction mixture was stirred at rt for 5 h, and then, concentrated under reduced pressure. The crude residue was purified by column chromatography on silica gel (DCM/MeOH: 0 to 20%) to afford the title compound. $^1$H NMR (DMSO-d$_6$, 400 MHz) δ (ppm) 11.21 (s, 1H), 7.51-7.505 (m, 1H), 5.06-5.01 (m, 1H), 4.98 (t, J=5.81 Hz, 1H), 4.92 (d, J=5.41 Hz, 1H), 4.21-4.15 (m, 1H), 3.49 (d, J=5.81 Hz, 2H), 3.00 (s, 1H), 2.00-1.94 (m, 3H), 1.89-1.83 (m, 1H), 1.78 (s, 3H); MS (ESI) m/z=265.3 (MH$^+$).

Example 38

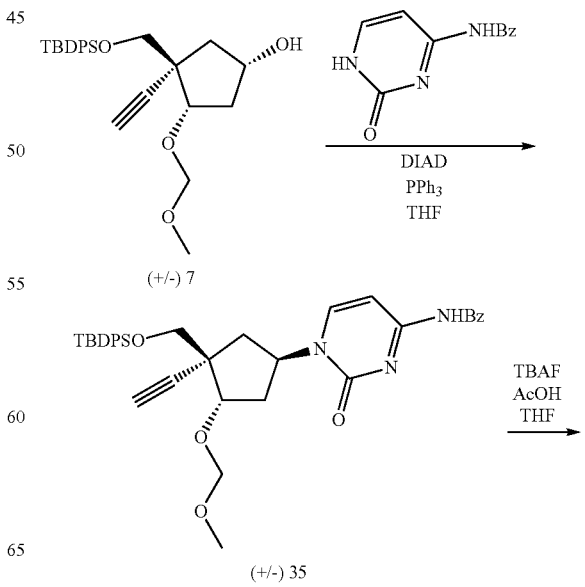

Scheme 8. Synthesis of (+/−) 38 from (+/−) 7.

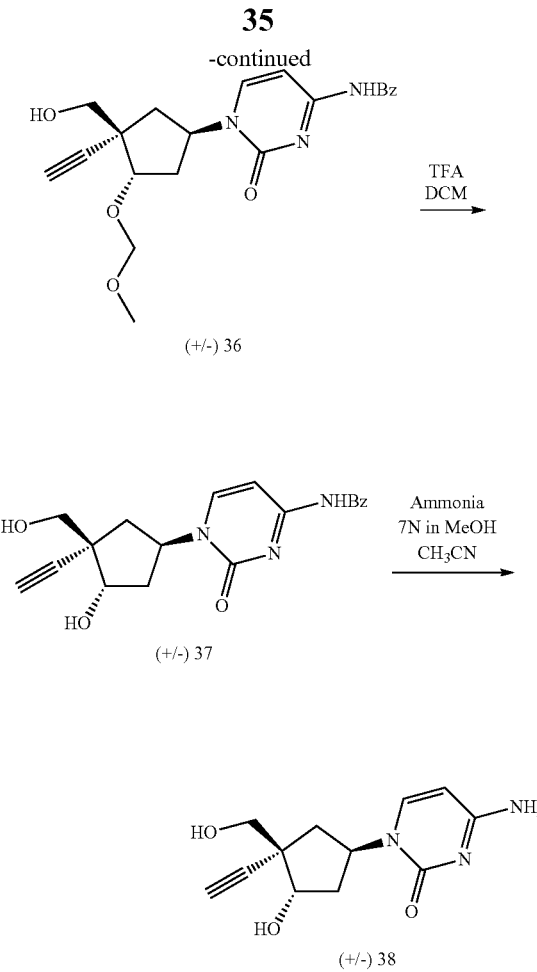

Preparation of Compound (+/−) 38: 4-amino-1-((1R,3S,4S)-3-ethynyl-4-hydroxy-3-(hydroxymethyl)cyclopentyl)pyrimidin-2(1H)-one and 4-amino-1-((1S,3R,4R)-3-ethynyl-4-hydroxy-3-(hydroxymethyl)cyclopentyl)pyrimidin-2(1H)-one Compound (+/−) 38 was synthesized according to a similar procedure to that described for the synthesis of compound (+/−) 12 for the 3 first steps, beginning with compound (+/−) 7 and N-(2-oxo-1,2-dihydropyrimidin-4-yl)benzamide.

Step 1:

Compound (+/−) 35: The crude residue was purified by column chromatography (PE/Et$_2$O: 0 to 100%) to afford the title compound. MS (ESI) m/z=636.7 (MH$^+$).

Step 2:

Compound (+/−) 36: $^1$H NMR (DMSO-d$_6$, 400 MHz) δ (ppm) 11.13 (s, 1H), 8.50 (d, J=5.69 Hz, 1H), 8.01-7.99 (m, 2H), 7.83 (d, J=5.69 Hz, 1H), 7.66-7.61 (m, 1H), 7.55-7.51 (m, 2H), 5.45-5.39 (m, 1H), 5.12 (t, J=5.69 Hz, 1H), 4.65 (d, J=6.73 Hz, 1H), 4.62 (d, J=6.73 Hz, 1H), 4.15-4.11 (m, 1H), 3.52-3.42 (m, 2H), 3.27 (s, 3H), 3.02 (s, 1H), 2.42-2.37 (m, 1H), 2.32-2.24 (m, 1H), 2.11-2.05 (m, 1H), 1.98-1.93 (m, 1H); MS (ESI) m/z=398.4 (MH$^+$).

Step 3:

Compound (+/−) 37: The reaction mixture was stirred at rt overnight. $^1$H NMR (DMSO-d$_6$, 400 MHz) δ (ppm) 11.13 (s, 1H), 8.50-8.49 (m, 1H), 8.01-7.99 (m, 2H), 7.83-7.82 (m, 1H), 7.65-7.62 (m, 1H), 7.55-7.53 (m, 2H), 5.40-5.39 (m, 1H), 5.14 (brs, 2H), 4.13-4.09 (m, 1H), 3.50-3.41 (m, 2H), 2.96 (s, 1H), 2.42-2.20 (m, 2H), 2.08-1.89 (m, 2H); MS (ESI) m/z=354.4 (MH$^+$).

Step 4:

Compound (+/−) 38: To compound (+/−) 37 (201 mg, 0.57 mmol) was added a 7N Ammonia solution in MeOH (5 mL, 35 mmol). The reaction mixture was stirred at rt overnight. After a further addition of 7N Ammonia solution in MeOH (5 mL, 35 mmol), the reaction mixture was stirred at 60° C. overnight. The reaction mixture was then concentrated under reduced pressure and the crude residue was purified by RP-18 chromatography (water/CH$_3$CN: 0 to 50%) to afford the title compound. $^1$H NMR (DMSO-d$_6$, 400 MHz) δ (ppm) 7.83 (d, J=5.82 Hz, 1H), 6.81 (m, 2H), 6.04 (d, J=5.82 Hz, 1H), 5.29-5.23 (m, 1H), 4.93 (t, J=5.82 Hz, 1H), 4.82 (d, J=5.49 Hz, 1H), 4.08-4.03 (m, 1H), 3.46 (dd, J=5.91 Hz, 10.67 Hz, 1H), 3.40 (dd, J=5.91 Hz, 10.67 Hz, 1H), 2.92 (s, 1H), 2.25 (dd, J=7.62 Hz, 13.72 Hz, 1H), 2.15-2.10 (m, 1H), 1.89-1.84 (m, 1H), 1.81 (dd, J=5.91 Hz, 13.72 Hz, 1H); MS (ESI) m/z=250.2 (MH$^+$).

Example 39

Scheme 9. Synthesis of compounds 39A and 39B.

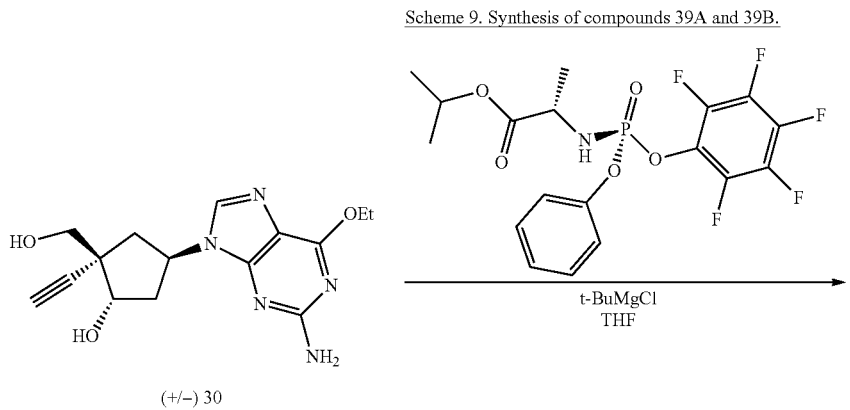

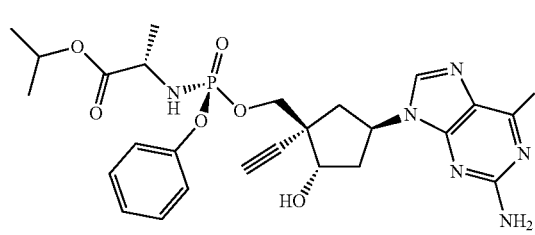
+
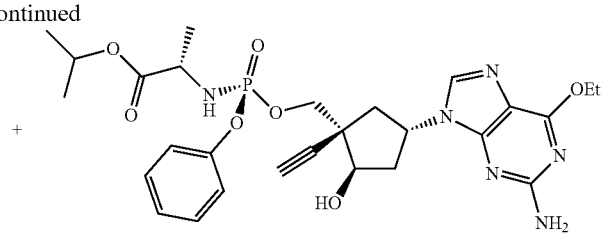

Mixture of 39A + 39B

Preparation of Compound 39A and 39B: Isopropyl ((S)-(((1S,2S,4R)-4-(2-amino-6-ethoxy-9H-purin-9-yl)-1-ethynyl-2-hydroxycyclopentyl)methoxy)(phenoxy)phosphoryl)-L-alaninate and Isopropyl ((S)-(((1R,2R,4S)-4-(2-amino-6-ethoxy-9H-purin-9-yl)-1-ethynyl-2-hydroxycyclopentyl)methoxy)(phenoxy)phosphoryl)-L-alaninate To a solution of compound (+/−) 30 (35 mg, 0.11 mmol) in THF (5 mL) at 0° C. under nitrogen was added a 1M solution of tert-butylmagnesium chloride in THF (0.28 mL, 0.28 mmol). The reaction mixture was stirred at 0° C. for 5 min and then, a solution of isopropyl ((S)-(perfluorophenoxy)(phenoxy)phosphoryl)-L-alaninate (50 mg, 0.11 mmol) in THF (2 mL) was added dropwise at 0° C. The reaction mixture was allowed to warm slowly to rt and stirred at rt overnight. The resulting reaction mixture was diluted with EtOAc and washed with a saturated NH$_4$Cl solution and brine. The organic layer was dried, filtered and concentrated under reduced pressure. The crude residue was purified by flash chromatography on silica gel (DCM/MeOH: 0 to 5%) to afford the title compound as a mixture of diastereomers.

$^1$H NMR (DMSO-d$_6$, 400 MHz) δ (ppm) 7.95 (s, 0.7H), 7.94 (s, 0.3H), 7.37-7.32 (m, 2H), 7.23-7.21 (m, 2H), 7.18-7.13 (m, 1H), 6.41 (m, 2H), 6.06-5.98 (m, 1H), 5.27-5.25 (m, 1H), 5.09-5.01 (m, 1H), 4.89-4.78 (m, 1H), 4.44 (q, J=6.97 Hz, 2H), 4.34-4.28 (m, 1H), 4.28-4.16 (m, 1H), 4.11-4.03 (m, 1H), 3.86-3.77 (m, 1H), 3.18 (s, 1H), 2.31-2.04 (m, 4H), 1.35 (t, J=6.97 Hz, 3H), 1.23-1.21 (m, 3H), 1.16-1.08 (m, 6H); $^{31}$P NMR (DMSO-d$_6$, 162 MHz) δ (ppm) 3.34 (s, 0.3P), 3.28 (0.7P); MS (ESI) m/z=587.2 (MH$^+$).

The two diastereomers 39A and 39B were separated by preparative chiral SFC with the following conditions: Column: AD-H, 2*25 cm, 5 μm; Mobile Phase A: CO$_2$; Mobile Phase B: iPrOH; Gradient: 30% B in 8 min; Flow rate: 60 mL/min; Detector: UV 220 nm; to afford:

Diastereomer 39A: Faster eluting: Rt=3.22 min; $^1$H NMR (CDCl$_3$, 600 MHz) δ (ppm) 7.44 (s, 1H), 7.30-7.27 (m, 2H), 7.23-7.22 (m, 2H), 7.17-7.14 (m, 1H), 5.18 (brs, 2H), 5.08-5.02 (m, 2H), 4.53 (q, J=7.31 Hz, 2H), 4.48-4.46 (m, 1H), 4.44-4.42 (m, 1H), 4.38-4.35 (m, 1H), 4.08-4.00 (m, 3H), 2.51-2.46 (m, 1H), 2.41 (s, 1H), 2.40-2.39 (m, 2H), 2.37-2.32 (m, 1H), 1.45 (t, J=7.31 Hz, 3H), 1.405 (d, J=6.83 Hz, 3H), 1.25 (d, J=5.85 Hz, 3H), 1.24 (d, J=5.85 Hz, 3H); $^{31}$P NMR (CDCl$_3$, 243 MHz) δ (ppm) 3.21 (s, 1P); MS (ESI) m/z=587.6 (MH$^+$); and Diastereomer 39B: Slower eluting: Rt=5.37 min; $^1$H NMR (CDCl$_3$, 600 MHz) δ (ppm) 7.52 (s, 1H), 7.33-7.30 (m, 2H), 7.25-7.21 (m, 2H), 7.18-7.15 (m, 1H), 5.24 (brs, 2H), 5.12-4.99 (m, 2H), 4.66-4.63 (m, 1H), 4.55-4.52 (m, 3H), 4.47-4.45 (m, 1H), 4.38-4.35 (m, 1H), 4.03-3.99 (m, 1H), 3.77-3.71 (m, 1H), 2.62-2.58 (m, 1H), 2.46-2.43 (m, 1H), 2.42 (s, 1H), 2.40-2.36 (m, 1H), 2.33-2.29 (m, 1H), 1.45 (t, J=6.83 Hz, 3H), 1.39 (d, J=6.83 Hz, 3H), 1.225 (d, J=5.85 Hz, 3H), 1.22 (d, J=5.85 Hz, 3H); $^{31}$P NMR (CDCl$_3$, 243 MHz) δ (ppm) 2.88 (s, 1P); MS (ESI) m/z=587.6 (MH$^+$).

Alternative Route for Synthesis of Prodrug 39:

Scheme 9bis. Synthesis of prodrug 39, alternative route.

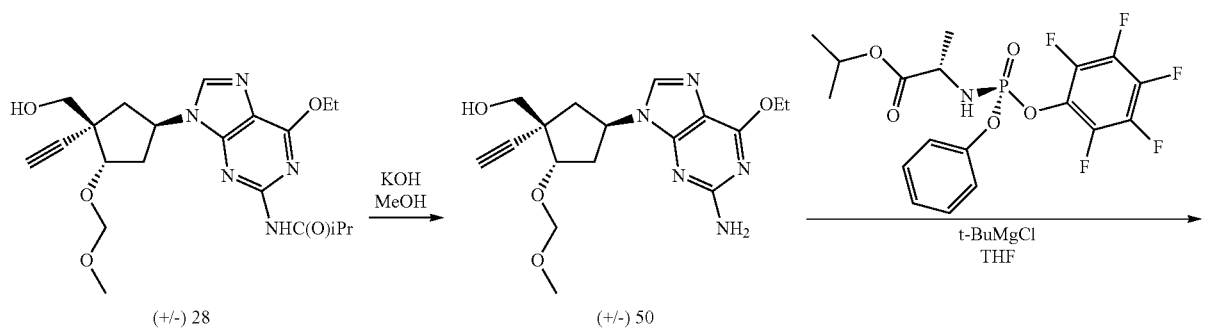

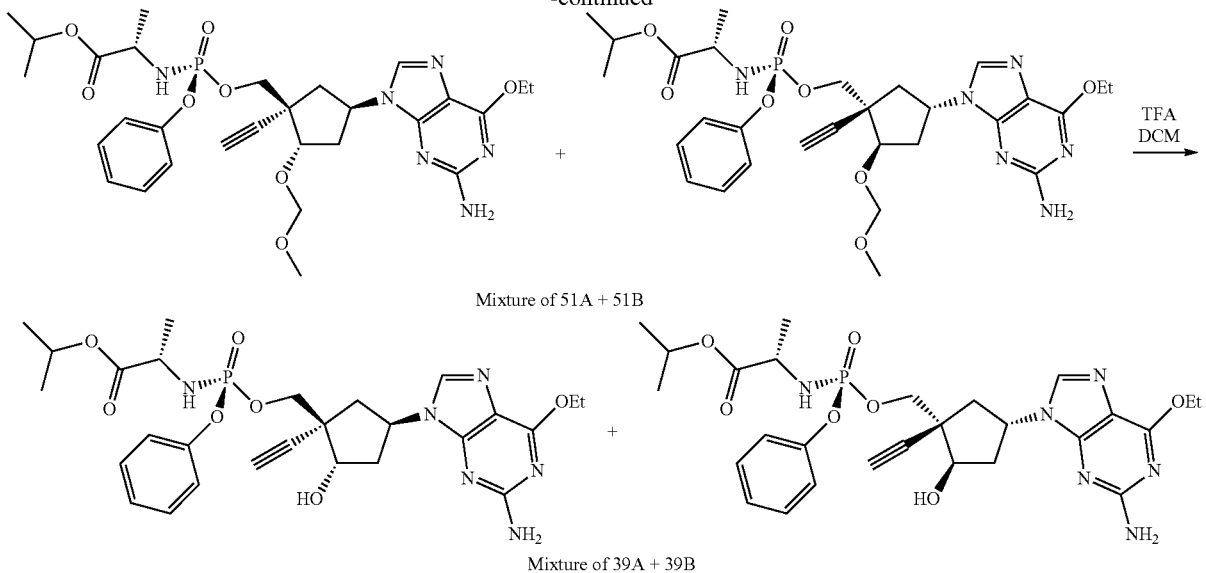

Mixture of 51A + 51B

Mixture of 39A + 39B

Preparation of Compound 39A and 39B: Isopropyl ((S)-(((1S,2S,4R)-4-(2-amino-6-ethoxy-9H-purin-9-yl)-1-ethynyl-2-hydroxcyclopentyl)methoxy)(phenoxy)phosphoryl)-L-alaninate and Isopropyl ((S)-(((1R,2R,4S)-4-(2-amino-6-ethoxy-9H-purin-9-yl)-1-ethynyl-2-hydroxycyclopentyl)methoxy)(phenoxy)phosphoryl)-L-alaninate Step 1:
Compound (+/−) 50: Compound (+/−) 50 was synthesized according to a similar procedure to that described for the synthesis of compound (+/−) 30, starting from compound (+/−) 28. The crude residue was purified by column chromatography (DCM/MeOH: 0 to 10%) to afford the title compound. $^1$H NMR (DMSO-$d_6$, 400 MHz) δ (ppm) 7.99 (s, 1H), 6.39 (brs, 2H), 5.16 (t, J=5.77 Hz, 1H), 5.10-5.01 (m, 1H), 4.67 (d, J=6.69 Hz, 1H), 4.63 (d, J=6.69 Hz, 1H), 4.44 (q, J=7.01 Hz, 2H), 4.31-4.28 (m, 1H), 3.59-3.51 (m, 2H), 3.28 (s, 3H), 3.09 (s, 1H), 2.32-2.14 (m, 4H), 1.35 (t, J=7.01 Hz, 3H); MS (ESI) m/z=362.6 (MH$^+$).

Step 2:
Compounds 51A and 51B: Mixture of compounds 51A and 51B was synthesized according to a similar procedure to that described for the synthesis of compounds 39A/39B, starting from compound (+/−) 50. The crude residue was purified by column chromatography (DCM/MeOH: 0 to 10%) to afford the title compound as a mixture of diastereomers. $^1$H NMR (DMSO-$d_6$, 400 MHz) δ (ppm) 7.94 (s, 0.5H), 7.93 (0.5H), 7.37-7.32 (m, 2H), 7.23-7.21 (m, 2H), 7.18-7.13 (m, 1H), 6.41-6.40 (m, 2H), 6.09-6.01 (m, 1H), 5.12-5.03 (m, 1H), 4.89-4.79 (m, 1H), 4.67-4.62 (m, 2H), 4.45 (q, J=6.98 Hz, 2H), 4.34-4.07 (m, 3H), 3.86-3.78 (m, 1H), 3.28 (s, 1.5H), 3.275 (s, 1.5H), 3.24 (s, 0.5H), 3.23 (s, 0.5H), 2.40-2.11 (m, 4H), 1.35 (t, J=6.98 Hz, 3H), 1.24-1.22 (m, 3H), 1.16-1.10 (m, 6H); $^{31}$P NMR (DMSO-$d_6$, 162 MHz) δ (ppm) 3.26 (s, 0.5P), 3.15 (0.5P); MS (ESI) m/z=631.4 (MH$^+$).

Step 3:
Compounds 39A and 39B: To a solution of mixture of diastereomers 51A/51B (270 mg, 0.43 mmol) in DCM (5 mL) at 10° C. was added TFA (0.99 mL, 12.84 mmol). The reaction mixture was stirred between 10° C. and 25° C. for 2 h and at 0° C. for 2h30, and then, concentrated under reduced pressure under N$_2$ flow at 10° C. The crude residue was purified by column chormatography on silica gel (DCM/MeOH: 0 to 4%) to afford the title compound as a mixture of diastereomers. $^{31}$P NMR (DMSO-$d_6$, 162 MHz) δ (ppm) 3.34 (s, 0.4P), 3.28 (0.6P); MS (ESI) m/z=587.8 (MH$^+$).

Examples 40-49

Scheme 10. General procedure for synthesis of triphosphates.

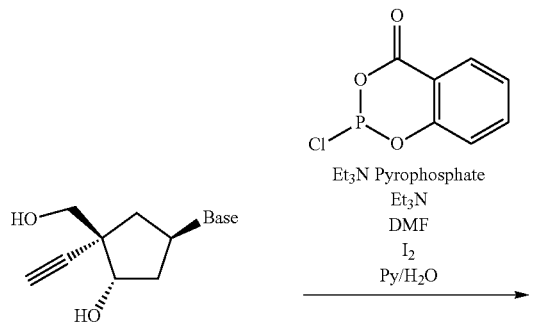

(+/−) 12: Base: 2-F, 6-Cl-purine
(+/−) 13: Base: 2-F, 6-NH$_2$-purine
(+/−) 14: Base: 2-NH$_2$, 6-Cl-purine
(+/−) 17: Base: 2, 6-diCl-purine
(+/−) 18: Base: 2-Cl, 6-NH$_2$-purine
(+/−) 21: Base: 2, 6-diCl, 7-deazapurine
(+/−) 22: Base: 2-Cl, 6-NH$_2$, 7-deazapurine
(+/−) 26: Base: G
(+/−) 34: Base: T
18B: Base = 2-Cl, 6-NH$_2$-purine
(+/−) 38: Base = C

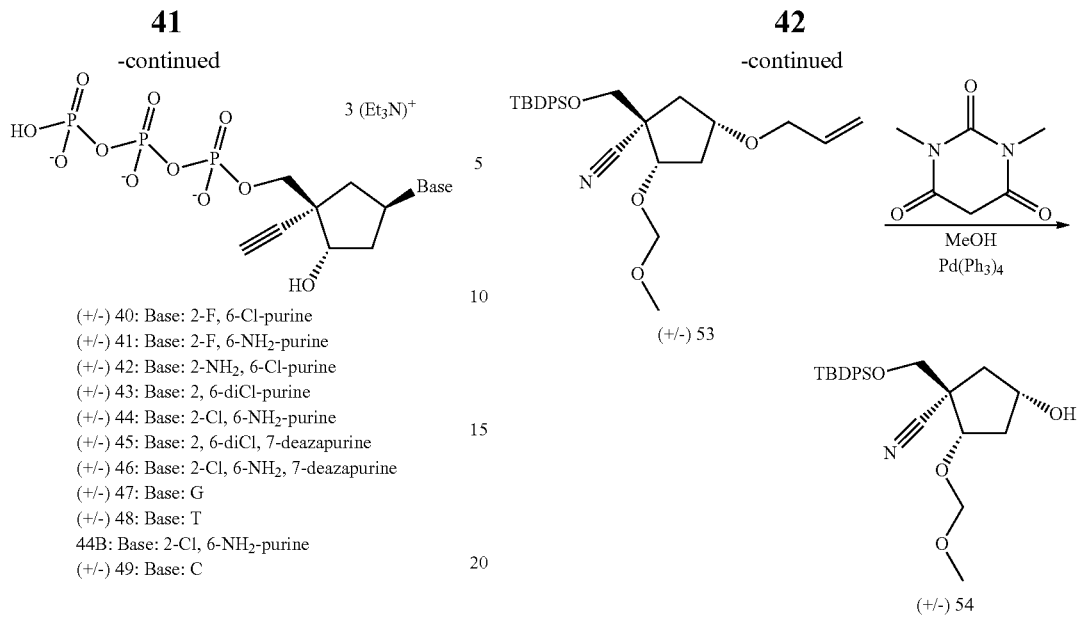

(+/−) 40: Base: 2-F, 6-Cl-purine
(+/−) 41: Base: 2-F, 6-NH₂-purine
(+/−) 42: Base: 2-NH₂, 6-Cl-purine
(+/−) 43: Base: 2, 6-diCl-purine
(+/−) 44: Base: 2-Cl, 6-NH₂-purine
(+/−) 45: Base: 2, 6-diCl, 7-deazapurine
(+/−) 46: Base: 2-Cl, 6-NH₂, 7-deazapurine
(+/−) 47: Base: G
(+/−) 48: Base: T
44B: Base: 2-Cl, 6-NH₂-purine
(+/−) 49: Base: C Preparation of Compounds (+/−) 40-49 and 44B:

Compounds (+/−) 40-49 and 44B were synthesized according to procedure described in literature: *Chem. Comm.* 2011, 47, 8142-8144.

Compound (+/−) 40: MS (ESI) m/z=549.0 (MH⁻).
Compound (+/−) 41: MS (ESI) m/z=530.0 (MH⁻).
Compound (+/−) 42: MS (ESI) m/z=546.0 (MH⁻).
Compound (+/−) 43: MS (ESI) m/z=565.0 (MH⁻).
Compound (+/−) 44: MS (ESI) m/z=546.0 (MH⁻).
Compound (+/−) 45: MS (ESI) m/z=564.0 (MH⁻).
Compound (+/−) 46: MS (ESI) m/z=545.0 (MH⁻).
Compound (+/−) 47: MS (ESI) m/z=528.0 (MH⁻).
Compound (+/−) 48: MS (ESI) m/z=503.0 (MH⁻).
Compound 44B: MS (ESI) m/z=546.0 (MH⁻).
Compound (+/−) 49: MS (ESI) m/z=488.0 (MH⁻).

Scheme 11. Synthesis of Intermediate (+/−) 54

Route 1

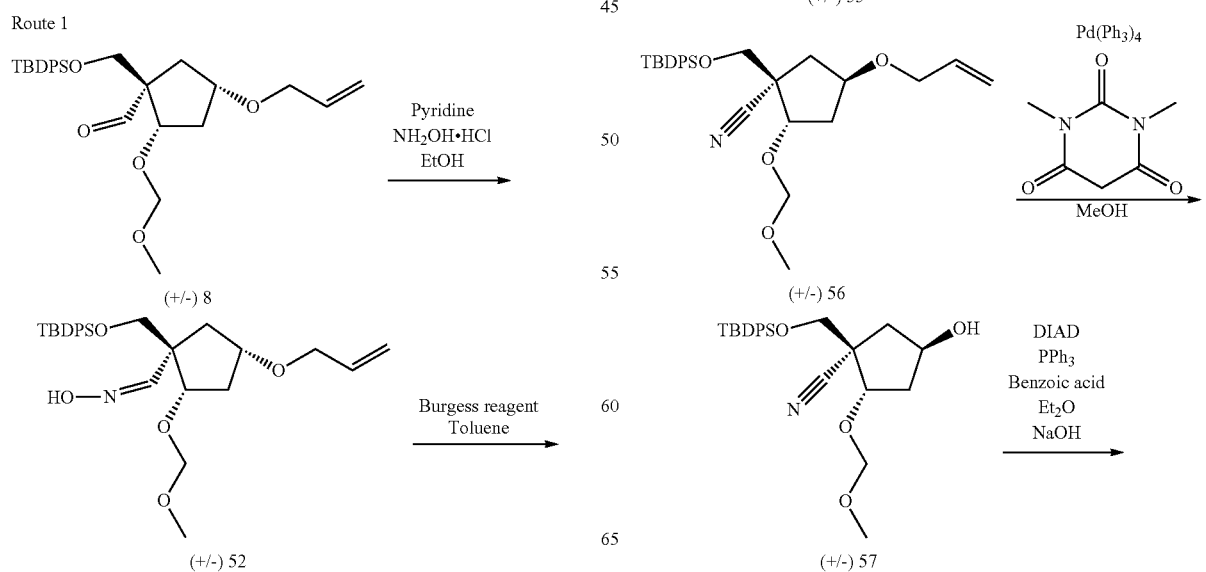

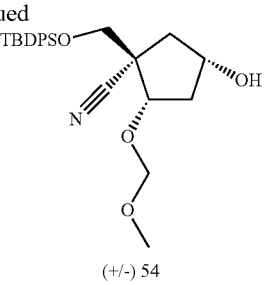

(+/-) 54

Preparation of Compound (+/−) 54: (1S,2S,4S)-1-(((tert-butyldiphenylsilyl)oxy)methyl)-4-hydroxy-2-(methoxymethoxy)cyclopentane-1-carbonitrile and (1R,2R,4R)-1-(((tert-butyldiphenylsilyl)oxy)methyl)-4-hydroxy-2-(methoxymethoxy)cyclopentane-1-carbonitrile Route 1: beginning with (+/−) 8
Step 1a:
To a solution of Compound (+/−) 8 (0.996 g, 2.06 mmol) in EtOH (10 mL) and pyridine (10 mL) was added hydroxylamine hydrochloride (0.72 g, 10.32 mmol). The reaction mixture was stirred at rt for 2h. The reaction mixture was concentrated under reduced pressure, diluted with DCM and washed with water. The organic layer was dried, filtered and concentrated under reduced pressure to afford the expected compound (+/−) 52. The crude residue was used in the next step without further purification. MS (ESI) m/z=498.6 ($MH^+$).

Step 2a:
To a solution of compound (+/−) 52 (896 mg, 1.8 mmol) in Toluene (25 mL) was added Burgess reagent (2.15 g, 9.0 mmol). The reaction mixture was stirred at rt for 1h, and then, concentrated under reduced pressure. The crude residue was purified by flash chromatography on silica gel (Et20/PE: 0 to 70%) to afford the expected compound (+/−) 53. MS (ESI) m/z=502.2 ($MNa^+$).

Step 3a:
To a solution of Compound (+/−) 53 (624 mg, 1.30 mmol) in MeOH (47 mL) were added 1,3-dimethylbarbituric acid (406 mg, 2.60 mmol) and tetrakis(triphenylphosphine)palladium (0) (75 mg, 0.065 mmol) at rt. The reaction mixture was stirred at rt overnight. Additional tetrakis(triphenylphosphine)palladium (0) (75 mg, 0.065 mmol) and 2h of stirring at rt were necessary to complete the reaction. The reaction mixture was concentrated under reduced pressure and directly purified by flash chromatography on silica gel (PE/Et$_2$O: 0 to 100%) to afford the expected compound (+/−) 54. MS (ESI) m/z=462.2 ($MNa^+$).

Route 2: beginning with (+/−) 4
Step 1a:
Compound (+/−) 55 was synthesized according to a similar procedure described for the synthesis of compound (+/−) 52, starting from compound (+/−) 4. MS (ESI) m/z=498.5 ($MH^+$).

Step 2a:
Compound (+/−) 56 was synthesized according to a similar procedure described for the synthesis of compound (+/−) 53, starting from compound (+/−) 55. MS (ESI) m/z=502.5 ($MNa^+$).

Step 3a:
Compound (+/−) 57 was synthesized according to a similar procedure described for the synthesis of compound (+/−) 54, starting from compound (+/−) 56. MS (ESI) m/z=462.5 ($MNa^+$).

Step 4a:
Compound (+/−) 54 was synthesized according to a similar procedure described for the synthesis of compound (+/−) 7 (Routel), starting from compound (+/−) 57. $^1$H NMR (DMSO-d$_6$, 400 MHz) δ (ppm) 7.66-7.63 (m, 4H), 7.51-7.43 (m, 6H), 4.95-4.75 (m, 1H), 4.62-4.58 (m, 2H), 4.10-4.03 (m, 1H), 3.99-3.95 (m, 1H), 3.71 (d, J=9.97 Hz, 1H), 3.65 (d, J=9.97 Hz, 1H), 3.22 (s, 3H), 2.31-2.25 (m, 1H), 2.16-2.11 (m, 1H), 2.02-1.97 (m, 1H), 1.69-1.63 (m, 1H), 1.03 (s, 9H); MS (ESI) m/z=462.2 ($MNa^+$).

Example 61

Scheme 12. Synthesis of (+/-) 61 from (+/-) 54.

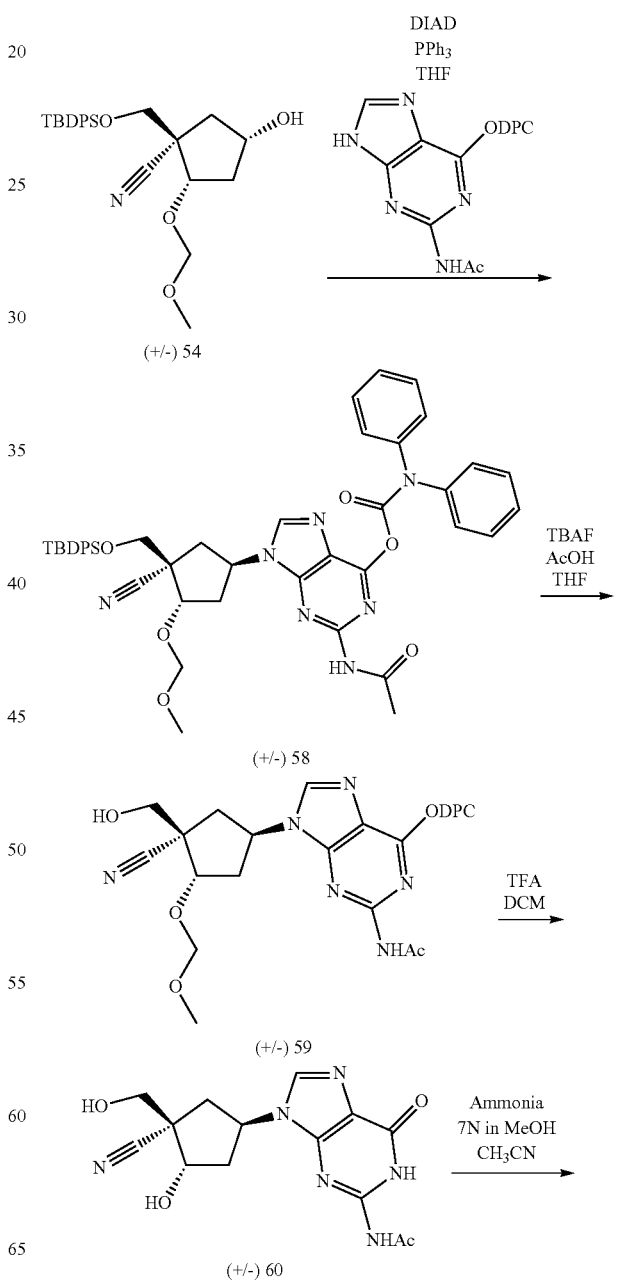

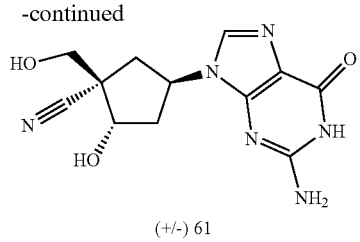

(+/−) 61

Preparation of Compound (+/−) 61: (1S,2S,4R)-4-(2-amino-6-oxo-1,6-dihydro-9H-purin-9-yl)-2-hydroxy-1-(hydroxymethyl)cyclopentane-1-carbonitrile and (1R,2R,4S)-4-(2-amino-6-oxo-16-dihydro-9H-purin-9-yl)-2-hydroxy-1-(hydroxymethyl)cyclopentane-1-carbonitrile Compound (+/−) 61 was synthesized according to a similar procedure to that described for the synthesis of compound (+/−) 12 for the 3 first steps, beginning with compound (+/−) 54 and 2-acetamido-9H-purin-6-yl diphenylcarbamate.

Step 1:
Compound (+/−) 58: MS (ESI) m/z=811.1 (MH+).
Step 2:
Compound (+/−) 59: MS (ESI) m/z=572.6 (MH+).
Step 3:
Compound (+/−) 60: MS (ESI) m/z=333.1 (MH+).
Step 4:
Compound (+/−) 61: To a solution of compound (+/−) 60 (90 mg, 0.27 mmol) in CH$_3$CN (6.8 mL) was added a 7N Ammonia solution in MeOH (1.9 mL, 13.5 mmol). The reaction mixture was stirred at 50° C. for 6h and at rt overnight. The reaction mixture was then concentrated under reduced pressure and the crude residue was triturated in CH$_3$CN, washed in CH$_3$CN and pentane and filtered to afford the title compound. $^1$H NMR (DMSO-d6, 400 MHz) δ (ppm) 10.34 (brs, 1H), 7.82 (s, 1H), 6.46 (brs, 2H), 5.80 (d, J=4.69 Hz, 1H), 5.56 (t, J=5.75 Hz, 1H), 5.04-4.96 (m, 1H), 4.33-4.29 (m, 1H), 3.71 (dd, J=11.00 Hz, 5.85 Hz, 1H), 3.58 (dd, J=11.00 Hz, 5.62 Hz, 1H), 2.57-2.52 (m, 1H), 2.33-2.26 (m, 1H), 2.15-2.03 (m, 2H); MS (ESI) m/z=291.0 (MH+).

Example 65

Scheme 13. Synthesis of (+/−) 65 from (+/−) 54.

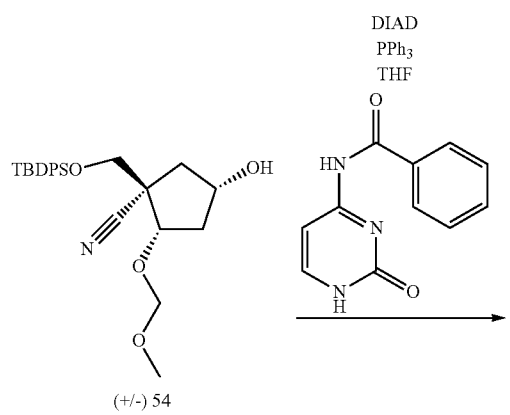

(+/−) 54

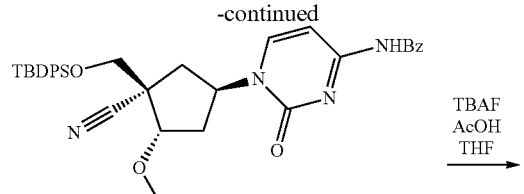

(+/−) 62

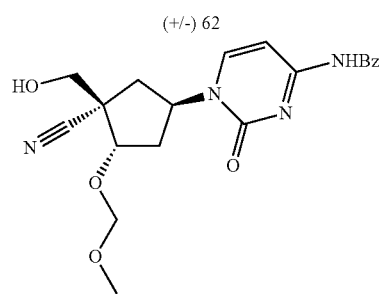

(+/−) 63

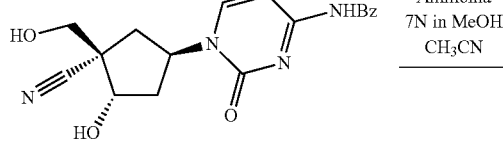

(+/−) 64

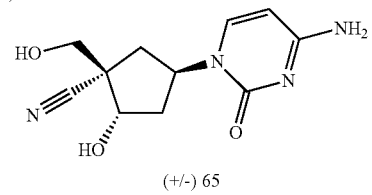

(+/−) 65

Preparation of Compound (+/−) 65: (1S,2S,4R)-4-(4-amino-2-oxopyrimidin-1(2H)-yl)-2-hydroxy-1-(hydroxymethyl)cyclopentane-1-carbonitrile and (1R,2R,4S)-4-(4-amino-2-oxopyrimidin-1 (2H)-yl)-2-hydroxy-1-(hydroxymethyl)cyclopentane-1-carbonitrile Compound (+/−) 65 was synthesized according to a similar procedure to that described for the synthesis of compound (+/−) 12 for the 3 first steps, beginning with compound (+/−) 54 and N-(2-oxo-1,2-dihydropyrimidin-4-yl)benzamide.

Step 1:
Compound (+/−) 62: The crude residue was purified by column chromatography on silica gel (PE/Et$_2$O: 0 to 100%) to afford the expected compound. MS (ESI) m/z=638.0 (MH+).

Step 2:
Compound (+/−) 63: The reaction mixture was stirred at rt for 2 days. The reaction mixture was concentrated under reduced pressure. The crude residue was purified by column chromatography on silica gel (PE/EtOAc: 0 to 100%) to afford the expected compound. $^1$H NMR (DMSO-d$_6$, 400 MHz) δ (ppm) 11.13 (s, 1H), 8.51 (d, J=5.69 Hz, 1H), 8.01-7.99 (m, 2H), 7.85 (d, J=5.69 Hz, 1H), 7.66-7.61 (m, 1H), 7.55-7.52 (m, 2H), 5.61 (t, J=5.69 Hz, 1H), 5.48-5.43

(m, 1H), 4.69 (s, 2H), 4.23 (t, J=6.46 Hz, 1H), 3.65-3.55 (m, 2H), 2.73-2.69 (m, 1H), 2.32-2.27 (m, 1H), 2.21-2.15 (m, 1H), 2.05-2.01 (m, 1H); MS (ESI) m/z=399.6 (MH+).

Step 3:

Compound (+/−) 64: The crude residue was purified by column chromatography on silica gel (PE/EtOAc: 0 to 100%) to afford the expected compound. $^1$H NMR (DMSO-d6, 400 MHz) δ (ppm) 11.13 (s, 1H), 8.51 (d, J=5.75 Hz, 1H), 8.01-7.99 (m, 2H), 7.84 (d, J=5.75 Hz, 1H), 7.65-7.61 (m, 1H), 7.55-7.51 (m, 2H), 5.71-5.70 (m, 1H), 5.48-5.41 (m, 2H), 4.22-4.18 (m, 1H), 3.65-3.61 (m, 1H), 3.53-3.49 (m, 1H), 2.72-2.66 (m, 1H), 2.24-2.17 (m 1H), 2.11-2.05 (m, 1H), 1.98-1.94 (m, 1H); MS (ESI) m/z=355.4 (MH+).

Step 4:

Compound (+/−) 65: To compound (+/−) 64 (64 mg, 0.18 mmol) was added a 7N Ammonia solution in MeOH (5 mL). The reaction mixture was stirred at rt overnight, and then, concentrated under reduced pressure. The crude residue was purified by column chromatography on silica gel (DCM/MeOH: 0 to 10%) to afford the title compound. $^1$H NMR (DMSO-d$_6$, 400 MHz) δ (ppm) 7.84 (d, J=5.75 Hz, 1H), 6.82 (m, 2H), 6.06 (d, J=5.75 Hz, 1H), 5.63 (d, J=5.03 Hz, 1H), 5.44 (t, J=5.67 Hz, 1H), 5.34-5.28 (m, 1H), 4.18-4.13 (m, 1H), 3.61 (dd, J=5.89 Hz, 10.93 Hz, 1H), 3.48 (dd, J=5.89 Hz, 10.93 Hz, 1H), 2.57-2.53 (m, 1H), 2.13-2.06 (m 1H), 2.02-1.96 (m, 1H), 1.90-1.85 (m, 1H); MS (ESI) m/z=251.1 (MH+).

Example 69

Scheme 14. Synthesis of (+/−) 69 from (+/−) 54.

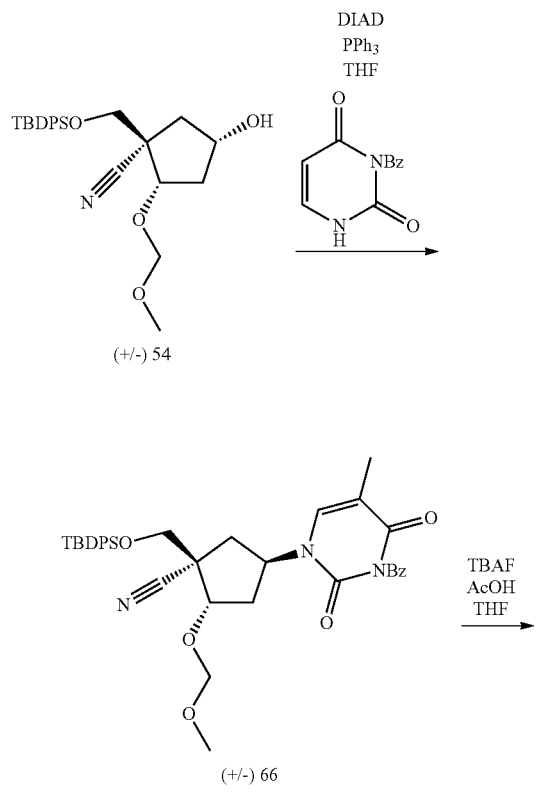

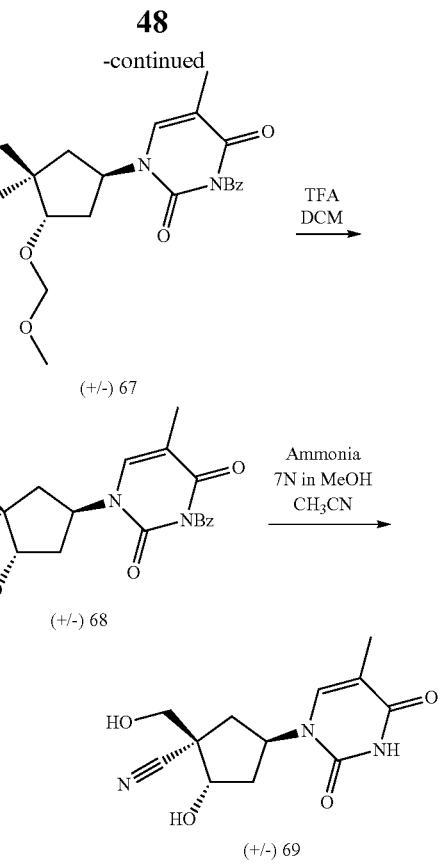

Preparation of Compound (+/−) 69: (1S,2S,4R)-2-hydroxy-1-(hydroxymethyl)-4-(5-methyl-2,4-dioxo-3,4-dihydropyrimidin-1 (2H)-yl)cyclopentane-1-carbonitrile and (1R,2R,4S)-2-hydroxy-1-(hydroxymethyl)-4-(5-methyl-2,4-dioxo-3,4-dihydropyrimidin-1 (2H)-yl)cyclopentane-1-carbonitrile Compound (+/−) 69 was synthesized according to a similar procedure to that described for the synthesis of compound (+/−) 12 for the 3 first steps, beginning with compound (+/−) 54 and 3-benzoylpyrimidine-2,4(1H,3H)-dione.

Step 1:

Compound (+/−) 66: The crude residue was purified by column chromatography on silica gel (PE/EtOAc: 0 to 60%) to afford the expected compound. $^1$H NMR (CDCl$_3$, 400 MHz) δ (ppm) 7.92-7.90 (m, 2H), 7.68-7.62 (m, 5H), 7.52-7.48 (m, 2H), 7.46-7.42 (m, 2H), 7.40-7.36 (m, 4H), 6.99 (m, 1H), 4.89-4.80 (m, 1H), 4.65-4.61 (m, 2H), 4.38-4.35 (m, 1H), 3.81 (s, 2H), 3.33 (s, 3H), 2.58-2.52 (m, 1H), 2.41-2.26 (m, 3H), 1.94-1.93 (m, 3H), 1.07 (s, 9H); MS (ESI) m/z=652.6 (MH+).

Step 2:

Compound (+/−) 67: The crude residue was purified by column chromatography on silica gel (DCM/MeOH: 0 to 10%) to afford the expected compound. $^1$H NMR (DMSO-d6, 400 MHz) δ (ppm) 7.98 (m, 1H), 7.96 (m, 1H), 7.85-7.84 (m, 1H), 7.81-7.77 (m, 1H), 7.62-7.58 (m, 2H), 5.67 (t, J=5.52 Hz, 1H), 5.02-4.93 (m, 1H), 4.66 (s, 2H), 4.28-4.24 (m, 1H), 3.70-3.66 (m, 1H), 3.61-3.57 (m, 1H), 3.30 (s, 3H), 2.45-2.40 (m, 1H), 2.35-2.27 (m, 1H), 2.18-2.11 (m, 1H), 2.07-2.01 (m, 1H), 1.86 (s, 3H); MS (ESI) m/z=414.2 (MH+).

Step 3:
Compound (+/−) 68: The reaction mixture was stirred at rt overnight, and then, concentrated under reduced pressure. The crude residue was purified by column chromatography on silica gel (DCM/MeOH: 0 to 10%) to afford the expected compound. MS (ESI) m/z=370.0 (MH+).

Step 4:
Compound (+/−) 69: Compound (+/−) 69 was synthesized according to a similar procedure to that described for the synthesis of compound (+/−) 65, beginning with compound (+/−) 68. The crude residue was purified by column chromatography on silica gel (DCM/MeOH: 0 to 10%) to afford the title compound. $^{1}$H NMR (DMSO-$d_6$, 400 MHz) δ (ppm) 11.25 (brs, 1H), 7.555-7.55 (m, 1H), 5.74 (d, J=4.79 Hz, 1H), 5.52 (t, J=5.65 Hz, 1H), 5.06-4.97 (m, 1H), 4.25-4.20 (m, 1H), 3.71-3.67 (m, 1H), 3.55-3.51 (m, 1H), 2.34-2.29 (m, 1H), 2.17-2.10 (m, 1H), 1.97-1.84 (m, 2H), 1.77 (s, 3H); MS (ESI) m/z=266.2 (MH+).

Example 73

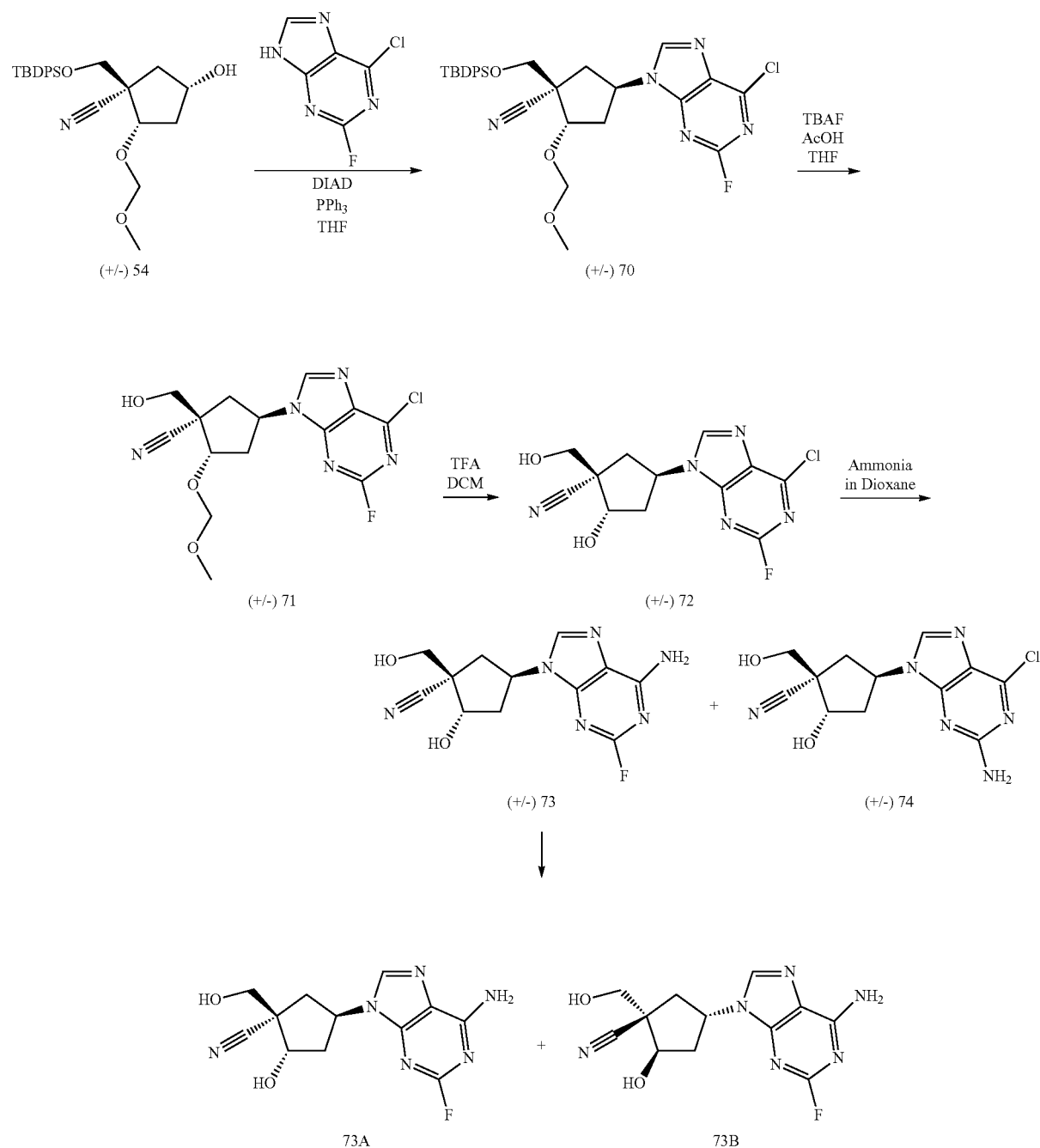

Scheme 15. Synthesis of (+/−) 73 and 73A/73B from (+/−) 54.

Preparation of Compound (+/−) 73: (1S,2S4R)-4-(6-amino-2-fluoro-9H-purin-9-yl)-2-hydroxy-1-(hydroxymethyl)cyclopentane-1-carbonitrile and (1R,2R,4S)-4-(6-amino-2-fluoro-9H-purin-9-yl)-2-hydroxy-1-(hydroxymethyl)cyclopentane-1-carbonitrile Compound (+/−) 73 was synthesized according to a similar procedure to that described for the successive synthesis of compounds (+/−) 12 and (+/−) 13, beginning with compound (+/−) 54 and 6-chloro-2-fluoro-9H-purine.

Step 1:

Compound (+/−) 70: The crude residue was purified by column chromatography on silica gel (PE/EtOAc: 0 to 60%) to afford the expected compound. $^1$H NMR (DMSO-d6, 400 MHz) δ (ppm) 8.75 (s, 1H), 7.67-7.65 (m, 4H), 7.49-7.42 (m, 6H), 5.29 (quintuplet, J=8.87 Hz, 1H), 4.73 (d, J=6.96 Hz, 1H), 4.68 (d, J=6.96 Hz, 1H), 4.53-4.50 (m, 1H), 4.06-4.01 (m, 1H), 3.89 (d, J=10.36 Hz, 1H), 3.30 (s, 3H), 2.81-2.75 (m, 1H), 2.58-2.53 (m, 1H), 2.42-2.32 (m, 2H), 1.05 (s, 9H); MS (ESI) m/z=595.3 (MH$^+$).

Step 2:

Compound (+/−) 71: The crude residue was purified by column chromatography on silica gel (DCM/MeOH: 0 to 10%) to afford the expected compound. $^1$H NMR (DMSO-d6, 400 MHz) δ (ppm) 8.80 (s, 1H), 5.77-5.74 (m, 1H), 5.25 (quintuplet, J=8.78 Hz, 1H), 4.73-4.70 (m, 2H), 4.41-4.38 (m, 1H), 3.75 (dd, J=10.94 Hz, 5.54 Hz, 1H), 3.67 (dd, J=10.94 Hz, 5.54 Hz, 1H), 2.73-2.67 (m, 1H), 2.60-2.53 (m, 1H), 2.43-2.36 (m, 1H), 2.33-2.27 (m, 1H); MS (ESI) m/z=356.3 (MH$^+$).

Step 3:

Compound (+/−) 72: The reaction mixture was stirred at rt overnight, and then, concentrated under reduced pressure. The crude residue was purified by column chromatography on silica gel (DCM/MeOH: 0 to 10%) to afford the expected compound. $^1$H NMR (DMSO-d$_6$, 400 MHz) δ (ppm) 8.79 (s, 1H), 5.91 (brs, 1H), 5.61 (brs, 1H), 5.27 (quintuplet, J=8.69 Hz, 1H), 4.39 (t, J=5.43 Hz, 1H), 3.75 (d, J=10.87 Hz, 1H), 3.61 (d, J=10.87 Hz, 1H), 2.70-2.64 (m, 1H), 2.48-2.46 (m, 1H), 2.27-2.21 (m, 2H); MS (ESI) m/z=312.2 (MH$^+$).

Step 4:

Compounds (+/−) 73 and (+/−) 74: A solution of compound (+/−) 72 (81 mg, 0.26 mmol) in 2M Ammonia in Dioxane (0.13 mL, 0.26 mmol) was stirred at rt for 3 days in a sealed system. This solution was re-charged every day with ammonia gas. The reaction mixture was concentrated under reduced pressure and the crude residue was purified by RP-18 chromatography (H$_2$O/CH$_3$CN) to afford a mixture of compounds (+/−) 73 and (+/−) 74: MS (ESI) m/z=293.2 (MH$^+$) and 309.2 (MH$^+$).

Preparation of Compounds 73A and 73B: (1S,2S,4R)-4-(6-amino-2-fluoro-9H-purin-9-yl)-2-hydroxy-1-(hydroxymethyl)cyclopentane-1-carbonitrile and (1R,2R,4S)-4-(6-amino-2-fluoro-9H-purin-9-yl)-2-hydroxy-1-(hydroxymethyl)cyclopentane-1-carbonitrile Compounds 73A and 73B were separated from the mixture of compounds (+/−) 73 and (+/−) 74 by 2 successive preparative chiral SFC with the following conditions: 1/Column: OD-H, 2*25 cm, 5 μm; Mobile Phase A: CO$_2$; Mobile Phase B: EtOH; Gradient: 30% B in 8 min; Flow rate: 60 mL/min; Detector: UV 220 nm to afford the expected mixture 73A/73B (Faster elutng: Rt=2.1-2.5 min); and then: 2/Column: IC, 2*25 cm, 5 μm; Mobile Phase A: CO$_2$; Mobile Phase B: iPrOH; Gradient: 30% B in 8 min; Flow rate: 60 mL/min; Detector: UV 220 nm to afford:

Enantiomer 73A: Faster eluting: Rt=3.07 min; $^1$H NMR (CD$_3$OD, 600 MHz) δ (ppm) 8.10 (s, 1H), 5.24 (quintuplet, J=8.80 Hz, 1H), 4.57-4.54 (m, 1H), 3.92 (d, J=11.15 Hz, 1H), 3.79 (d, J=11.15 Hz, 1H), 2.77-2.73 (m, 1H), 2.60-2.55 (m, 1H), 2.38-2.34 (m, 2H); and Enantiomer 73B: Slower eluting: Rt=3.85 min; $^1$H NMR (CD$_3$OD, 600 MHz) δ (ppm) 8.10 (s, 1H), 5.24 (quintuplet, J=8.80 Hz, 1H), 4.57-4.54 (m, 1H), 3.92 (d, J=11.15 Hz, 1H), 3.79 (d, J=11.15 Hz, 1H), 2.77-2.73 (m, 1H), 2.60-2.55 (m, 1H), 2.38-2.34 (m, 2H).

Examples 75-76

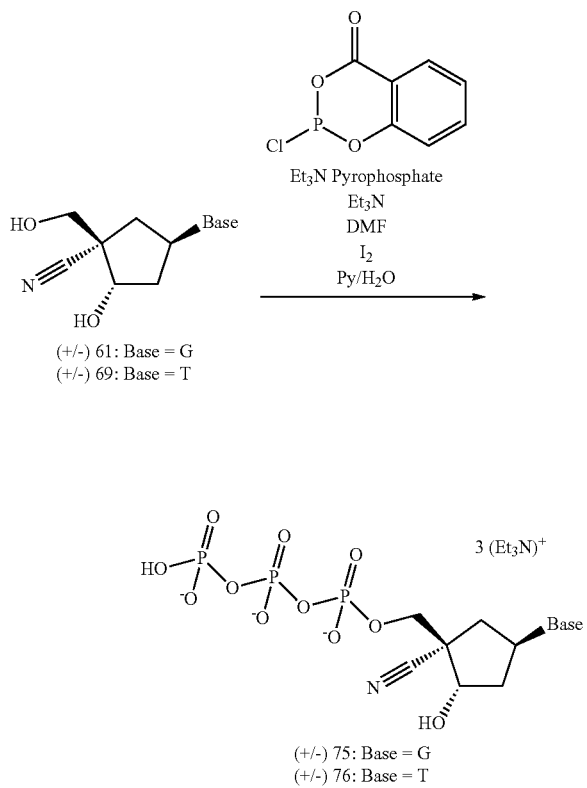

Scheme 16. General procedure for synthesis of triphosphates.

(+/−) 61: Base = G
(+/−) 69: Base = T (+/−) 75: Base = G
(+/−) 76: Base = T

Preparation of Compounds (+/−) 75 and 76:

Compounds (+/−) 75 and 76 were synthesized according to procedure described in litterature: *Chem. Comm.* 2011, 47, 8142-8144.

Compound (+/−) 75: MS (ESI) m/z=529.0 (MH$^-$).

Compound (+/−) 76: MS (ESI) m/z=504.0 (MH$^-$).

TABLE 1
| Ex. | Structure |
|---|---|
| (+/−) 12 | 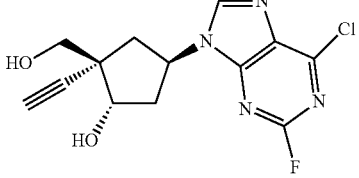<br>and enantiomer |
| (+/−) 13 | 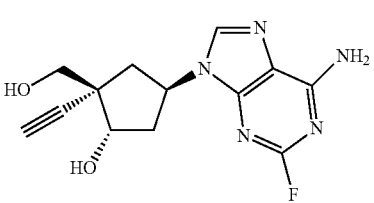<br>and enantiomer |
| (+/−) 14 | 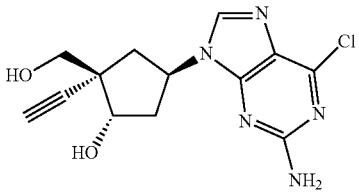<br>and enantiomer |
| (+/−) 17 | 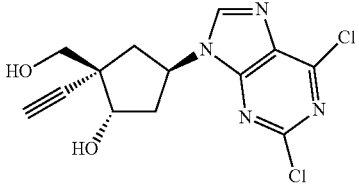<br>and enantiomer |
| (+/−) 18 | 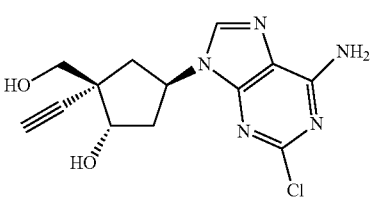<br>and enantiomer |
| 18A | 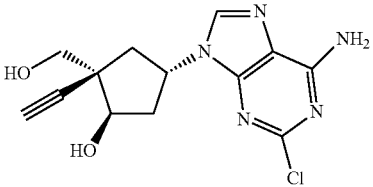<br>or enantiomer |

TABLE 1-continued
| 18B | 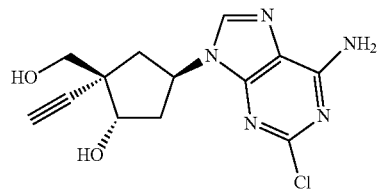 |
|---|---|
| | or enantiomer |
| (+/−) 21 | 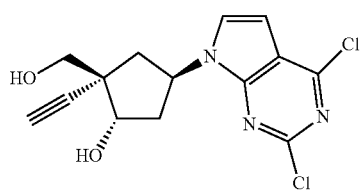 |
| | and enantiomer |
| (+/−) 22 | 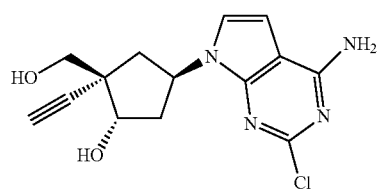 |
| | and enantiomer |
| (+/−) 26 | 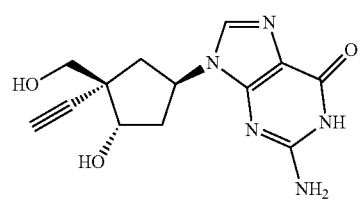 |
| | and enantiomer |
| 26A | 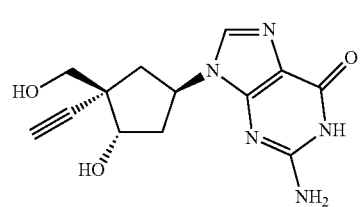 |
| | or enantiomer |
| 26B | 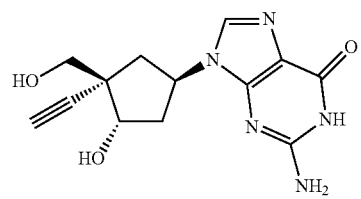 |
| | or enantiomer |
| (+/−) 30 | 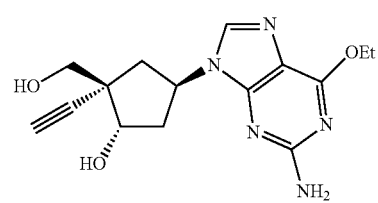 |
| | and enantiomer |

TABLE 1-continued
(+/−) 34
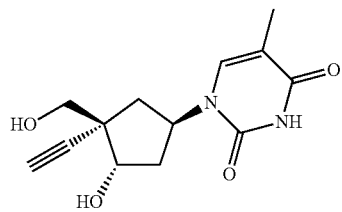
and enantiomer
(+/−) 38
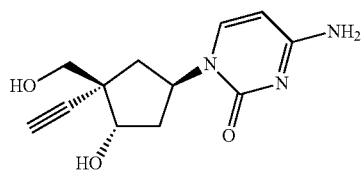
and enantiomer
39A and 39B
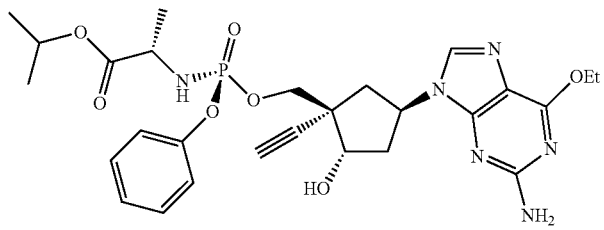
and isomer
39A
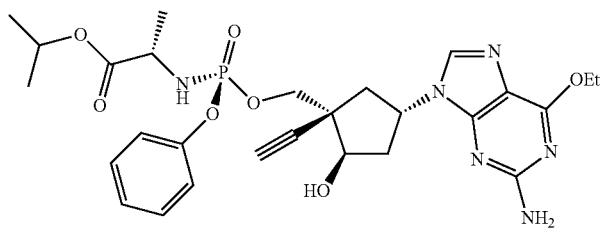
or isomer
39B
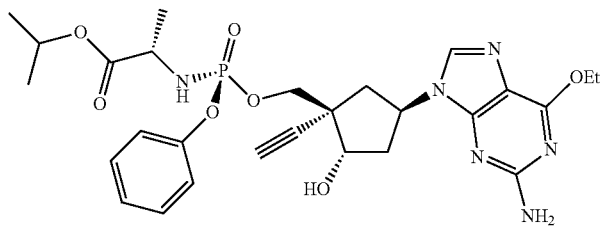
or isomer
(+/−) 61
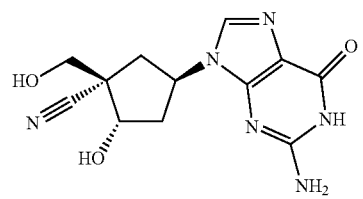
and enantiomer TABLE 1-continued
(+/−) 65
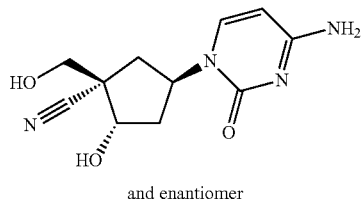 [SMILES: N#C[C@]1(CO)C[C@@H](n2ccc(N)nc2=O)C[C@@H]1O]
and enantiomer
(+/−) 69
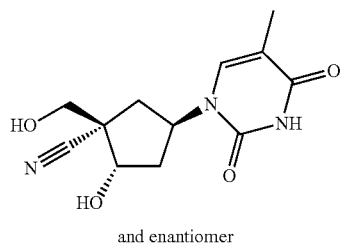 [SMILES: Cc1cn([C@H]2C[C@H](O)[C@@](C#N)(CO)C2)c(=O)[nH]c1=O]
and enantiomer
73A
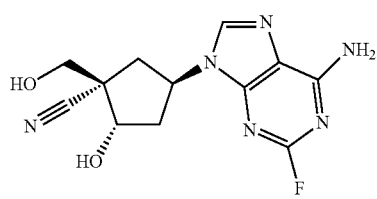
or enantiomer
73B
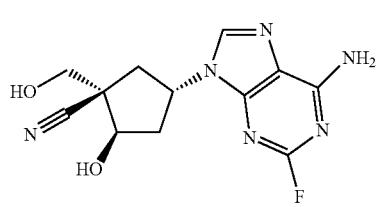
or enantiomer
| Ex. |
| --- |
(+/−) 40
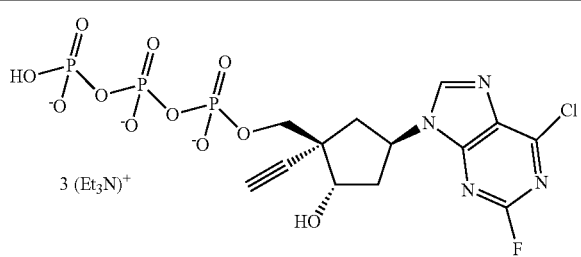
and enantiomer
(+/−) 41
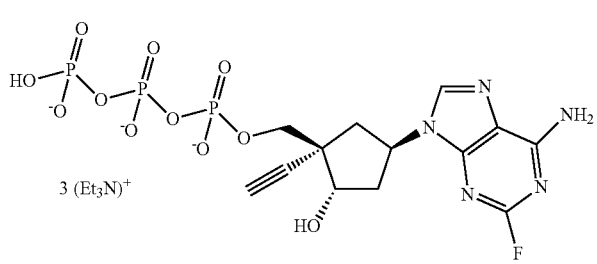
and enantiomer TABLE 1-continued
(+/−) 42 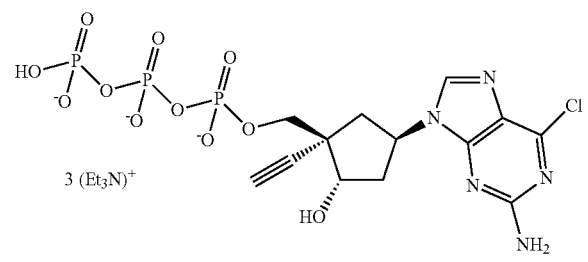
3 (Et₃N)⁺
and enantiomer
(+/−) 43 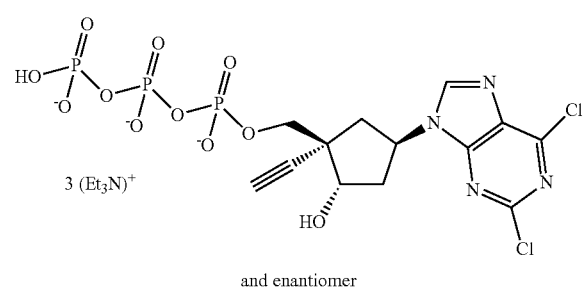
3 (Et₃N)⁺
and enantiomer
(+/−) 44 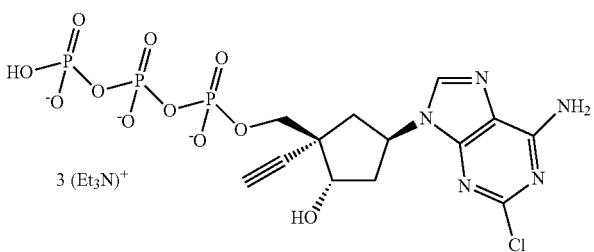
3 (Et₃N)⁺
and enantiomer
44B 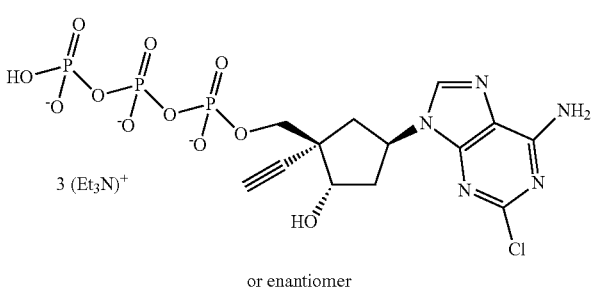
3 (Et₃N)⁺
or enantiomer
(+/−) 45 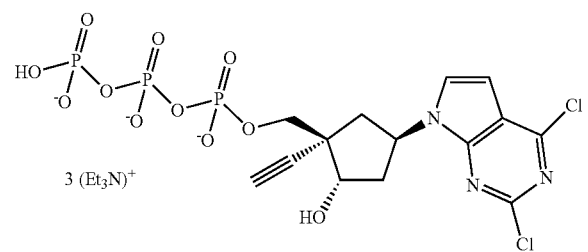
3 (Et₃N)⁺
and enantiomer TABLE 1-continued
(+/−) 46
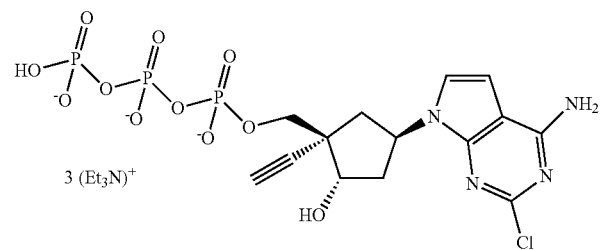
and enantiomer
(+/−) 47
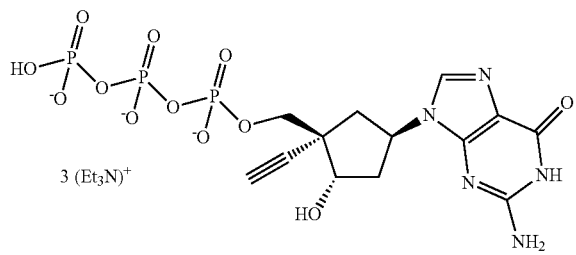
and enantiomer
(+/−) 48
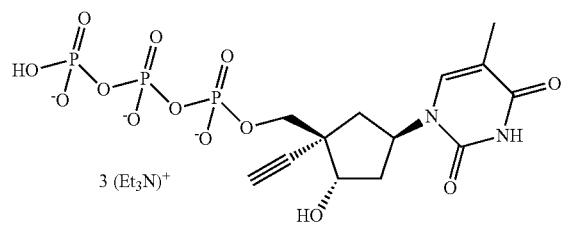
and enantiomer
(+/−) 49
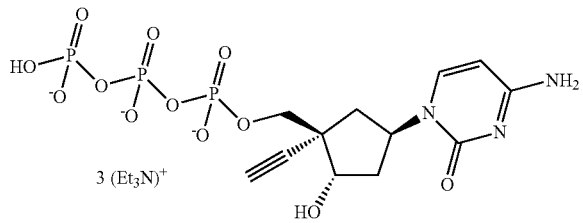
and enantiomer
(+/−) 75
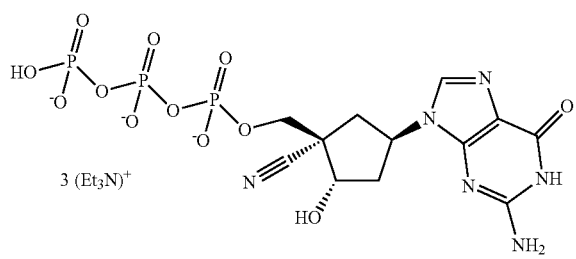
and enantiomer TABLE 1-continued (+/−) 76

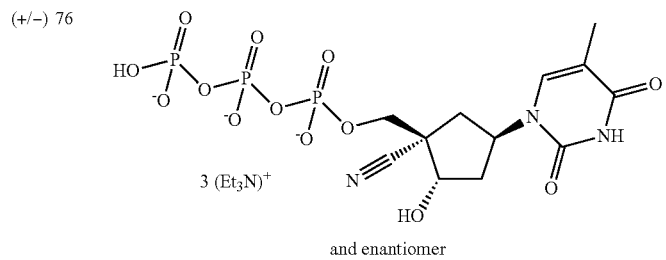

3 (Et₃N)⁺ and enantiomer

TABLE 2

The names of the corresponding salt-free form of the
compounds exemplified above are, respectively:

(+/−) 12  (1S,2S,4R)-4-(6-chloro-2-fluoro-9H-purin-9-yl)-2-ethynyl-2-
(hydroxymethyl)cyclopentan-1-ol and (1R,2R,4S)-4-(6-chloro-2-fluoro-9H-purin-
9-yl)-2-ethynyl-2-(hydroxymethyl)cyclopentan-1-ol:
(+/−) 13  (1S,2S,4R)-4-(6-amino-2-fluoro-9H-purin-9-yl)-2-ethynyl-2-
(hydroxymethyl)cyclopentan-1-ol and (1R,2R,4S)-4-(6-amino-2-fluoro-9H-purin-
9-yl)-2-ethynyl-2-(hydroxymethyl)cyclopentan-1-ol
(+/−) 14  (1S,2S,4R)-4-(2-amino-6-chloro-9H-purin-9-yl)-2-ethynyl-2-
(hydroxymethyl)cyclopentan-1-ol and (1R,2R,4S)-4-(2-amino-6-chloro-9H-purin-
9-yl)-2-ethynyl-2-(hydroxymethyl)cyclopentan-1-ol:
(+/−) 17  (1S,2S,4R)-4-(2,6-dichloro-9H-purin-9-yl)-2-ethynyl-2-
(hydroxymethyl)cyclopentan-1-ol and (1R,2R,4S)-4-(2,6-dichloro-9H-purin-9-yl)-
2-ethynyl-2-(hydroxymethyl)cyclopentan-1-ol
(+/−) 18  (1S,2S,4R)-4-(6-amino-2-chloro-9H-purin-9-yl)-2-ethynyl-2-
(hydroxymethyl)cyclopentan-1-ol and (1R,2R,4S)-4-(6-amino-2-chloro-9H-purin-
9-yl)-2-ethynyl-2-(hydroxymethyl)cyclopentan-1-ol
18A  (1S,2S,4R)-4-(6-amino-2-chloro-9H-purin-9-yl)-2-ethynyl-2-
(hydroxymethyl)cyclopentan-1-ol or (1R,2R,4S)-4-(6-amino-2-chloro-9H-purin-9-
yl)-2-ethynyl-2-(hydroxymethyl)cyclopentan-1-ol
18B  (1S,2S,4R)-4-(6-amino-2-chloro-9H-purin-9-yl)-2-ethynyl-2-
(hydroxymethyl)cyclopentan-1-ol or (1R,2R,4S)-4-(6-amino-2-chloro-9H-purin-9-
yl)-2-ethynyl-2-(hydroxymethyl)cyclopentan-1-ol
(+/−) 21  (1S,2S,4R)-4-(2,4-dichloro-7H-pyrrol[2,3-d]pyrimidin-7-yl)-2-ethynyl-2-
(hydroxymethyl)cyclopentan-1-ol and (1R,2R,4S)-4-(2,4-dichloro-7H-pyrrolo[2,3-
d]pyrimidin-7-yl)-2-ethynyl-2-(hydroxymethyl)cyclopentan-1-ol
(+/−) 22  (1S,2S,4R)-4-(4-amino-2-chloro-7H-pyrrolo[2,3-d]pyrimidin-7-yl)-2-ethynyl-2-
(hydroxymethyl)cyclopentan-1-ol and (1R,2R,4S)-4-(4-amino-2-chloro-7H-
pyrrolo[2,3-d]pyrimidin-7-yl)-2-ethynyl-2-(hydroxymethyl)cyclopentan-1-ol
(+/−) 26  2-amino-9-((lR,3S,4S)-3-ethynyl-4-hydroxy-3-(hydroxymethyl)cyclopentyl)-1,9-
dihydro-6H-purin-6-one and 2-amino-9-((1S,3R,4R)-3-ethynyl-4-hydroxy-3-
(hydroxymethyl)cyclopentyl)-1,9-dihydro-6H-purin-6-one
26A  2-amino-9-((lR,3S,4S)-3-ethynyl-4-hydroxy-3-(hydroxymethyl)cyclopentyl)-1,9-
dihydro-6H-purin-6-one or 2-amino-9-((1S,3R,4R)-3-ethynyl-4-hydroxy-3-
(hydroxymethyl)cyclopentyl)-1,9-dihydro-6H-purin-6-one
26B  2-amino-9-((1R,3S,4S)-3-ethynyl-4-hydroxy-3-(hydroxymethyl)cyclopentyl)-1,9-
dihydro-6H-purin-6-one or 2-amino-9-((1S,3R,4R)-3-ethynyl-4-hydroxy-3-
(hydroxymethyl)cyclopentyl)-1,9-dihydro-6H-purin-6-one
(+/−) 30  (1S,2S,4R)-4-(2-amino-6-ethoxy-9H-purin-9-yl)-2-ethynyl-2-
(hydroxymethyl)cyclopentan-1-ol and (1R,2R,4S)-4-(2-amino-6-ethoxy-9H-purin-
9-yl)-2-ethynyl-2-(hydroxymethyl)cyclopentan-1-ol
(+/−) 34  1-((1R,3S,4S)-3-ethynyl-4-hydroxy-3-(hydroxymethyl)cyclopentyl)-5-
methylpyrimidine-2,4(1H,3H)-dione and 1-((1S,3R,4R)-3-ethynyl-4-hydroxy-3-
(hydroxymethyl)cyclopentyl)-5-methylpyrimidine-2,4(1H,3H)-dione
(+/−) 38  4-amino-1-((1R,3S,4S)-3-ethynyl-4-hydroxy-3-
(hydroxymethyl)cyclopentyl)pyrimidin-2(1H)-one and 4-amino-1-((1S,3R,4R)-3-
ethynyl-4-hydroxy-3-(hydroxymethyl)cyclopentyl)pyrimidin-2(1H)-one
39A and  Isopropyl ((S)-(((1S,2S,4R)-4-(2-amino-6-ethoxy-9H-purin-9-yl)-1-ethynyl-2-
39B  hydroxycyclopentyl)methoxy)(phenoxy)phosphoryl)-L-alaninate and Isopropyl
((S)-(((1R,2R,4S)-4-(2-amino-6-ethoxy-9H-purin-9-yl)-1-ethynyl-2-
hydroxycyclopentyl)methoxy)(phenoxy)phosphoryl)-L-alaninate
39A  Isopropyl ((S)-(((1S,2S,4R)-4-(2-amino-6-ethoxy-9H-purin-9-yl)-1-ethynyl-2-
hydroxycyclopentyl)methoxy)(phenoxy)phosphoryl)-L-alaninate or Isopropyl ((S)-
(((1R,2R,4S)-4-(2-amino-6-ethoxy-9H-purin-9-yl)-1-ethynyl-2-
hydroxycyclopentyl)methoxy)(phenoxy)phosphoryl)-L-alaninate
39B  Isopropyl ((S)-(((1S,2S,4R)-4-(2-amino-6-ethoxy-9H-purin-9-yl)-1-ethynyl-2-
hydroxycyclopentyl)methoxy)(phenoxy)phosphoryl)-L-alaninate or Isopropyl ((S)-
(((1R,2R,4S)-4-(2-amino-6-ethoxy-9H-purin-9-yl)-1-ethynyl-2-
hydroxycyclopentyl)methoxy)(phenoxy)phosphoryl)-L-alaninate
(+/−) 40  ((1S,2S,4R)-4-(6-chloro-2-fluoro-9H-purin-9-yl)-1-ethynyl-2-
hydroxycyclopentyl)methyl tetrahydrogen triphosphate and ((1R,2R,4S)-4-(6-

TABLE 2-continued

The names of the corresponding salt-free form of the
compounds exemplified above are, respectively:

|     |     |
| --- | --- |
|     | chloro-2-fluoro-9H-purin-9-yl)-1-ethynyl-2-hydroxycyclopentyl)methyl tetrahydrogen triphosphate |
| (+/−) 41 | ((1S,2S,4R)-4-(6-amino-2-fluoro-9H-purin-9-yl)-1-ethynyl-2-hydroxycyclopentyl)methyl tetrahydrogen triphosphate and ((1R,2R,4S)-4-(6-amino-2-fluoro-9H-purin-9-yl)-1-ethynyl-2-hydroxycyclopentyl)methyl tetrahydrogen triphosphate |
| (+/−) 42 | ((1S,2S,4R)-4-(2-amino-6-chloro-9H-purin-9-yl)-1-ethynyl-2-hydroxycyclopentyl)methyl tetrahydrogen triphosphate and ((1R,2R,4S)-4-(2-amino-6-chloro-9H-purin-9-yl)-1-ethynyl-2-hydroxycyclopentyl)methyl tetrahydrogen triphosphate |
| (+/−) 43 | ((1S,2S,4R)-4-(2,6-dichloro-9H-purin-9-yl)-1-ethynyl-2-hydroxycyclopentyl)methyl tetrahydrogen triphosphate and ((1R,2R,4S)-4-(2,6-dichloro-9H-purin-9-yl)-1-ethynyl-2-hydroxycyclopentyl)methyl tetrahydrogen triphosphate |
| (+/−) 44 | ((1S,2S,4R)-4-(6-amino-2-chloro-9H-purin-9-yl)-1-ethynyl-2-hydroxycyclopentyl)methyl tetrahydrogen triphosphate and ((1R,2R,4S)-4-(6-amino-2-chloro-9H-purin-9-yl)-1-ethynyl-2-hydroxycyclopentyl)methyl tetrahydrogen triphosphate |
| 44B | ((1S,2S,4R)-4-(6-amino-2-chloro-9H-purin-9-yl)-1-ethynyl-2-hydroxycyclopentyl)methyl tetrahydrogen triphosphate or ((1R,2R,4S)-4-(6-amino-2-chloro-9H-purin-9-yl)-1-ethynyl-2-hydroxycyclopentyl)methyl tetrahydrogen triphosphate |
| (+/−) 45 | ((1S,2S,4R)-4-(2,4-dichloro-7H-pyrrolo[2,3-d]pyrimidin-7-yl)-1-ethynyl-2-hydroxycyclopentyl)methyl tetrahydrogen triphosphate and ((1R,2R,4S)-4-(2,4-dichloro-7H-pyrrolo[2,3-d]pyrimidin-7-yl)-1-ethynyl-2-hydroxycyclopentyl)methyl tetrahydrogen triphosphate |
| (+/−) 46 | ((1S,2S,4R)-4-(4-amino-2-chloro-7H-pyrrolo[2,3-d]pyrimidin-7-yl)-1-ethynyl-2-hydroxycyclopentyl)methyl tetrahydrogen triphosphate and ((1R,2R,4S)-4-(4-amino-2-chloro-7H-pyrrolo[2,3-d]pyrimidin-7-yl)-1-ethynyl-2-hydroxycyclopentyl)methyl tetrahydrogen triphosphate |
| (+/−) 47 | ((1S,2S,4R)-4-(2-amino-6-oxo-1,6-dihydro-9H-purin-9-yl)-1-ethynyl-2-hydroxycyclopentyl)methyl tetrahydrogen triphosphate and ((1R,2R,4S)-4-(2-amino-6-oxo-1,6-dihydro-9H-purin-9-yl)-1-ethynyl-2-hydroxycyclopentyl)methyl tetrahydrogen triphosphate |
| (+/−) 48 | ((1S,2S,4R)-1-ethynyl-2-hydroxy-4-(5-methyl-2,4-dioxo-3,4-dihydropyrimidin-1(2H)-yl)cyclopentyl)methyl tetrahydrogen triphosphate and ((1R,2R,4S)-1-ethynyl-2-hydroxy-4-(5-methyl-2,4-dioxo-3,4-dihydropyrimidin-1(2H)-yl)cyclopentyl)methyl tetrahydrogen triphosphate |
| (+/−) 49 | ((1S,2S,4R)-4-(4-amino-2-oxopyrimidin-1(2H)-yl)-1-ethynyl-2-hydroxycyclopentyl)methyl tetrahydrogen triphosphate and ((1R,2R,4S)-4-(4-amino-2-oxopyrimidin-1(2H)-yl)-1-ethynyl-2-hydroxycyclopentyl)methyl tetrahydrogen triphosphate |
| (+/−) 61 | (1S,2S,4R)-4-(2-amino-6-oxo-1,6-dihydro-9H-purin-9-yl)-2-hydroxy-1-(hydroxymethyl)cyclopentane-1-carbonitrile and (1R,2R,4S)-4-(2-amino-6-oxo-1,6-dihydro-9H-purin-9-yl)-2-hydroxy-1-(hydroxymethyl)cyclopentane-1-carbonitrile |
| (+/−) 65 | (1S,2S,4R)-4-(4-amino-2-oxopyrimidin-1(2H)-yl)-2-hydroxy-1-(hydroxymethyl)cyclopentane-1-carbonitrile and (1R,2R,4S)-4-(4-amino-2-oxopyrimidin-1(2H)-yl)-2-hydroxy-1-(hydroxymethyl)cyclopentane-1-carbonitrile |
| (+/−) 69 | (1S,2S,4R)-2-hydroxy-1-(hydroxymethyl)-4-(5-methyl-2,4-dioxo-3,4-dihydropyrimidin-1(2H)-yl)cyclopentane-1-carbonitrile and (1R,2R,4S)-2-hydroxy-1-(hydroxymethyl)-4-(5-methyl-2,4-dioxo-3,4-dihydropyrimidin-1(2H)-yl)cyclopentane-1-carbonitrile |
| 73A | (1S,2S,4R)-4-(6-amino-2-fluoro-9H-purin-9-yl)-2-hydroxy-1-(hydroxymethyl)cyclopentane-1-carbonitrile or (1R,2R,4S)-4-(6-amino-2-fluoro-9H-purin-9-yl)-2-hydroxy-1-(hydroxymethyl)cyclopentane-1-carbonitrile |
| 73B | (1S,2S,4R)-4-(6-amino-2-fluoro-9H-purin-9-yl)-2-hydroxy-1-(hydroxymethyl)cyclopentane-1-carbonitrile or (1R,2R,4S)-4-(6-amino-2-fluoro-9H-purin-9-yl)-2-hydroxy-1-(hydroxymethyl)cyclopentane-1-carbonitrile |
| (+/−) 75 | ((1S,2S,4R)-4-(2-amino-6-oxo-1,6-dihydro-9H-purin-9-yl)-1-cyano-2-hydroxycyclopentyl)methyl tetrahydrogen triphosphate and ((1R,2R,4S)-4-(2-amino-6-oxo-1,6-dihydro-9H-purin-9-yl)-1-cyano-2-hydroxycyclopentyl)methyl tetrahydrogen triphosphate |
| (+/−) 76 | ((1S,2S,4R)-1-cyano-2-hydroxy-4-(5-methyl-2,4-dioxo-3,4-dihydropyrimidin-1(2H)-yl)cyclopentyl)methyl tetrahydrogen triphosphate and ((1R,2R,4S)-1-cyano-2-hydroxy-4-(5-methyl-2,4-dioxo-3,4-dihydropyrimidin-1(2H)-yl)cyclopentyl)methyl tetrahydrogen triphosphate |

RT Polymerase Assay

Full-length wild-type and 2 mutant RT proteins were expressed in *Escherichia coli* BL21(DE3) cells and purified. Briefly, the heterodimeric nucleic acid substrate used in the HIV-1 RT polymerase reactions was generated by annealing biotinylated DNA primer to a 500 nucleotide RNA template. The HIV-1 RT enzyme (final concentration of 50 pM) was combined with an inhibitor compound or DMSO (10% DMSO in the final reaction mixture) in assay buffer (62.5 mM Tris-HCl, pH 7.8, 1.25 mM dithiothreitol, 7.5 mM MgCl2, 100 mM KCl, 0.03% CHAPS, 0.125 mM EGTA). This mixture was pre-incubated for 30 minutes at room temperature in microtiter plates. The polymerization reaction was initiated by the addition of template/primer substrate (final concentration: 16.6 nM) and dNTPs (final concentration: 2 μM dCTP, dGTP, dATP, and 66.6 nM Ru-dUTP). After 90 min of incubation at 37° C., reactions were quenched by the addition of EDTA (25 mM). The resulting mixture was incubated for an additional 5 minutes at room temperature followed by transferring the solution (50 μL) to blocked avidin plate from Meso Scale Discovery (MSD). The mixtures were incubated at room temperature for 60 min prior to the quantification of the reaction product via an ECL 6000 imager instrument. The resulting data is shown in Table 3.

TABLE 3

| Example No. | Structure | dNTP IC$_{50}$ (nM) |
| --- | --- | --- |
| (+/−) 40 | 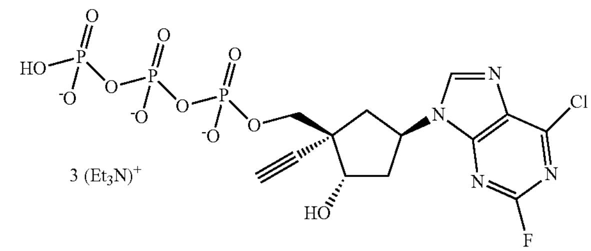 | >100000 |
| (+/−) 41 | 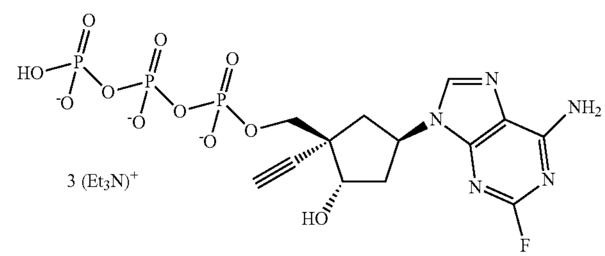 | 3456 |
| (+/−) 42 | 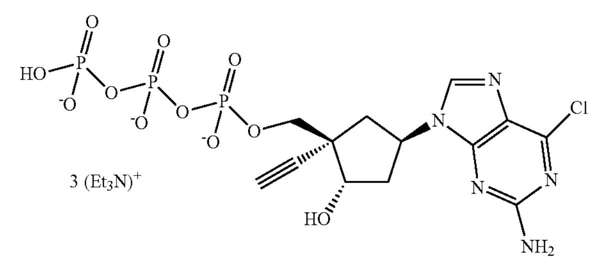 | 13170 |
| (+/−) 43 | 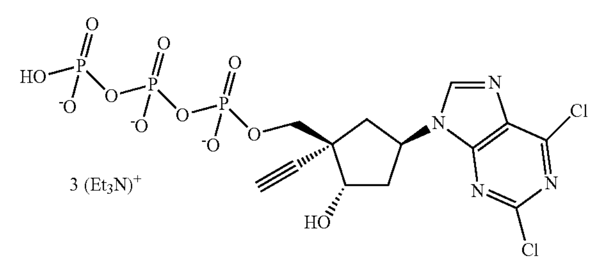 | >100000 |

TABLE 3-continued
| Example No. | Structure | dNTP IC$_{50}$ (nM) |
|---|---|---|
| (+/−) 44 | 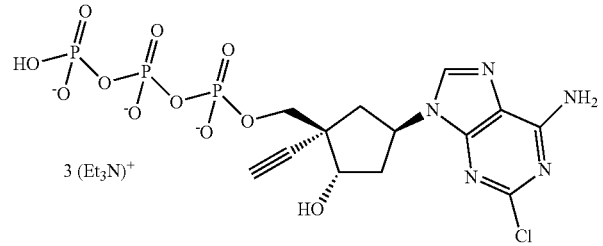<br>and enantiomer | 20160 |
| 44B | 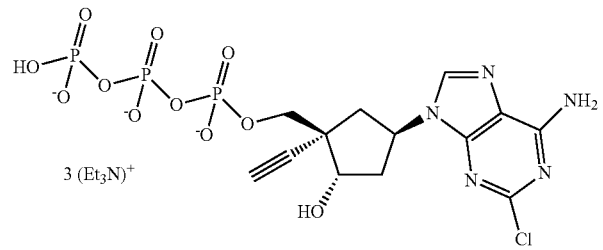<br>or enantiomer | 9317 |
| (+/−) 45 | 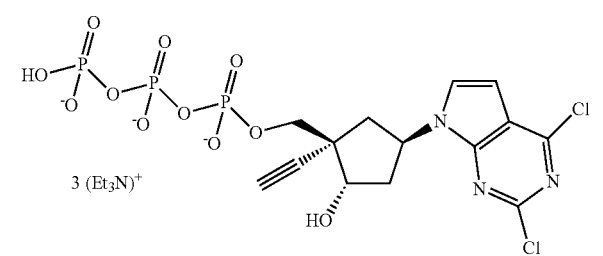<br>and enantiomer | 33840 |
| (+/−) 46 | 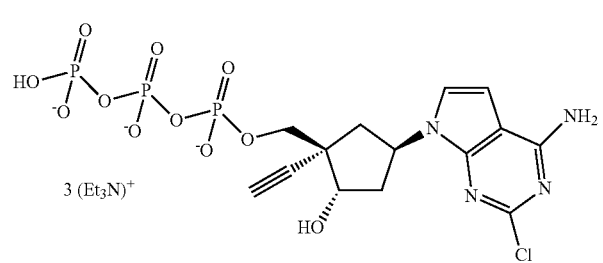<br>and enantiomer | 13860 |
| (+/−) 47 | 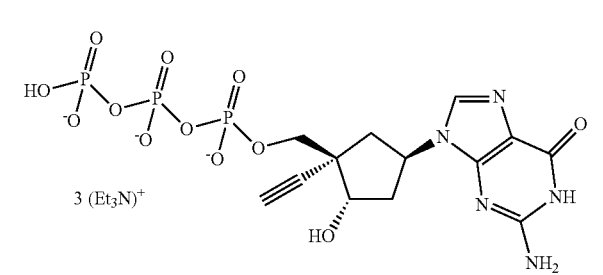<br>and enantiomer | 324 |

TABLE 3-continued

| Example No. | Structure | dNTP IC$_{50}$ (nM) |
|---|---|---|
| (+/−) 48 | [Structure: triphosphate-CH$_2$-cyclopentane with ethynyl, OH, and thymine base; 3 (Et$_3$N)$^+$; and enantiomer] | 114 |
| (+/−) 49 | [Structure: triphosphate-CH$_2$-cyclopentane with ethynyl, OH, and cytosine base; 3 (Et$_3$N)$^+$; and enantiomer] | >100000 |
| (+/−) 75 | [Structure: triphosphate-CH$_2$-cyclopentane with nitrile, OH, and guanine base; 3 (Et$_3$N)$^+$; and enantiomer] | 444 |
| (+/−) 76 | [Structure: triphosphate-CH$_2$-cyclopentane with nitrile, OH, and thymine base; 3 (Et$_3$N)$^+$; and enantiomer] | 523 |

Viking Assay/CTG

Viking Assay:

Assessing Antiviral Potency in a Multiple Round HIV-1 Infection Assay.

HIV-1 replication was monitored using MT4-gag-GFP clone D3 (hereafter designate MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24h post-infection.

MT4-GFP cells were maintained at 37° C./5% CO$_{2/90}$% relative humidity in RPMI 1640 supplemented with 10% fetal bovine serum, 100 U/mL penicillin/streptomycin, and 400 μg/mL G418 to maintain the reporter gene. For infections, MT4-GFP cells were placed in the same medium lacking G418 and infected overnight with H9IIIB virus at an approximate multiplicity of infection of 0.01 in the same incubation conditions. Cells were then washed and re-suspended in either RPMI 1640 containing 10% or 50% normal human serum at 1.6×10$^5$ cells/mL. Compound plates were prepared by dispensing compounds dissolved in DMSO into wells of 384 well poly D lysine-coated plates (0.2l/well) using an ECHO acoustic dispenser. Each compound was tested in a 10 point serial 3-fold dilution (typical final concentrations: 8.4 μM-0.43 nM). Controls included no inhibitor (DMSO only) and a combination of three antiviral agents (efavirenz, indinavir, and an integrase strand transfer inhibitor at final concentrations of 4 μM each). Cells were added (50 μL/well) to compound plates and the infected cells were maintained at 37° C./5% CO$_{2/90}$% relative humidity.

Infected cells were quantified at two time points, ~48h and ~72h post-infection, by counting the number of green cells in each well using an Acumen eX3 scanner. The increase in the number of green cells over ~24h period gives the reproductive ratio, R$_0$, which is typically 5-15 and has been shown experimentally to be in logarithmic phase (data not shown). Inhibition of $R_0$ is calculated for each well, and $IC_{50}$s determined by non-linear 4-parameter curve fitting.
CTG Assay:
Assessing Cytotoxicity in CellTiter-Glo Luminescent Cell Viability Assay (CTG).

MT4-GFP cells were seeded in RPMI 1640 supplemented with 10% fetal bovine serum, 100 U/mL penicillin/streptomycin overnight at 37° C./5% $CO_2$/90% relative humidity. Cells were then washed and resuspended in RPMI 1640 containing 10% normal human serum at a density of $0.8 \times 10^5$ cells/mL. Compound plates were prepared by dispensing compounds dissolved in DMSO into wells of 384 well solid black plates (Corning 3571) using an ECHO acoustic dispenser (0.2 µl/well). Each compound was tested in a 10 point serial 3-fold dilution (final concentrations: 8.4 µM-0.43 nM). Controls included DMSO. Cells were added (50 µL/well) to compound plates and were maintained at 37° C./5% $CO_2$/90% relative humidity. CTG reagent (Promega, G7573) was added to the cell plates after 48h incubation according to the manufacturer's description. Luminescence signals were recorded on EnVision plate reader (PerkinElmer). $CC_{50}$s were determined by non-linear 4-parameter curve fitting. The resulting data is shown in Table 3 with the marketed HIV nucleoside reverse transcriptase inhibitor AZT (azidothymidine, zidovudine) included as a control.

TABLE 4

| | Structure | Viking, $IC_{50}$ (10% NHS)(nM) | CTG (µM) |
|---|---|---|---|
| AZT | 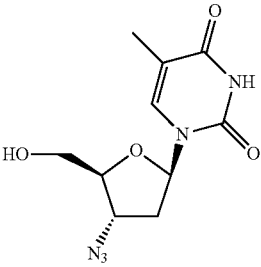 [SMILES: Cc1cn([C@H]2C[C@H](N=[N+]=[N-])[C@@H](CO)O2)c(=O)[nH]c1=O] | 37 | >8.4 |
| Example No. | | | |
| (+/−) 12 | 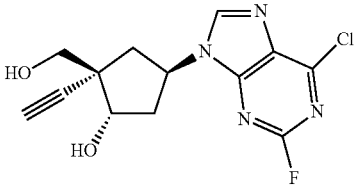 and enantiomer | >42020 | 25040 |
| (+/−) 13 | 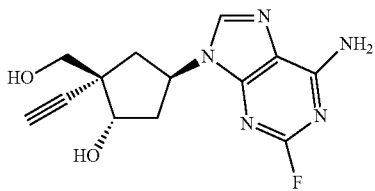 and enantiomer | 5431 | >42020 |
| (+/−) 14 | 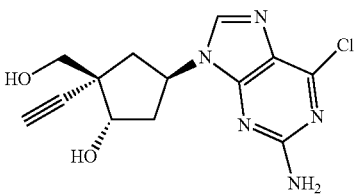 and enantiomer | 5642 | >42020 |

TABLE 4-continued

| Structure | Viking, IC$_{50}$ (10% NHS)(nM) | CTG (μM) |
|---|---|---|
| (+/−) 17 *and enantiomer* | 17400 | 19880 |
| (+/−) 18 *and enantiomer* | 19020 | >42020 |
| 18A *or enantiomer* | 25180 | >42020 |
| 18B *or enantiomer* | 11650 | >42020 |
| (+/−) 21 *and enantiomer* | >42020 | >42020 |
| (+/−) 22 *and enantiomer* | 22190 | >42020 |

TABLE 4-continued
| | Structure | Viking, IC$_{50}$ (10% NHS)(nM) | CTG (μM) |
|---|---|---|---|
| (+/−) 26 | 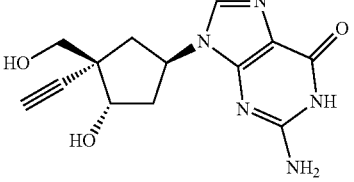 and enantiomer | 194.9 | >42020 |
| 26A | 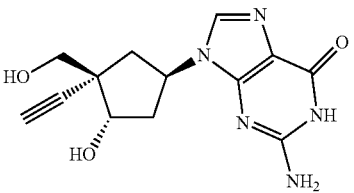 or enantiomer | >42020 | >42020 |
| 26B | 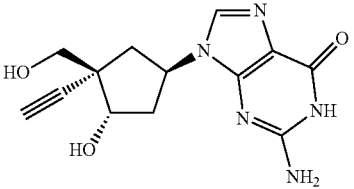 or enantiomer | 142.2 | >42020 |
| (+/−) 30 | 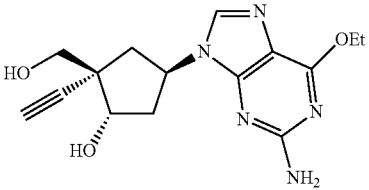 and enantiomer | 613.8 | >42020 |
| (+/−) 34 | 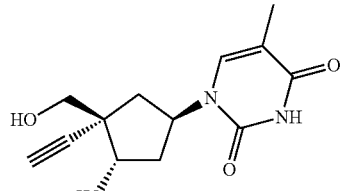 and enantiomer | >42020 | >42020 |
| (+/−) 38 | 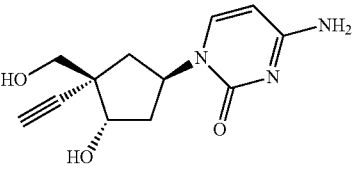 and enantiomer | >42020 | >42020 |

TABLE 4-continued

| | Structure | Viking, IC$_{50}$ (10% NHS)(nM) | CTG (μM) |
|---|---|---|---|
| 39A and 39B | and isomer | 27.1 | >42020 |
| 39A | or isomer | 483.9 | >42020 |
| 39B | or isomer | 5.932 | >4202 |
| (+/−) 61 | and enantiomer | 998 | >42020 |
| (+/−) 65 | and enantiomer | >42020 | >42020 |
| (+/−) 69 | and enantiomer | 15980 | >42020 |

TABLE 4-continued

| Structure | Viking, IC$_{50}$ (10% NHS)(nM) | CTG (μM) |
|---|---|---|
| 73A 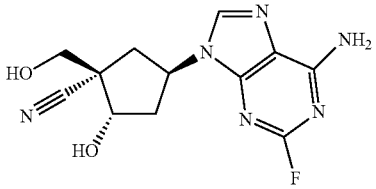 or enantiomer | >42020 | >42020 |
| 73B 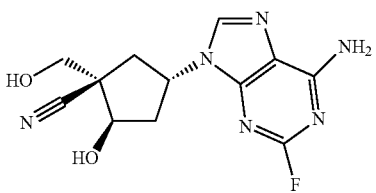 or enantiomer | 11020 | >42020 |

While the foregoing specification teaches the principles of the present invention, with examples provided for the purpose of illustration, the practice of the invention encompasses all of the usual variations, adaptations and/or modifications that come within the scope of the following claims. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All publications, patents and patent applications cited herein are incorporated by reference in their entirety into the disclosure.

What is claimed:

1. A compound of structural Formula I

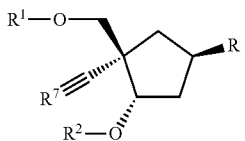

I or a pharmaceutically acceptable salt thereof, wherein:

R is

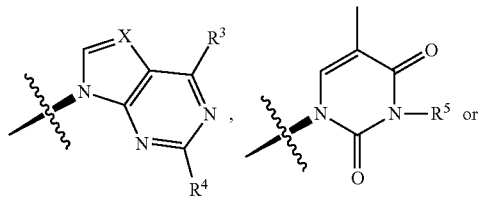

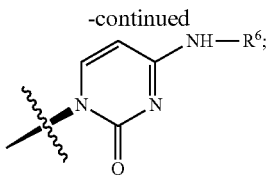

X is —N— or —C(H)—;

R$^7$ is —CH, —N, —C$_{1-6}$ alkyl or —C-aryl;

R$^1$ is H,

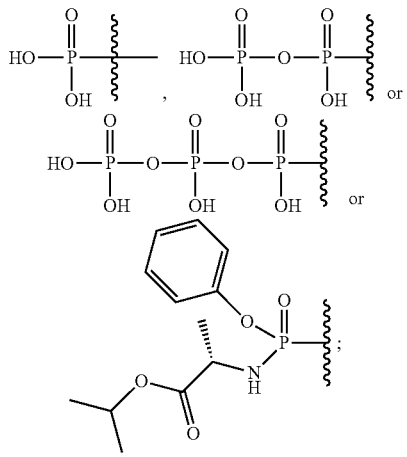

R$^2$ is H or —CH$_2$—O—C$_{1-6}$alkyl;

R$^3$ is halo, —NH$_2$, oxo (=O), —O—C$_{1-6}$alkyl or —O—C(O)—N(phenyl)$_2$;

R$^4$ is halo or —NR$^a$R$^b$;

R$^a$ and R$^b$ are each independently selected from —H, —C$_{1-6}$alkyl or —C(O)—C$_{1-6}$alkyl;

R$^5$ is —H or —C(O)-phenyl; and

R$^6$ is —H or —C(O)-phenyl.

2. The compound of claim 1 or a pharmaceutically acceptable salt thereof wherein:
R¹ is H,

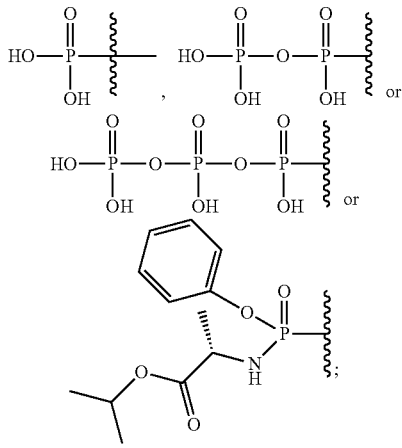

R² is H or —CH₂—O—C₁₋₃alkyl;
R³ is halo, —NH₂, oxo, —O—C₁₋₃alkyl or —O—C(O)—N(phenyl)₂; and
R⁴ is halo, —NH₂ or —NH—C(O)—C₁₋₃ alkyl.

3. The compound of claim 1 that is:
(1S,2S,4R)-4-(6-chloro-2-fluoro-9H-purin-9-yl)-2-ethynyl-2-(hydroxymethyl)cyclopentan-1-ol and (1R,2R,4S)-4-(6-chloro-2-fluoro-9H-purin-9-yl)-2-ethynyl-2-(hydroxymethyl)cyclopentan-1-ol;
(1S,2S,4R)-4-(6-amino-2-fluoro-9H-purin-9-yl)-2-ethynyl-2-(hydroxymethyl)cyclopentan-1-ol and (1R,2R,4S)-4-(6-amino-2-fluoro-9H-purin-9-yl)-2-ethynyl-2-(hydroxymethyl)cyclopentan-1-ol;
(1S,2S,4R)-4-(2-amino-6-chloro-9H-purin-9-yl)-2-ethynyl-2-(hydroxymethyl)cyclopentan-1-ol and (1R,2R,4S)-4-(2-amino-6-chloro-9H-purin-9-yl)-2-ethynyl-2-(hydroxymethyl)cyclopentan-1-ol;
(1S,2S,4R)-4-(2,6-dichloro-9H-purin-9-yl)-2-ethynyl-2-(hydroxymethyl)cyclopentan-1-ol and (1R,2R,4S)-4-(2,6-dichloro-9H-purin-9-yl)-2-ethynyl-2-(hydroxymethyl)cyclopentan-1-ol;
(1S,2S,4R)-4-(6-amino-2-chloro-9H-purin-9-yl)-2-ethynyl-2-(hydroxymethyl)cyclopentan-1-ol and (1R,2R,4S)-4-(6-amino-2-chloro-9H-purin-9-yl)-2-ethynyl-2-(hydroxymethyl)cyclopentan-1-ol;
(1S,2S,4R)-4-(6-amino-2-chloro-9H-purin-9-yl)-2-ethynyl-2-(hydroxymethyl)cyclopentan-1-ol or (1R,2R,4S)-4-(6-amino-2-chloro-9H-purin-9-yl)-2-ethynyl-2-(hydroxymethyl)cyclopentan-1-ol;
(1S,2S,4R)-4-(6-amino-2-chloro-9H-purin-9-yl)-2-ethynyl-2-(hydroxymethyl)cyclopentan-1-ol or (1R,2R,4S)-4-(6-amino-2-chloro-9H-purin-9-yl)-2-ethynyl-2-(hydroxymethyl)cyclopentan-1-ol;
(1S,2S,4R)-4-(2,4-dichloro-7H-pyrrolo[2,3-d]pyrimidin-7-yl)-2-ethynyl-2-(hydroxymethyl)cyclopentan-1-ol and (1R,2R,4S)-4-(2,4-dichloro-7H-pyrrolo[2,3-d]pyrimidin-7-yl)-2-ethynyl-2-(hydroxymethyl)cyclopentan-1-ol;
(1S,2S,4R)-4-(4-amino-2-chloro-7H-pyrrolo[2,3-d]pyrimidin-7-yl)-2-ethynyl-2-(hydroxymethyl)cyclopentan-1-ol and (1R,2R,4S)-4-(4-amino-2-chloro-7H-pyrrolo[2,3-d]pyrimidin-7-yl)-2-ethynyl-2-(hydroxymethyl)cyclopentan-1-ol;

2-amino-9-((1R,3S,4S)-3-ethynyl-4-hydroxy-3-(hydroxymethyl)cyclopentyl)-1,9-dihydro-6H-purin-6-one and 2-amino-9-((1S,3R,4R)-3-ethynyl-4-hydroxy-3-(hydroxymethyl)cyclopentyl)-1,9-dihydro-6H-purin-6-one;
2-amino-9-((1R,3S,4S)-3-ethynyl-4-hydroxy-3-(hydroxymethyl)cyclopentyl)-1,9-dihydro-6H-purin-6-one or 2-amino-9-((1S,3R,4R)-3-ethynyl-4-hydroxy-3-(hydroxymethyl)cyclopentyl)-1,9-dihydro-6H-purin-6-one;
2-amino-9-((1R,3S,4S)-3-ethynyl-4-hydroxy-3-(hydroxymethyl)cyclopentyl)-1,9-dihydro-6H-purin-6-one or 2-amino-9-((1S,3R,4R)-3-ethynyl-4-hydroxy-3-(hydroxymethyl)cyclopentyl)-1,9-dihydro-6H-purin-6-one;
(1S,2S,4R)-4-(2-amino-6-ethoxy-9H-purin-9-yl)-2-ethynyl-2-(hydroxymethyl)cyclopentan-1-ol and (1R,2R,4S)-4-(2-amino-6-ethoxy-9H-purin-9-yl)-2-ethynyl-2-(hydroxymethyl)cyclopentan-1-ol;
1-((1R,3S,4S)-3-ethynyl-4-hydroxy-3-(hydroxymethyl)cyclopentyl)-5-methylpyrimidine-2,4(1H,3H)-dione and 1-((1S,3R,4R)-3-ethynyl-4-hydroxy-3-(hydroxymethyl)cyclopentyl)-5-methylpyrimidine-2,4(1H,3H)-dione;
4-amino-1-((1R,3S,4S)-3-ethynyl-4-hydroxy-3-(hydroxymethyl)cyclopentyl)pyrimidin-2(1H)-one and 4-amino-1-((1S,3R,4R)-3-ethynyl-4-hydroxy-3-(hydroxymethyl)cyclopentyl)pyrimidin-2(1H)-one;
Isopropyl ((S)-(((1S,2S,4R)-4-(2-amino-6-ethoxy-9H-purin-9-yl)-1-ethynyl-2-hydroxycyclopentyl)methoxy)(phenoxy)phosphoryl)-L-alaninate and Isopropyl ((S)-(((1R,2R,4S)-4-(2-amino-6-ethoxy-9H-purin-9-yl)-1-ethynyl-2-hydroxycyclopentyl)methoxy)(phenoxy)phosphoryl)-L-alaninate;
Isopropyl ((S)-(((1S,2S,4R)-4-(2-amino-6-ethoxy-9H-purin-9-yl)-1-ethynyl-2-hydroxycyclopentyl)methoxy)(phenoxy)phosphoryl)-L-alaninate or Isopropyl ((S)-(((1R,2R,4S)-4-(2-amino-6-ethoxy-9H-purin-9-yl)-1-ethynyl-2-hydroxycyclopentyl)methoxy)(phenoxy)phosphoryl)-L-alaninate;
Isopropyl ((S)-(((1S,2S,4R)-4-(2-amino-6-ethoxy-9H-purin-9-yl)-1-ethynyl-2-hydroxycyclopentyl)methoxy)(phenoxy)phosphoryl)-L-alaninate or Isopropyl ((S)-(((1R,2R,4S)-4-(2-amino-6-ethoxy-9H-purin-9-yl)-1-ethynyl-2-hydroxycyclopentyl)methoxy)(phenoxy)phosphoryl)-L-alaninate;
((1S,2S,4R)-4-(6-chloro-2-fluoro-9H-purin-9-yl)-1-ethynyl-2-hydroxycyclopentyl)methyl tetrahydrogen triphosphate and ((1R,2R,4S)-4-(6-chloro-2-fluoro-9H-purin-9-yl)-1-ethynyl-2-hydroxycyclopentyl)methyl tetrahydrogen triphosphate;
((1S,2S,4R)-4-(6-amino-2-fluoro-9H-purin-9-yl)-1-ethynyl-2-hydroxycyclopentyl)methyl tetrahydrogen triphosphate and ((1R,2R,4S)-4-(6-amino-2-fluoro-9H-purin-9-yl)-1-ethynyl-2-hydroxycyclopentyl)methyl tetrahydrogen triphosphate;
((1S,2S,4R)-4-(2-amino-6-chloro-9H-purin-9-yl)-1-ethynyl-2-hydroxycyclopentyl)methyl tetrahydrogen triphosphate and ((1R,2R,4S)-4-(2-amino-6-chloro-9H-purin-9-yl)-1-ethynyl-2-hydroxycyclopentyl)methyl tetrahydrogen triphosphate;
((1S,2S,4R)-4-(2,6-dichloro-9H-purin-9-yl)-1-ethynyl-2-hydroxycyclopentyl)methyl tetrahydrogen triphosphate and ((1R,2R,4S)-4-(2,6-dichloro-9H-purin-9-yl)-1-ethynyl-2-hydroxycyclopentyl)methyl tetrahydrogen triphosphate;

((1S,2S,4R)-4-(6-amino-2-chloro-9H-purin-9-yl)-1-ethynyl-2-hydroxycyclopentyl)methyl tetrahydrogen triphosphate and ((1R,2R,4S)-4-(6-amino-2-chloro-9H-purin-9-yl)-1-ethynyl-2-hydroxycyclopentyl)methyl tetrahydrogen triphosphate;

((1S,2S,4R)-4-(6-amino-2-chloro-9H-purin-9-yl)-1-ethynyl-2-hydroxycyclopentyl)methyl tetrahydrogen triphosphate or ((1R,2R,4S)-4-(6-amino-2-chloro-9H-purin-9-yl)-1-ethynyl-2-hydroxycyclopentyl)methyl tetrahydrogen triphosphate;

((1S,2S,4R)-4-(2,4-dichloro-7H-pyrrolo[2,3-d]pyrimidin-7-yl)-1-ethynyl-2-hydroxycyclopentyl)methyl tetrahydrogen triphosphate and ((1R,2R,4S)-4-(2,4-dichloro-7H-pyrrolo[2,3-d]pyrimidin-7-yl)-1-ethynyl-2-hydroxycyclopentyl)methyl tetrahydrogen triphosphate;

((1S,2S,4R)-4-(4-amino-2-chloro-7H-pyrrolo[2,3-d]pyrimidin-7-yl)-1-ethynyl-2-hydroxycyclopentyl)methyl tetrahydrogen triphosphate and ((1R,2R,4S)-4-(4-amino-2-chloro-7H-pyrrolo[2,3-d]pyrimidin-7-yl)-1-ethynyl-2-hydroxycyclopentyl)methyl tetrahydrogen triphosphate;

((1S,2S,4R)-4-(2-amino-6-oxo-1,6-dihydro-9H-purin-9-yl)-1-ethynyl-2-hydroxycyclopentyl)methyl tetrahydrogen triphosphate and ((1R,2R,4S)-4-(2-amino-6-oxo-1,6-dihydro-9H-purin-9-yl)-1-ethynyl-2-hydroxycyclopentyl)methyl tetrahydrogen triphosphate;

((1S,2S,4R)-1-ethynyl-2-hydroxy-4-(5-methyl-2,4-dioxo-3,4-dihydropyrimidin-1(2H)-yl)cyclopentyl)methyl tetrahydrogen triphosphate and ((1R,2R,4S)-1-ethynyl-2-hydroxy-4-(5-methyl-2,4-dioxo-3,4-dihydropyrimidin-1(2H)-yl)cyclopentyl)methyl tetrahydrogen triphosphate;

((1S,2S,4R)-4-(4-amino-2-oxopyrimidin-1(2H)-yl)-1-ethynyl-2-hydroxycyclopentyl)methyl tetrahydrogen triphosphate and ((1R,2R,4S)-4-(4-amino-2-oxopyrimidin-1(2H)-yl)-1-ethynyl-2-hydroxycyclopentyl)methyl tetrahydrogen triphosphate;

(1S,2S,4R)-4-(2-amino-6-oxo-1,6-dihydro-9H-purin-9-yl)-2-hydroxy-1-(hydroxymethyl)cyclopentane-1-carbonitrile and (1R,2R,4S)-4-(2-amino-6-oxo-1,6-dihydro-9H-purin-9-yl)-2-hydroxy-1-(hydroxymethyl)cyclopentane-1-carbonitrile;

(1S,2S,4R)-4-(4-amino-2-oxopyrimidin-1(2H)-yl)-2-hydroxy-1-(hydroxymethyl)cyclopentane-1-carbonitrile and (1R,2R,4S)-4-(4-amino-2-oxopyrimidin-1(2H)-yl)-2-hydroxy-1-(hydroxymethyl)cyclopentane-1-carbonitrile;

(1S,2S,4R)-2-hydroxy-1-(hydroxymethyl)-4-(5-methyl-2,4-dioxo-3,4-dihydropyrimidin-1(2H)-yl)cyclopentane-1-carbonitrile and (1R,2R,4S)-2-hydroxy-1-(hydroxymethyl)-4-(5-methyl-2,4-dioxo-3,4-dihydropyrimidin-1(2H)-yl)cyclopentane-1-carbonitrile;

(1S,2S,4R)-4-(6-amino-2-fluoro-9H-purin-9-yl)-2-hydroxy-1-(hydroxymethyl)cyclopentane-1-carbonitrile or (1R,2R,4S)-4-(6-amino-2-fluoro-9H-purin-9-yl)-2-hydroxy-1-(hydroxymethyl)cyclopentane-1-carbonitrile;

(1S,2S,4R)-4-(6-amino-2-fluoro-9H-purin-9-yl)-2-hydroxy-1-(hydroxymethyl)cyclopentane-1-carbonitrile or (1R,2R,4S)-4-(6-amino-2-fluoro-9H-purin-9-yl)-2-hydroxy-1-(hydroxymethyl)cyclopentane-1-carbonitrile;

((1S,2S,4R)-4-(2-amino-6-oxo-1,6-dihydro-9H-purin-9-yl)-1-cyano-2-hydroxycyclopentyl)methyl tetrahydrogen triphosphate and ((1R,2R,4S)-4-(2-amino-6-oxo-1,6-dihydro-9H-purin-9-yl)-1-cyano-2-hydroxycyclopentyl)methyl tetrahydrogen triphosphate; or ((1S,2S,4R)-1-cyano-2-hydroxy-4-(5-methyl-2,4-dioxo-3,4-dihydropyrimidin-1(2H)-y l)cyclopentyl)methyl tetrahydrogen triphosphate and ((1R,2R,4S)-1-cyano-2-hydroxy-4-(5-methyl-2,4-dioxo-3,4-dihydropyrimidin-1(2H)-yl)cyclopentyl)methyl tetrahydrogen triphosphate;

or a pharmaceutically acceptable salt thereof.

4. A pharmaceutical composition comprising an effective amount of a compound of claim 1, or a pharmaceutically acceptable salt thereof, and a pharmaceutically acceptable carrier.

5. A pharmaceutical composition comprising an effective amount of a compound of claim 1, or a pharmaceutically acceptable salt thereof, and a pharmaceutically acceptable carrier and further comprising an effective amount of an anti-HIV agent selected from an anti-HIV antiviral agent, an immunomodulator, or anti-infective agent.

6. The pharmaceutical composition of claim 5, wherein the anti-HIV antiviral agent is an HIV protease inhibitor, HIV reverse transcriptase inhibitor, HIV integrase inhibitor, HIV fusion inhibitor, HIV entry inhibitor, or HIV maturation inhibitor.

7. The pharmaceutical composition of claim 4 further comprising one or more additional HIV antiviral agents selected from:

abacavir, abacavir sulfate, abacavir+lamivudine, abacavir+lamivudine+zidovudine, amprenavir, atazanavir, atazanavir sulfate, AZT, capravirine, darunavir, dideoxycytidine, dideoxyinosine, delavirdine, delavirdine mesylate, dolutegravir, doravirine, efavirenz, 4'-ethynyl-2-fluoro-2'-deoxyadenosine, elvitegravir, emtricitabine, emivirine, enfuvirtide, etravirine, fosamprenavir calcium, indinavir, indinavir sulfate, lamivudine, lamivudine+zidovudine, lopinavir, lopinavir+ritonavir, maraviroc, nelfinavir, nelfinavir mesylate, nevirapine, PPL-100, raltegravir, rilpivirine, ritonavir, saquinavir, saquinavir mesylate, stavudine, tipranavir, or vicriviroc.

8. A method for the treatment of infection by HIV or for the treatment or delay in the onset of AIDS in a subject in need thereof, which comprises administering to the subject an effective amount of the compound of claim 1, or a pharmaceutically acceptable salt thereof.

* * * * *